(12) United States Patent
McBride et al.

(10) Patent No.: US 11,771,029 B2
(45) Date of Patent: Oct. 3, 2023

(54) MICROBIAL COMPOSITIONS FOR THE PREVENTION OR REDUCTION OF GROWTH OF FUNGAL PATHOGENS ON PLANTS

(71) Applicant: Boost Biome, Inc., Berkeley, CA (US)

(72) Inventors: Robert McBride, South San Francisco, CA (US); Karen Hunt, South San Francisco, CA (US); Jamie Bacher, South San Francisco, CA (US); Veronica Garcia, South San Francisca, CA (US); James Pearce, La Jolla, CA (US)

(73) Assignee: Boost Biomes, Inc., Berkeley, CA (US)

( * ) Notice: Subject to any disclaimer, the term of this patent is extended or adjusted under 35 U.S.C. 154(b) by 117 days.

(21) Appl. No.: 16/990,882

(22) Filed: Aug. 11, 2020

(65) Prior Publication Data

US 2021/0112815 A1    Apr. 22, 2021

Related U.S. Application Data

(63) Continuation of application No. PCT/US2019/017692, filed on Feb. 12, 2019.

(60) Provisional application No. 62/629,525, filed on Feb. 12, 2018.

(51) Int. Cl.

| *A01N 63/20* | (2020.01) |
| *A01N 63/32* | (2020.01) |
| *A01H 3/00* | (2006.01) |
| *A01N 63/50* | (2020.01) |
| *A01N 63/27* | (2020.01) |
| *A01N 63/22* | (2020.01) |
| *A01C 1/06* | (2006.01) |
| *A01C 21/00* | (2006.01) |

(52) U.S. Cl.
CPC ................ *A01H 3/00* (2013.01); *A01C 1/06* (2013.01); *A01C 21/00* (2013.01); *A01N 63/20* (2020.01); *A01N 63/22* (2020.01); *A01N 63/27* (2020.01); *A01N 63/32* (2020.01); *A01N 63/50* (2020.01)

(58) Field of Classification Search
CPC ........ A01N 63/22; A01N 63/32; A01N 63/50; A01N 63/27; A01N 63/20
See application file for complete search history.

(56) References Cited

U.S. PATENT DOCUMENTS

| 5,780,023 | A | 7/1998 | McLaughlin et al. |
| 2010/0311819 | A1 | 12/2010 | Van De Craen et al. |
| 2014/0314718 | A1 | 10/2014 | Hinarejos et al. |
| 2016/0010114 | A1 | 1/2016 | Drewniak et al. |
| 2016/0262402 | A1 | 9/2016 | Thompson et al. |
| 2016/0366892 | A1 | 12/2016 | Ambrose et al. |
| 2017/0049102 | A1 | 2/2017 | Van Der Weerden et al. |
| 2018/0222966 | A1 | 8/2018 | Verheesen et al. |
| 2019/0008158 | A1 | 1/2019 | Von Maltzahn |
| 2019/0059387 | A1 | 2/2019 | Besoain Canales et al. |
| 2019/0085352 | A1 | 3/2019 | Goldman et al. |
| 2022/0256861 | A1 | 8/2022 | Garcia et al. |

FOREIGN PATENT DOCUMENTS

| CN | 1934241 | A | 3/2007 |
| CN | 101423812 | A | 5/2009 |
| CN | 102333857 | A | 1/2012 |
| CN | 103740604 | A | 4/2014 |
| EP | 3751991 | A1 | 12/2020 |
| EP | 4014000 | A1 | 6/2022 |
| JP | 2009072168 | A | 4/2009 |
| KR | 20060110546 | A | 10/2006 |
| KR | 20130124752 | A | 11/2013 |
| WO | WO-9821964 | A1 | 5/1998 |
| WO | WO-9946405 | A1 | 9/1999 |
| WO | WO-0245513 | A2 | 6/2002 |
| WO | WO-2015114552 | A1 | 8/2015 |
| WO | WO-2015200902 | A2 | 12/2015 |
| WO | WO-2016123191 | A1 | 8/2016 |
| WO | WO-2017112827 | A1 | 6/2017 |
| WO | WO-2017136944 | A1 | 8/2017 |
| WO | WO2017088081 | | * 10/2017 |
| WO | WO-2019157518 | A1 | 8/2019 |
| WO | WO-2021030195 | A2 | 2/2021 |
| WO | WO-2021030577 | A1 | 2/2021 |

OTHER PUBLICATIONS

Albertin, et al. Hanseniaspora uvarum from Winemaking Environments Show Spatial and Temporal Genetic Clustering. Front Microbiol. Jan. 20, 2016;6:1569.

Breen, et al. Surveying the potential of secreted antimicrobial peptides to enhance plant disease resistance. Front Plant Sci. 2015; 6: 900. Published online Oct. 27, 2015. doi: 10.3389/fpls.2015. 00900.

Cadez, et al. Molecular identification and genetic diversity within species of the genera *Hanseniaspora* and *Kloeckera*. FEMS Yeast Res. Jan. 2002;1(4):279-89.

Castellano, et al. Strategies for Pathogen Biocontrol Using Lactic Acid Bacteria and Their Metabolites: A Focus on Meat Ecosystems and Industrial Environments. Microorganisms. Sep. 2017; 5(3): 38. Published online Jul. 11, 2017.

(Continued)

*Primary Examiner* — Michael G. Hartley
*Assistant Examiner* — Danielle Sullivan
(74) *Attorney, Agent, or Firm* — Wilson Sonsini Goodrich & Rosati

(57) ABSTRACT

Disclosed herein are biocontrol compositions against plant fungal pathogens and methods of use thereof for the prevention or reduction of crop loss or food spoilage. The biocontrol composition can comprise at least one microbe with anti-fungal activity or a secondary metabolite of the at least one microbe. The methods can comprise application of the biocontrol composition to a plant, a seed, or a produce thereof or to a packaging material used to transport or store the produce.

19 Claims, 66 Drawing Sheets

Specification includes a Sequence Listing.

(56) References Cited

OTHER PUBLICATIONS

Certis USA. Label for Double Nickel55 Biofungicide—WaterDispersible Granular Biofungicide. Available at http://www.certisusa.com/pdf-labels/DoubleNickel_55_label.pdf. Accessed Nov. 22, 2017.
Chen, et al. Comparative analysis of the complete genome sequence of the plant growthpromoting bacterium *Bacillus amyloliquefaciens* FZB42. Nat Biotechnol. Sep. 2007;25(9):1007-14. Epub Aug. 19, 2007.
Gulay, et al. Internal Porosity of Mineral Coating Supports Microbial Activity in Rapid Sand Filters for Groundwater Treatment. Appl Environ Microbiol. Nov. 2014; 80(22): 7010-7020.
Irkin, et al. Novel food packaging systems with natural antimicrobial agents. J Food Sci Technol. Oct. 2015; 52(10): 6095-6111.
Isagro USA. Slides fortraining—Isagro TAEGRO 2 biofungicide Product Training. 2017.
Jayawardena, et al., Notes on currently accepted species of colletotrichum, Mycosphere, Dec. 26, 2016; 7(8): 1192-1260.
Kamat, et al. Xylitol production by Cyberlindnera (Williopsis) saturnus, a tropical mangrove yeast from xylose and corn cob hydrolysate. J Appl Microbiol. Dec. 2013;115(6):1357-67. doi: 10.1111/jam.12327. Epub Sep. 13, 2013.
Kaur, et al. Draft Genome Sequence of Phosphate-Solubilizing Bacterium Paraburkholderia tropica Strain P-31 Isolated from Pomegranate (*Punica granatum*) Rhizosphere. Genome Announc. Jul.-Aug. 2016; 4(4): e00844-16.
Kim, et al. Effectiveness of Different Classes of Fungicides on Botrytis cinerea Causing Gray Mold on Fruit and Vegetables. Plant Pathol J. Dec. 2016; 32(6): 570-574. Published online Dec. 1, 2016.
Liu, et al. Inhibitory activity of tea polyphenol and Hanseniaspora uvarum against Botrytis cinerea infections. Letters in Applied Microbiology. 51(3):258-263, Sep. 2010.
[No Author] Bacillus amyloliquefaciens subs, plantarum strain D747. List of studies which are considered as relied upon by the RMS for the evaluation with a view to Annex I renewal and for which the main submitter has claimed data protection. Rapporteur Member State: Germany. Feb. 2016.
PCT/US2019/017692 International Search Report and Written Opinion dated Jun. 18, 2019.
Radler, et al. Killer toxin of Hanseniaspora uvarum. Arch Microbiol. 1990;154(2):175-8.
Radler, et al. Killer toxins in new isolates of the yeasts Hanseniaspora uvarum and Pichia kluyveri. FEMS Microbiology Letters. vol. 29, Issue 3, Sep. 1985, pp. 269-272.
Romano, et al. Biometric Study of Acetoin Production in Hanseniaspora guilliermondii and Kloeckera apiculata. Appl Environ Microbiol. Jun. 1993;59(6):1838-41.
Ruiz-Moyano, et al. Yeasts isolated from figs (*Ficus carica* L.) as biocontrol agents of postharvest fruit diseases. Food Microbiol. Aug. 2016;57:45-53.
Salas, et al. Antifungal Microbial Agents for Food Biopreservation—A Review. Microorganisms. Sep. 2017; 5(3): 37.
Sarma, et al. Microbial consortium-mediated plant defense against phytopathogens: Readdressing for enhancing efficacy. Soil biology & biochemistry 2015 v.87 pp. 25-33.
Scherm, et al. Biological control of infection of blueberry flowers caused by Monilinia vaccinii-corymbosi, Biological control. Feb. 1, 2004; 29(2): 199-206.
Taqarort, et al. Screening and identification of epiphytic yeasts with potential for biological control of green mold of citrus fruits. World Journal of Microbiology and Biotechnology; Oxford vol. 24, Iss. 12, (Dec. 2008): 3031-3038.
Yuan, et al. Antifungal activity of Bacillus amyloliquefaciens NJN-6 volatile compounds against *Fusarium oxysporum* f. sp. cubense. Appl Environ Microbiol. Aug. 2012;78(16):5942-4. doi: 10.1128/AEM.01357-12. Epub Jun. 8, 2012.
Co-pending U.S. Appl. No. 17/666,449, inventors GarciaVeronica et al., filed Feb. 7, 2022.
Database EMBL [Online] "Hanseniaspora uvarum culture CBS:314 small subunit ribosomal RNA gene, partial sequence; internal transcribed spacer 1, 5.8S ribosomal RNA gene, and internal transcribed spacer 2, complete sequence; and large subunit ribosomal RNA gene, partial sequence.", Nov. 23, 2016, Database accession No. KY103558.
EP19751388.0 Extended European Search Report dated Jul. 1, 2022.
EP19751388.0 Partial Supplementary European Search Report dated Mar. 16, 2022.
Murphy, J.F. et al., Rhizobacteria-Mediated Growth Promotion of Tomato Leads to Protection Against Cucumber mosaic virus. Phytopathology. Oct. 2003;93(10):1301-7. doi: 10.1094/PHYTO.2003.93.10.1301. PMID: 18944330.
PCT/US2020/045426 International Search Report and Written Opinion dated Jan. 28, 2021.
PCT/US2020/046165 International Search Report and Written Opinion dated Dec. 2, 2020.
GenBank databases, NCBI. Accession No. LN623599, [online], Feb. 27, 2015, https://www.ncbi.nlm.nih.gov/nuccore/LN623599.
GenBank databases, NCBI. Accession No. KY816895, [online], Apr. 7, 2017, https://www.ncbi.nlm.nih.gov/nuccore/KY816895.

* cited by examiner

FIG. 6

(-) ctrl (+) ctrl

BC16 Product

SEQUENCE LISTING

```
<160> NUMBER OF SEQ ID NOS: 28

<210> SEQ ID NO 1
<211> LENGTH: 216
<212> TYPE: DNA
<213> ORGANISM: Bacillus amyloliquefaciens
<220> FEATURE:
<221> NAME/KEY: modified_base
<222> LOCATION: (19)..(19)
<223> OTHER INFORMATION: a, c, t, g, unknown or other
<220> FEATURE:
<221> NAME/KEY: modified_base
<222> LOCATION: (36)..(36)
<223> OTHER INFORMATION: a, c, t, g, unknown or other
<220> FEATURE:
<221> NAME/KEY: modified_base
<222> LOCATION: (49)..(49)
```

<223> OTHER INFORMATION: a, c, t, g, unknown or other

<400> SEQUENCE: 1

```
caagcgttgt ccggaattnt tgggcgtaaa gggctncgca ggcggtttnc ttaagtctga      60
tgtgaaagcc cccggctcaa ccggggaggg tcatttggaa actggggaac ttgagtgcag     120
aagaggagag tggaattcca cgtgtagcgg tgaaatgcgt agagatgtgg aggaacacca     180
gtggcgaagg cgactctctg gtctgtaact gacgct                               216
```

<210> SEQ ID NO 2
<211> LENGTH: 205
<212> TYPE: DNA
<213> ORGANISM: Gluconacetobacter liquefaciens

<400> SEQUENCE: 2

```
cggaatgact gggcgtaaag gcgcgtagg cggtatggac agtcagatgt gaaattcctg      60
ggcttaacct gggggctgca tttgatacgt ccaaaactag agtgtgagag agggttgtgg    120
aattcccagt gtagaggtga aattcgtaga tattgggaag aacaccggtg gcgaaggcgg    180
caacctggct cataactgac gctga                                          205
```

<210> SEQ ID NO 3
<211> LENGTH: 215
<212> TYPE: DNA
<213> ORGANISM: Unknown
<220> FEATURE:
<223> OTHER INFORMATION: Description of Unknown:
      Paraburkholderia or Burkholderia sequence

<400> SEQUENCE: 3

```
cgttaatcgg aattactggg cgtaaagcgt gcgcaggcgg ttcgctaaga cagatgtgaa      60
atccccgggc ttaacctggg aactgcattt gtgactggcg gctagagta tggcagaggg    120
gggtagaatt ccacgtgtag cagtgaaatg cgtagagatg tggaggaata ccgatggcga    180
aggcagcccc ctgggccaat actgacgctc atgca                               215
```

<210> SEQ ID NO 4
<211> LENGTH: 237
<212> TYPE: DNA
<213> ORGANISM: Gluconacetobacter liquefaciens

<400> SEQUENCE: 4

```
aagggggcta gcgttgctcg gaatgactgg gcgtaaaggg cgcgtaggcg gtatggacag      60
tcagatgtga aattcctggg cttaacctgg gggctgcatt tgatacgtcc aaactagagt    120
gtgagagagg gttgtggaat tcccagtgta gaggtgaaat tcgtagatat tgggaagaac    180
accggtggcg aaggcggcaa cctggctcat aactgacgct gaggcgcgaa agcgtgg       237
```

<210> SEQ ID NO 5
<211> LENGTH: 305
<212> TYPE: DNA
<213> ORGANISM: Gluconacetobacter liquefaciens

<400> SEQUENCE: 5

```
gaagggggct agcgttgctc ggaatgactg ggcgtaaagg gcgcgtaggc ggtatggaca      60
gtcagatgtg aaattcctgg gcttaacctg ggggctgcat ttgatacgtc caaactagag    120
tgtgagagag ggttgtggaa ttcccagtgt agaggtgaaa ttcgtagata ttgggaagaa    180
caccggtggc gaaggcggca acctggctca taactgacgc tgaggcgcga aagcgtgggg    240
```

```
agcaaacagg attagatacc cccgtagtcc ctgtctctta tacacatctc cgagcccacg    300
agaca                                                                305

<210> SEQ ID NO 6
<211> LENGTH: 260
<212> TYPE: DNA
<213> ORGANISM: Pseudomonas fluorescens

<400> SEQUENCE: 6
gcaagcgtta atcggaatta ctgggcgtaa agcgcgcgta ggtggttcgt taagttggat     60
gtgaaatccc cgggctcaac ctgggaactg cattcaaaac tgtcgagcta gagtatggta    120
gagggtggtg gaatttcctg tgtagcggtg aaatgcgtag atataggaag gaacaccagt    180
ggcgaaggcg accacctgga ctgatactga cactgaggtg cgaaagcgtg gggagcaaac    240
aggattagat accccgtag                                                 260

<210> SEQ ID NO 7
<211> LENGTH: 312
<212> TYPE: DNA
<213> ORGANISM: Unknown
<220> FEATURE:
<223> OTHER INFORMATION: Description of Unknown:
      Paraburkholderia or Burkholderia sequence

<400> SEQUENCE: 7
gtaatacgta gggtgcaagc gttaatcgga attactgggc gtaaagcgtg cgcaggcggt     60
tcgctaagac agatgtgaaa tccccgggct taacctggga actgcatttg tgactggcgg    120
gctagagtat ggcagagggg ggtagaattc cacgtgtagc agtgaaatgc gtagagatgt    180
ggaggaatac cgatggcgaa ggcagccccc tgggccaata ctgacgctca tgcacgaaag    240
cgtggggagc aaacaggatt agataccccc gtagtccctg tctcttatac acatctccga    300
gcccacgaga ca                                                        312

<210> SEQ ID NO 8
<211> LENGTH: 298
<212> TYPE: DNA
<213> ORGANISM: Unknown
<220> FEATURE:
<223> OTHER INFORMATION: Description of Unknown:
      Microbial sequence

<400> SEQUENCE: 8
gcaagcgtta atcggaatta ctgggcgtaa agcgcgcgta ggtggtttgt taagttggat     60
gtgaaagccc cgggctcaac ctgggaactg cattcaaaac tgacaagcta gagtatggta    120
gagggtggtg gaatttcctg tgtagcggtg aaatgcgtag atataggaag gaacaccagt    180
ggcgaaggcg accacctgga ctgatactga cactgaggtg cgaaagcgtg gggagcaaac    240
aggattagat accccgtag tccctgtctc ttatacacat ctccgagccc acgagaca       298

<210> SEQ ID NO 9
<211> LENGTH: 364
<212> TYPE: DNA
<213> ORGANISM: Unknown
<220> FEATURE:
<223> OTHER INFORMATION: Description of Unknown:
      Paraburkholderia or Burkholderia sequence
<220> FEATURE:
<221> NAME/KEY: modified_base
<222> LOCATION: (109)..(109)
<223> OTHER INFORMATION: a, c, t, g, unknown or other
<220> FEATURE:
```

```
<221> NAME/KEY: modified_base
<222> LOCATION: (111)..(112)
<223> OTHER INFORMATION: a, c, t, g, unknown or other

<400> SEQUENCE: 9
tgttttgtcg gcagcgtcag atgtgtataa gagacaggtg tcagcagccg cggtaatacg      60
tagggtgcaa gcgttaatcg gaattactgg gcgtaaagcg tgcgcaggng nntcgctaag     120
acagatgtga atccccggg cttaacctgg gaactgcatt tgtgactggc gggctagagt      180
atggcagagg ggggtagaat ccacgtgta gcagtgaaat gcgtagagat gtggaggaat      240
accgatggcg aaggcagccc cctgggccaa tactgacgct catgcacgaa agcgtgggga     300
gcaaacagga ttagatacc cggtagtccc tgtctcttat acacatctcc gagcccacga      360
gaca                                                                   364

<210> SEQ ID NO 10
<211> LENGTH: 228
<212> TYPE: DNA
<213> ORGANISM: Pseudomonas lini

<400> SEQUENCE: 10
caagcgttaa tcggaattac tgggcgtaaa gcgcgcgtag gtggttcgtt aagttggatg      60
tgaaatcccc gggctcaacc tgggaactgc attcaaaact gtcgagctag agtatggtag     120
agggtggtgg aatttcctgt gtagcggtga atgcgtaga tataggaagg aacaccagtg     180
gcgaaggcga ccacctggac tgatactgac actgaggtgc gaaagcgt                   228

<210> SEQ ID NO 11
<211> LENGTH: 302
<212> TYPE: DNA
<213> ORGANISM: Gluconacetobacter liquefaciens
<220> FEATURE:
<221> NAME/KEY: modified_base
<222> LOCATION: (288)..(288)
<223> OTHER INFORMATION: a, c, t, g, unknown or other

<400> SEQUENCE: 11
ttgtttcgtc ggcagcgtca gatgtgtata agagacaggt gtcagccgcc gcggtaatac      60
gaagggggct agcgttgctc ggaatgactg gcgtaaagg gcgcgtaggc ggtatggaca     120
gtcagatgtg aaattcctgg gcttaacctg ggggctgcat ttgatacgtc caaactagag    180
tgtgagagag ggttgtggaa ttcccagtgt agaggtgaaa ttcgtagata ttgggaagaa     240
caccggtggc gaaggcggca acctggctca taactgacgc tgaggcgnga aagcgtgggg     300
ag                                                                    302

<210> SEQ ID NO 12
<211> LENGTH: 227
<212> TYPE: DNA
<213> ORGANISM: Gluconacetobacter liquefaciens

<400> SEQUENCE: 12 aaggggggcta gcgttgctcg gaatgactgg gcgtaaaggg cgcgtaggcg gtatggacag      60
tcagatgtga aattcctggg cttaacctgg ggctgcatt tgatacgtcc aaactagagt     120
gtgagagagg gttgtggaat tcccagtgta gaggtgaaat tcgtagatat tgggaagaac     180
accggtggcg aaggcggcaa cctggctcat aactgacgct gaggcgc                    227

<210> SEQ ID NO 13
<211> LENGTH: 226
```

<212> TYPE: DNA
<213> ORGANISM: Gluconacetobacter liquefaciens

<400> SEQUENCE: 13

```
aaggggcta gcgttgctcg aatgactgg gcgtaaaggg cgcgtaggcg gtatggacag      60
tcagatgtga aattcctggg cttaacctgg gggctgcatt tgatacgtcc aaactagagt   120
gtgagagagg gttgtggaat tcccagtgta gaggtgaaat tcgtagatat tgggaagaac   180
accggtggcg aagcggcaa cctggctcat aactgacgct gaggcg                   226
```

<210> SEQ ID NO 14
<211> LENGTH: 235
<212> TYPE: DNA
<213> ORGANISM: Gluconacetobacter liquefaciens

<400> SEQUENCE: 14

```
aaggggcta gcgttgctcg aatgactgg gcgtaaaggg cgcgtaggcg gtatggacag      60
tcagatgtga aattcctggg cttaacctgg gggctgcatt tgatacgtcc aaactagagt   120
gtgagagagg gttgtggaat tcccagtgta gaggtgaaat tcgtagatat tgggaagaac   180
accggtggcg aagcggcaa cctggctcat aactgacgct gaggcgcgaa agcgt         235
```

<210> SEQ ID NO 15
<211> LENGTH: 237
<212> TYPE: DNA
<213> ORGANISM: Pseudomonas sp.

<400> SEQUENCE: 15

```
tgcaagcgtt aatcggaatt actgggcgta aagcgcgcgt aggtggttcg ttaagttgga    60
tgtgaaatcc ccgggctcaa cctgggaact gcattcaaaa ctgtcgagct agagtatggt   120
agagggtggt ggaatttcct gtgtagcggt gaaatgcgta gatataggaa ggaacaccag   180
tggcgaaggc gaccacctgg actgatactg acactgaggt gcgaaagcgt ggggagc      237
```

<210> SEQ ID NO 16
<211> LENGTH: 228
<212> TYPE: DNA
<213> ORGANISM: Gluconacetobacter liquefaciens
<220> FEATURE:
<221> NAME/KEY: modified_base
<222> LOCATION: (15)..(15)
<223> OTHER INFORMATION: a, c, t, g, unknown or other

<400> SEQUENCE: 16

```
aggggctag cgttnctcgg aatgactggg cgtaaagggc gcgtaggcgg tatggacagt     60
cagatgtgaa attcctgggc ttaacctggg ggctgcattt gatacgtcca aactagagtg   120
tgagagaggg ttgtggaatt cccagtgtag aggtgaaatt cgtagatatt gggaagaaca   180
ccggtggcga aggcggcaac ctggctcata actgacgctg aggcgcga                228
```

<210> SEQ ID NO 17
<211> LENGTH: 213
<212> TYPE: DNA
<213> ORGANISM: Unknown
<220> FEATURE:
<223> OTHER INFORMATION: Description of Unknown:
      Cyberlindnera mrakii or Cyberlindnera saturnus sequence
<220> FEATURE:
<221> NAME/KEY: modified_base
<222> LOCATION: (183)..(183)
<223> OTHER INFORMATION: a, c, t, g, unknown or other
<220> FEATURE:
<221> NAME/KEY: modified_base
<222> LOCATION: (198)..(198)
<223> OTHER INFORMATION: a, c, t, g, unknown or other

<400> SEQUENCE: 17
aggtgaacct gcggaaggat cattaaagta ttcttcggtg cagccagcgc ttccacagcg   60
cggcagccca aaccttacac actgtgatta gttttttcta ctatttactt tggctgcacg  120
aagtggccaa aggttcttaa acacaaaaga tttatatctt tttttacaaa atttagtcaa  180
tgnagtttta atactatnat ctttcaaaac ttt                               213

<210> SEQ ID NO 18
<211> LENGTH: 220
<212> TYPE: DNA
<213> ORGANISM: Hanseniaspora uvarum
<220> FEATURE:
<221> NAME/KEY: modified_base
<222> LOCATION: (4)..(4)
<223> OTHER INFORMATION: a, c, t, g, unknown or other
<220> FEATURE:
<221> NAME/KEY: modified_base
<222> LOCATION: (9)..(9)
<223> OTHER INFORMATION: a, c, t, g, unknown or other
<220> FEATURE:
<221> NAME/KEY: modified_base
<222> LOCATION: (157)..(157)
<223> OTHER INFORMATION: a, c, t, g, unknown or other
<220> FEATURE:
<221> NAME/KEY: modified_base
<222> LOCATION: (160)..(160)
<223> OTHER INFORMATION: a, c, t, g, unknown or other
<220> FEATURE:
<221> NAME/KEY: modified_base
<222> LOCATION: (210)..(210)
<223> OTHER INFORMATION: a, c, t, g, unknown or other

<400> SEQUENCE: 18
aatngcgcng cttctttaga gtgtcgcagt aaaagtagtc ttgcttgaat ctcagtcaac   60
gctacacaca ttcggagttt ttttatttta ttttatttct ttcgcttttg attcaaaggg  120
tccaggccaa aaaccaaccc caaccatttt aatttantan tatttttttta acctaaccca  180 aatttcctac cgaaattttt aaattatttn aaacctttca                        220

<210> SEQ ID NO 19
<211> LENGTH: 373
<212> TYPE: DNA
<213> ORGANISM: Torulaspora delbrueckii
<220> FEATURE:
<221> NAME/KEY: modified_base
<222> LOCATION: (103)..(103)
<223> OTHER INFORMATION: a, c, t, g, unknown or other

<400> SEQUENCE: 19
ccattaagaa gaaattctat atgaatgaag ttagaggacg tctaaagata ctgtaagaga   60
ggatctggtt caagaccagc gcttaattgc gcggttgcgg ctnggttcgc cttttgcgga  120
acatgtcttt tctcgttgtt aactctactt caacttctac aacactgtgg agttttctac  180 acaactttc ttctttggga agatacgtct tgtgcgtgct cccagaggt gacaaacaca   240 aacaactttt tattattata aaccagtcaa aaccaatttc gttatgaaat taaaaatatt  300
taaaactttc aacaacggat ctcttggttc tcgcatcgat gaagaacgca gcctgtctct  360
tatacacatc tcc                                                     373

<210> SEQ ID NO 20
<211> LENGTH: 123
<212> TYPE: DNA

<213> ORGANISM: Cutaneotrichosporon moniliiforme

<400> SEQUENCE: 20

```
gtgaattgct ctctgagcgt taaactatat ccatctacac ctgtgaactg ttgattgact    60
tcggtcgaat tacttttaca aacattgtgt aatgaacgtc atgttattat aacaaaaaat   120
aac                                                                123
```

<210> SEQ ID NO 21
<211> LENGTH: 177
<212> TYPE: DNA
<213> ORGANISM: Unknown
<220> FEATURE:
<223> OTHER INFORMATION: Description of Unknown:
      Cutaneotrichosporon or Trichosporon sequence

<400> SEQUENCE: 21

```
tcgtaacaag gtttccgtag gtgaacctgc ggaaggatca ttagtgaatt gctctctgag    60
cgttaaacta tatccatcta cacctgtgaa ctgttgattg acttcggtca attacttttta  120
caaacattgt gtaatgaacg tcatgttatt ataacaaaaa taactttcaa caacgga      177
```

<210> SEQ ID NO 22
<211> LENGTH: 228
<212> TYPE: DNA
<213> ORGANISM: Pseudomonas sp.

<400> SEQUENCE: 22

```
caagcgttaa tcggaattac tgggcgtaaa gcgcgcgtag gtggttcgtt aagttggatg    60
tgaaatcccc gggctcaacc tgggaactgc attcaaaact gtcgagctag agtatggtag   120
agggtggtgg aatttcctgt gtagcggtga atgcgtaga tataggaagg aacaccagtg    180
gcgaaggcga ccacctggac tgatactgac actgaggtgc gaaagcgt                228
```

<210> SEQ ID NO 23
<211> LENGTH: 251
<212> TYPE: DNA
<213> ORGANISM: Bacillus amyloliquefaciens

<400> SEQUENCE: 23

```
acgtaggtgg caagcgttgt ccggaattat tgggcgtaaa gggctcgcag gcggtttctt    60
aagtctgatg tgaaagcccc cggctcaacc ggggagggtc attggaaact ggggaacttg   120
agtgcagaag aggagagtgg aattccacgt gtagcggtga atgcgtaga gatgtggagg    180
aacaccagtg gcgaaggcga ctctctggtc tgtaactgac gctgaggagc gaaagcgtgg   240
ggagcgaaca g                                                       251
```

<210> SEQ ID NO 24
<211> LENGTH: 250
<212> TYPE: DNA
<213> ORGANISM: Gluconobacter cerinus

<400> SEQUENCE: 24

```
cgaaggggc tagcgttgct cggaatgact gggcgtaaag ggcgcgtagg cggtttatgc     60
agtcagatgt gaaatccccg gcttaacct gggaactgca tttgagacgc atagactaga   120
ggtcgagaga gggttgtgga attcccagtg tagaggtgaa attcgtagat attgggaaga   180
acaccggtgg cgaaggcggc aacctggctc gatactgacg ctgaggcgcg aaagcgtggg   240
gagcaaacag                                                         250
```

<210> SEQ ID NO 25
<211> LENGTH: 364
<212> TYPE: DNA
<213> ORGANISM: Hanseniaspora uvarum

<400> SEQUENCE: 25

```
agtcgtaaca aggtttccgt aggtgaacct gcggaaggat cattagattg aattatcatt      60
gttgctcgag ttcttgttta gatcttttac aataatgtgt atctttattg aagatgtgcg     120
cttaattgcg ctgcttcttt aaagtgtcgc agtgaaagta gtcttgcttg aatctcagtc     180
aacgctacac acattggagt tttttttactt taatttaatt ctttctgctt tgaatcgaaa    240
ggttcaaggc aaaaaacaaa cacaaacaat tttattttat tataatttttt taaactaaac    300 caaaattcct aacggaaatt ttaaaataat ttaaaacttt caacaacgga tctcttggtt     360
ctct                                                                   364
```

<210> SEQ ID NO 26
<211> LENGTH: 213
<212> TYPE: DNA
<213> ORGANISM: Bacillus velezensis

<400> SEQUENCE: 26

```
caagcgttgt ccggaattat tgggcgtaaa gggctcgcag gcggtttctt aagtctgatg      60
tgaaagcccc cggctcaacc ggggagggtc attggaaact ggggaacttg agtgcagaag     120
aggagagtgg aattccacgt gtagcggtga atgcgtaga gatgtggagg aacaccagtg     180
gcgaaggcga ctctctggtc tgtaactgac gct                                   213
```

<210> SEQ ID NO 27
<211> LENGTH: 214
<212> TYPE: DNA
<213> ORGANISM: Bacillus amyloliquefaciens
<220> FEATURE:
<221> NAME/KEY: modified_base
<222> LOCATION: (19)..(19)
<223> OTHER INFORMATION: a, c, t, g, unknown or other

<400> SEQUENCE: 27

```
caagcgttgt ccggaattnt tgggcgtaaa gggctcgcag gcggtttctt aagtctgatg      60
tgaaagcccc cggctcaacc ggggagggtc atttggaaac tggggaactt gagtgcagaa     120
gaggagagtg gaattccacg tgtagcggtg aaatgcgtag agatgtggag gaacaccagt    180
ggcgaaggcg actctctggt ctgtaactga cgct                                  214
```

<210> SEQ ID NO 28
<211> LENGTH: 214
<212> TYPE: DNA
<213> ORGANISM: Bacillus velezensis

<400> SEQUENCE: 28

```
caagcgttgt ccggaattat tgggcgtaaa gggctcgcag gcggtttctt aagtctgatg      60
tgaaagcccc cggctcaacc ggggagggtc attgtgaaac tggggaactt gagtgcagaa     120
gaggagagtg gaattccacg tgtagcggtg aaatgcgtag agatgtggag gaacaccagt    180
ggcgaaggcg actctctggt ctgtaactga cgct                                  214
```

MICROBIAL COMPOSITIONS FOR THE PREVENTION OR REDUCTION OF GROWTH OF FUNGAL PATHOGENS ON PLANTS

CROSS-REFERENCE

This application is a continuation application of International Patent Application No. PCT/US2019/017692, filed Feb. 12, 2019, which claims priority to U.S. Provisional Application No. 62/629,525, filed Feb. 12, 2018, each of which is incorporated by reference herein in its entirety.

SEQUENCE LISTING

The present application is filed with a Sequence Listing in electronic format. The Sequence Listing is provided as a file entitled 51401_701_301_SL.txt, created Jul. 31, 2020, which is 15 kilobytes in size. The information in the electronic format of the Sequence Listing is incorporated by reference in its entirety.

BIOLOGICAL DEPOSIT

The following biological material has been deposited with the Westerdijk Fungal Biodiversity Institute ("CBS") in the Netherlands, and bears the following designations, deposit numbers, and dates of deposit: *Gluconobacter cerinus*, BC18B (GICC03610, Feb. 11, 2021); and *Hanseniaspora uvarum*, BC18Y (aka BC18A) (GICC03611, Feb. 11, 2021). The deposits were made in accordance with the provisions of the Budapest Treaty for the International Recognition of the Deposit of Microorganisms for the Purpose of Patent Procedure. The strains were tested by the CBS and determined to be viable.

BACKGROUND

Fungal pathogens cause significant agricultural loss, leading to loss of crops, food waste and economic loss. Microbes having anti-fungal properties have been developed as biological control agents to reduce both crop loss and food spoilage by these fungal pathogens. Commercially available products may not show the desired plant or fungal specificity or effectiveness. Furthermore, there are limited options for post-harvest protection of produce, particularly organic produce. Biocontrol compositions to prevent fungal growth can provide alternatives to currently available products.

SUMMARY

Described herein, in certain embodiments, are biocontrol compositions comprising: (i) at least one microbe, and (ii) a carrier; wherein the at least one microbe has a 16S rRNA sequence greater than 99% identical to a 16S rRNA sequence selected from the group of SEQ ID NO: 1 and SEQ ID NO: 9 or wherein the at least one microbe has an ITS sequence greater than 99% identical to an ITS sequence selected from the group of SEQ ID NO: 17 and SEQ ID NO: 20 or wherein the at least one microbe has an ITS sequence greater than 90% identical to an ITS sequence of SEQ ID NO:18. Further described herein, in certain embodiments, are biocontrol compositions comprising: (i) at least one microbe, and (ii) a carrier; wherein the at least one microbe comprises a rRNA sequence greater than 99% identical to a sequence of greater than 200 bases, the sequence comprising a rRNA sequence selected from the group consisting of SEQ ID NO: 1 and SEQ ID NO: 9 or wherein the at least one microbe has an ITS sequence greater than 99% identical to an ITS sequence of SEQ ID NO: 17 or wherein the at least one microbe has an ITS sequence greater than 90% identical to SEQ ID NO: 18. Further described herein, in certain embodiments, are biocontrol compositions, comprising: (i) at least one microbe, and (ii) a carrier, wherein the biocontrol composition is capable of inhibiting growth of *Fusarium oxysporum* 25% or more relative to a control not exposed to the biocontrol composition, or inhibiting growth of *Verticillium dahliae* 60% or more relative to a control not exposed to the biocontrol composition as determined by measuring survival of *Fusarium oxysporum* or *Verticillium dahliae*, respectively. Further descried herein, in certain embodiments, are biocontrol compositions comprising (i) at least one microbe, and (ii) a carrier, wherein the at least one microbe has a 16S rRNA sequence greater than 99% identical to a 16S rRNA sequence of SEQ ID NO: 22. Further descried herein, in certain embodiments, are biocontrol compositions comprising (i) at least one microbe, and (ii) a carrier, wherein the at least one microbe has a 16S rRNA sequence greater than 99% identical to a 16S rRNA sequence of SEQ ID NO: 23. Further described herein, in certain embodiments, are biocontrol compositions comprising (i) at least one microbe, and (ii) a carrier, wherein the at least one microbe has a 16S rRNA sequence greater than 99% identical to a 16S rRNA sequence selected from the group of SEQ ID NO: 24 or wherein the at least one microbe has an ITS sequence greater than 99% identical to an ITS sequence selected from the group of SEQ ID NO: 25 or wherein the at least one microbe has an ITS sequence greater than 90% identical to an ITS sequence of SEQ ID NO: 25.

Further descried herein, in certain embodiments, are biocontrol compositions comprising (i) at least one microbe, and (ii) a carrier, wherein the biocontrol composition is capable of inhibiting growth of *Botrytis cinerea* 25% or more relative to a control not exposed to the biocontrol composition. Further descried herein, in certain embodiments, are biocontrol compositions comprising (i) at least one microbe, and (ii) a carrier, wherein the biocontrol composition is capable of inhibiting growth of *Monilinia vaccinii-corymbosi* 25% or more relative to a control not exposed to the biocontrol composition. Further descried herein, in certain embodiments, are biocontrol compositions comprising (i) at least one microbe, and (ii) a carrier, wherein the biocontrol composition is capable of inhibiting growth of *Colletotrichum spaethanium* 25% or more relative to a control not exposed to the biocontrol composition. Further descried herein, in certain embodiments, are biocontrol compositions comprising (i) at least one microbe, and (ii) a carrier, wherein the biocontrol composition is capable of inhibiting growth of *Puccinia sorghi* 25% or more relative to a control not exposed to the biocontrol composition. Further descried herein, in certain embodiments, are biocontrol compositions comprising (i) at least one microbe, and (ii) a carrier, wherein the biocontrol composition is capable of inhibiting growth of *Plasmopara viticola* 25% or more relative to a control not exposed to the biocontrol composition. Further descried herein, in certain embodiments, are biocontrol compositions comprising (i) at least one microbe, and (ii) a carrier, wherein the biocontrol composition is capable of inhibiting growth of *Erysiphe necator* 25% or more relative to a control not exposed to the biocontrol composition. Further descried herein, in certain embodiments, are biocontrol compositions comprising (i) at least one microbe, and (ii) a carrier, wherein the biocontrol composition is capable of inhibiting growth of *Podasphaera*

*macularis* 25% or more relative to a control not exposed to the biocontrol composition. Further descried herein, in certain embodiments, are biocontrol compositions comprising (i) at least one microbe, and (ii) a carrier, wherein the biocontrol composition is capable of inhibiting growth of an organism in the genus *Pytium* 25% or more relative to a control not exposed to the biocontrol composition. Further descried herein, in certain embodiments, are biocontrol compositions comprising (i) at least one microbe, and (ii) a carrier, wherein the biocontrol composition is capable of inhibiting growth of a organism in the genus *Rhizopus* 25% or more relative to a control not exposed to the biocontrol composition.

Further described herein, in certain embodiments, are biocontrol compositions comprising: (i) a secondary metabolite of at least one microbe, and (ii) a carrier; wherein the at least one microbe has a ITS sequence greater than 99% identical to a ITS sequence selected from the group of SEQ ID NO: 17, SEQ ID NO: 18, SEQ ID NO: 19, SEQ ID NO: 20, SEQ ID NO: 21, and SEQ ID NO: 25. Further described herein, in certain embodiments, are biocontrol compositions comprising: (i) a secondary metabolite of at least one microbe, and (ii) a carrier; wherein the at least one microbe has a 16S rRNA sequence greater than 99% identical to a 16S rRNA sequence selected from the group of SEQ ID NO: 1, SEQ ID NO: 9, SEQ ID NO: 22, SEQ ID NO: 23, and SEQ ID NO: 24.

In one aspect, the biocontrol composition further comprises a second microbe, wherein the second microbe is not identical to the at least one microbe. The second microbe can comprise a RNA sequence that is at least 95% identical to a sequence selected from the group consisting of: SEQ ID NO: 1-25. The second microbe can comprise a 16S rRNA sequence that is at least 95% identical to a 16S rRNA sequence selected from the group consisting of: SEQ ID NO: 1, 2, 3, 4, 5, 6, 7, 8, 9, 10, 11, 12, 13, 14, 15, 16, 22, 23, and 24. The second microbe can comprise an internal transcribed spacer (ITS) sequence that is at least 95% identical to an ITS sequence selected from the group consisting of: SEQ ID NO: 17, 18, 19, 20, 21, and 25. The second microbe can comprise a 16S rRNA sequence that is at least 99% identical to a 16S rRNA sequence selected from the group consisting of: SEQ ID NO: 1, 2, 3, 4, 5, 6, 7, 8, 9, 10, 11, 12, 13, 14, 15, 16, 22, 23, and 24. The second microbe can comprise an internal transcribed spacer (ITS) sequence that is at least 99% identical to an ITS sequence selected from the group consisting of: SEQ ID NO: 17, 18, 19, 20, 21, and 25. The second microbe can comprise a 16S rRNA sequence that is a 16S rRNA sequence selected from the group consisting of: SEQ ID NO: 1, 2, 3, 4, 5, 6, 7, 8, 9, 10, 11, 12, 13, 14, 15, 16, 22, 23, and 24. The second microbe can comprise an internal transcribed spacer (ITS) sequence that is an ITS sequence selected from the group consisting of: SEQ ID NO: 17, 18, 19, 20, 21, and 25.

In some embodiments, the at least microbe comprises a 16S rRNA sequence that is at least 99% identical to SEQ ID NO: 24 and the second microbe comprises an ITS sequence that is at least 99% identical to SEQ ID: NO 25.

In one aspect, the biocontrol composition further comprises a third microbe, and the third microbe is not identical to either the second or the at least one microbe. In some embodiments, the at least one microbe comprises a 16S rRNA sequence greater than 99% identical to SEQ ID: 23, the second microbe comprises a 16S rRNA sequence greater than 99% identical to SEQ ID: 23, and the third microbe comprises a 16S rRNA sequence greater than 99% identical to SEQ ID: 23. In one aspect, the biocontrol composition further comprises a fourth microbe, and the third microbe is not identical to any of the third, the second or the at least one microbe. In one aspect, the biocontrol composition further comprises a fifth microbe, and the fifth microbe is not identical to any of the fourth, the third, the second or the at least one microbe. Any of the microbes in the biocontrol composition may be isolated and purified microbes. A biocontrol composition as disclosed herein may comprise one or more isolated and purified microbe. A biocontrol composition as disclosed herein may comprise one or more, two or more, three or more, four or more, or five or more isolated and purified microbes. In some instances, the biocontrol composition may comprise different strains of isolated and purified microbes that are from a single microbe species.

The at least one microbe can have an ITS sequence greater than 90% identical to SEQ ID NO: 18 and wherein the second microbe is a *Gluconacetobacter* species. The *Gluconacetobacter* species can be *Gluconacetobacter liquefaciens*. The *Gluconacetobacter* species can have a 16S rRNA sequence selected from the group consisting of: SEQ ID NO: 2, SEQ ID NO: 4, SEQ ID NO: 5, SEQ ID NO: 11, SEQ ID NO: 12, SEQ ID NO: 13, SEQ ID NO: 14, and SEQ ID NO: 16.

In one aspect, the secondary metabolite of the at least one microbe is isolated from a supernatant of a culture of the at least one microbe. The secondary metabolite of at least one microbe can comprise a lipopeptide. The lipopeptide can be a cyclic lipopeptide selected from the group consisting of: a surfactin, a fengycin, and an iturin. The secondary metabolite of at least one microbe can comprise a polyketide. The secondary metabolite of at least one microbe can comprise a volatile antifungal compound.

In one aspect, the control is exposed to *Bacillus subtilis* strain QST 713. In one aspect, the at least one microbe is isolated and purified. In one aspect, the biocontrol composition is a liquid or a powder. In one aspect, the biocontrol composition comprises a spore.

Described herein, in certain embodiments, are methods of preventing or reducing the growth of a fungal pathogen on a plant, the roots, a seed, the soil or furrow into which the seed is added, or a produce thereof, comprising: applying to the plant, the roots, the seed, the soil or furrow into which the seed or plant is added, or the produce the biocontrol described herein, wherein the biocontrol composition has anti-fungal activity. Further described herein, in certain embodiments, are methods of preventing or reducing the growth of a fungal pathogen on a plant, a seed, a root, soil or furrow into which the seed or plant is added, or a produce thereof, comprising: applying to the soil the biocontrol composition described herein, wherein the biocontrol composition has anti-fungal activity. Further described herein, in certain embodiments, are methods of preventing or reducing the growth of a fungal pathogen on a produce, comprising: spraying or otherwise treating the produce prior to harvest with the biocontrol composition described herein, wherein the biocontrol composition has anti-fungal activity. Further described herein, in certain embodiments, are methods of preventing or reducing the growth of a fungal pathogen on a produce, comprising: spraying, dipping or otherwise treating the produce with the biocontrol composition described herein, wherein the biocontrol composition has anti-fungal activity. Further described herein, in certain embodiments, are methods of preventing or reducing the growth of a fungal pathogen on a produce, comprising: applying to a packaging material used to transport or store the produce the biocontrol composition described herein, wherein the biocontrol composition has anti-fungal activity. Further described herein, in certain embodiments, are methods of preventing or reducing the growth of a fungal pathogen on a seed or a produce, comprising: integrating the biocontrol composition described herein into a process selected from the group consisting of: washing the produce or the seed, coating the produce or the seed, and a combination thereof.

In one aspect, the plant, seed, or produce thereof is a plant or produce thereof in the family Rosaceae. The plant, seed, or produce thereof in the family Rosaceae can be in the genus of: *Rubus*, *Malus*, *Pyrus*, *Cydonia*, *Prunus*, *Rosa* or *Fragaria*. The plant, the seed, or the produce thereof in the genus *Rubus* can be a raspberry or blackberrry. The plant, the seed, or the produce thereof in the genus *Fragaria* can be a strawberry. The plant, the seed, or the produce thereof in the genus *Pyrus* can be a pear. The plant, the seed, or the produce thereof in the genus *Cydonia* can be a quince. The plant, the seed, or the produce thereof in the genus *Prunus* can be an almond, a peach, a plum, an apricot, a cherry or a sloe. The plant, the seed, or the produce thereof in the genus Rosa can be a rose. The plant, the seed, or the produce thereof is in the genus *Malus* can be an apple.

In one aspect, the plant, seed, or produce thereof is a plant or produce thereof in the family Ericaceae. The plant, the seed, or the produce thereof is a plant, a seed, or a produce thereof in the family Ericaceae can be in the genus of *Vaccinium*. The plant, the seed, or the produce thereof in the genus of *Vaccinium* can be a blueberry.

In one aspect, the plant, seed, or produce thereof is a plant or produce thereof in the family Vitaceae. The plant, the seed, or the produce thereof is a plant, a seed, or a produce thereof in the family Vitaceae can be in the genus of *Vitis* The plant, the seed, or the produce thereof in the genus of *Vitis* can be a grape.

In one aspect, applying the biocontrol composition comprises dusting, dipping, rolling, injecting, rubbing, spraying, or brushing the plant, seed, or the produce with the biocontrol composition. Applying the biocontrol composition to the plant can comprise adding the biocontrol composition to a drip line, an irrigation system, a chemigation system, a spray, or a dip.

Applying the biocontrol composition to the plant can comprise applying the biocontrol composition to a root of the plant. Application to the root can be indirect. The biocontrol composition can be applied to the produce after the produce has been removed from the plant. In one aspect, the applying does not kill the plant. In one aspect, the method further comprises applying to the plant a fertilizer, an herbicide, a pesticide, or a combination thereof. The fertilizer, herbicide, or pesticide can be applied before, after, or simultaneously with the biocontrol composition.

In one aspect, the packaging material comprises: polyethylene terephthalate (PET), molded fiber, oriented polystyrene (OPS), polystyrene (PS) foam, polypropylene (PP), or a combination thereof. Applying to a packaging material can comprise washing or impregnating the packaging material.

In one aspect, the anti-fungal activity is prevention of growth of the fungal pathogen for at least 1, 2, 3, 4, 5, 6, 7, 8, 9, 10, 11, 12, 13, 14, 15, 16, 17, 18, 19 or 20 days. The anti-fungal activity can be reduced growth of the fungal pathogen on the plant, the seed, or the produce thereof relative to growth of the fungal pathogen on a control that is a plant, a seed, or a produce thereof in the family Rosaceae not exposed to the biocontrol composition. The growth of the fungal pathogen can be reduced for at least 1, 2, 3, 4, 5, 6, 7, 8, 9, 10, 11, 12, 13, 14, 15, 16, 17, 18, 19 or 20 days after exposure of the fungal pathogen to the biocontrol composition relative to growth of the fungal pathogen on the plant, seed, or produce thereof not exposed to the biocontrol composition. In one aspect, the biocontrol composition has anti-fungal activity against a filamentous or non-filamentous fungal pathogen. The filamentous or non-filamentous fungal pathogen can be selected from the group consisting of: *Albugo candida, Albugo occidentalis, Alternaria alternata, Alternaria cucumerina, Alternaria dauci, Alternaria solani Alternaria tenuis, Alternaria tenuissima, Alternaria tomatophila, Aphanomyces euteiches, Aphanomyces raphani, Armillaria mellea, Botrydia theobromae, Botrytis cinerea, Botrytinia fuckeliana, Bremia lactuca, Cercospora beticola, Cercosporella rubi, Cladosporium herbarum, Colletotrichum acutatum, Colletotrichum gloeosporioides, Colletotrichum lindemuthianum, Colletotrichum musae, Colletotrichum spaethanium, Cordana musae, Corynespora cassiicola, Daktulosphaira vitifoliae, Didymella bryoniae, Elsinoe ampelina, Elsinoe mangiferae, Elsinoe veneta, Erysiphe cichoracearum, Erysiphe necator, Eutypa lata, Fusarium oxysporum, Fusarium solani, Ganoderma boninense, Guignardia bidwellii, Gymnoconia peckiana, Helminthosporium solani, Leptosphaeria coniothyrium, Leptosphaeria maculans, Leveillula taurica, Macrophomina phaseolina, Microsphaera alni, Monilinia fructicola, Monilinia vaccinii-corymbosi, Mycosphaerella angulate, Mycosphaerella brassicicola, Mycosphaerella fragariae, Mycosphaerella fijiensis, Oidopsis taurica, Passalora fulva, Peronospora sparse, Peronospora farinosa, Phoma exigua, Phomopsis obscurans, Phomopsis vaccinia, Phomopsis viticola, Phytophthora capsica, Phytophthora erythroseptica, Phytophthora infestans, Phytophthora parasitica, Plasmopara viticola, Plasmodiophora brassicae, Podosphaera macularis, Polyscytalum pustulans, Pseudocercospora vitis, Puccinia allii, Puccinia sorghi, Pucciniastrum vaccinia, Pythium debaryanum, Pythium sulcatum, Pythium ultimum, Ralstonia solanacearum, Ramularia tulasneii, Rhizoctonia solani, Rhizopus arrhizus, Rhizopus stolomferz, Sclerotinia minor, Sclerotinia sclerotiorum, Sclerotium cepivorum, Sclerotium rolfsii, Sclerotinia minor, Sclerotinia sclerotiorum, Septoria apiicola, Septoria lactucae, Septoria lycopersici, Septoria petroelini, Sphaceloma perseae, Sphaerotheca macularis, Spongospora subterrannea, Stemphylium vesicarium, Synchytrium endobioticum, Thielaviopsis basicola, Uncinula necator, Uromyces appendiculatus, Uromyces betae, Verticillium albo-atrum, Verticillium dahliae, Verticillium theobromae*, and any combination thereof. The filamentous fungal pathogen can be selected from the group consisting of: *Fusarium oxysporum, Verticillium dahlia, Botrytis cinerea, Colletotrichum spaethaniu, Erysiphe necator, Podosphaera macularis, Monilinia vaccinii-corymbosi, Puccinia sorghi* and any combination thereof. The plant, the seed, or the produce thereof can be selected from the group consisting of: almond, apricot, apple, artichoke, banana, barley, beet, blackberry, blueberry, broccoli, Brussels sprout, cabbage, cannabis, capsicum, carrot, celery, chard, cherry, citrus, corn, cucurbit, date, fig, garlic, grape, herb, spice, kale, lettuce, oil palm, olive, onion, pea, pear, peach, peanut, papaya, parsnip, pecan, persimmon, plum, pomegranate, potato, quince, radish, raspberry, rose, rice, sloe, sorghum, soybean, spinach, strawberry, sweet potato, tobacco, tomato, turnip greens, walnut, and wheat.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIG. 5A illustrates fungal growth on a control infected with *Botrytis cinerea*. FIG. 5B illustrates fungal growth on an uninfected control. FIG. 5C illustrates fungal growth on raspberries infected with *Botrytis cinerea* and to which the supernatant from a culture of product candidate BC8 (*Bacillus amyloliquefaciens*; strain 28B) has been applied.

FIG. 6 illustrates a nucleotide alignment of the 16S RNA sequence of the BC8 strain and two *B. velezensis* FZB42 isolates.

31B illustrates the percent disease index of powdery mildew in treated and untreated raspberry leaves.

Figure 32A:
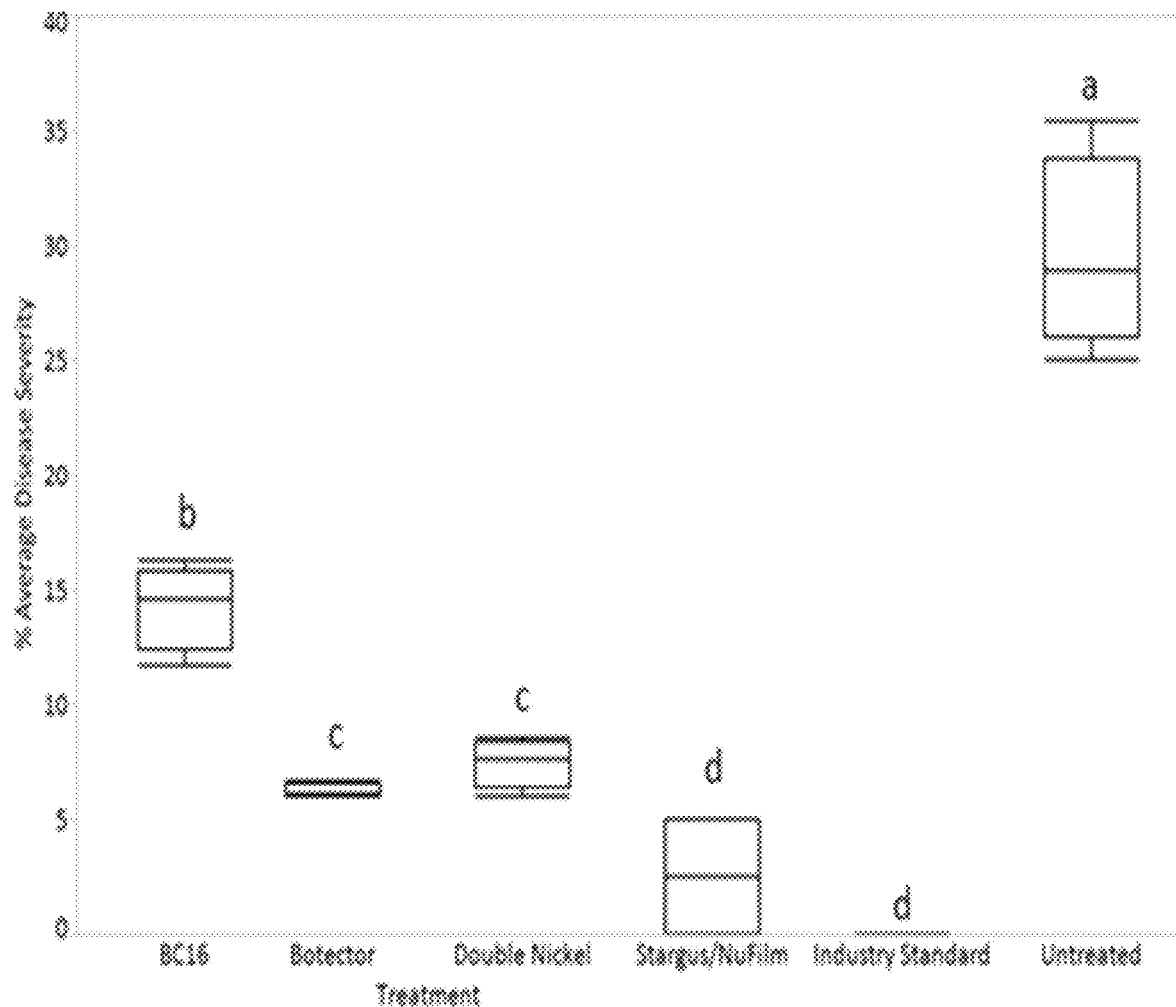
Figure 32B:
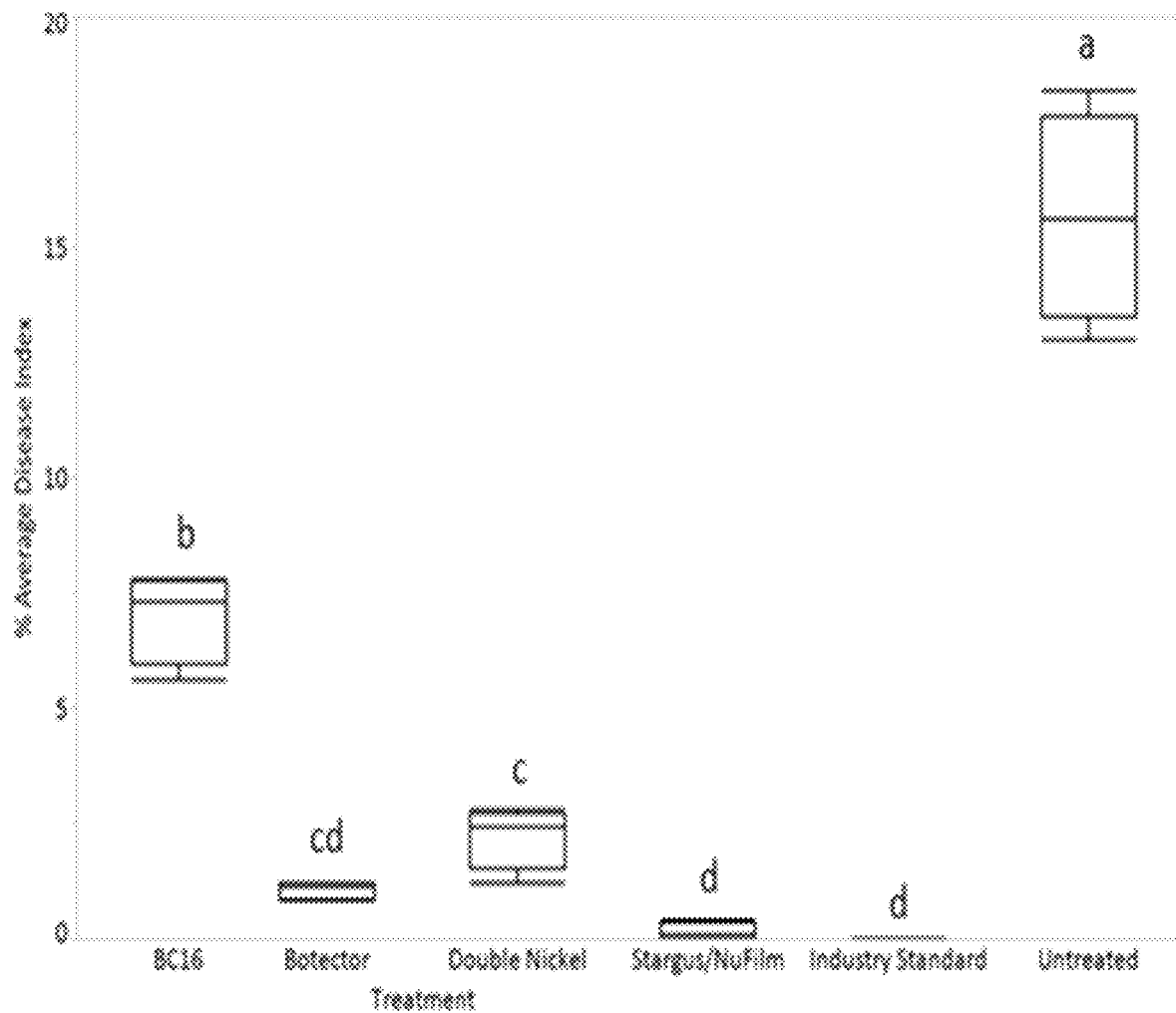

FIG. 32A illustrates the percent disease severity of powdery mildew in treated and untreated raspberries. FIG. 32B illustrates the percent disease index of powdery mildew in treated and untreated raspberries.

Figure 33A:
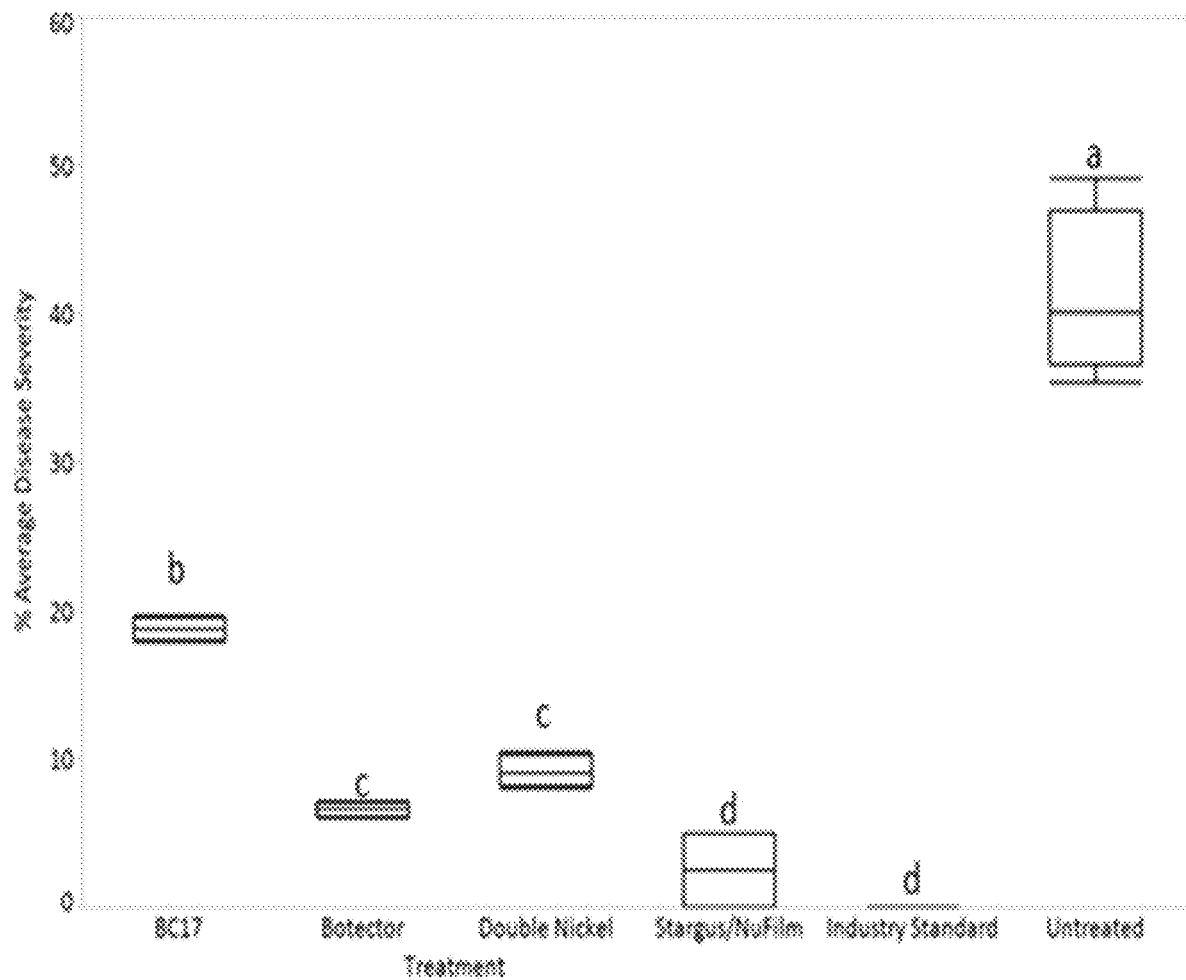
Figure 33B:
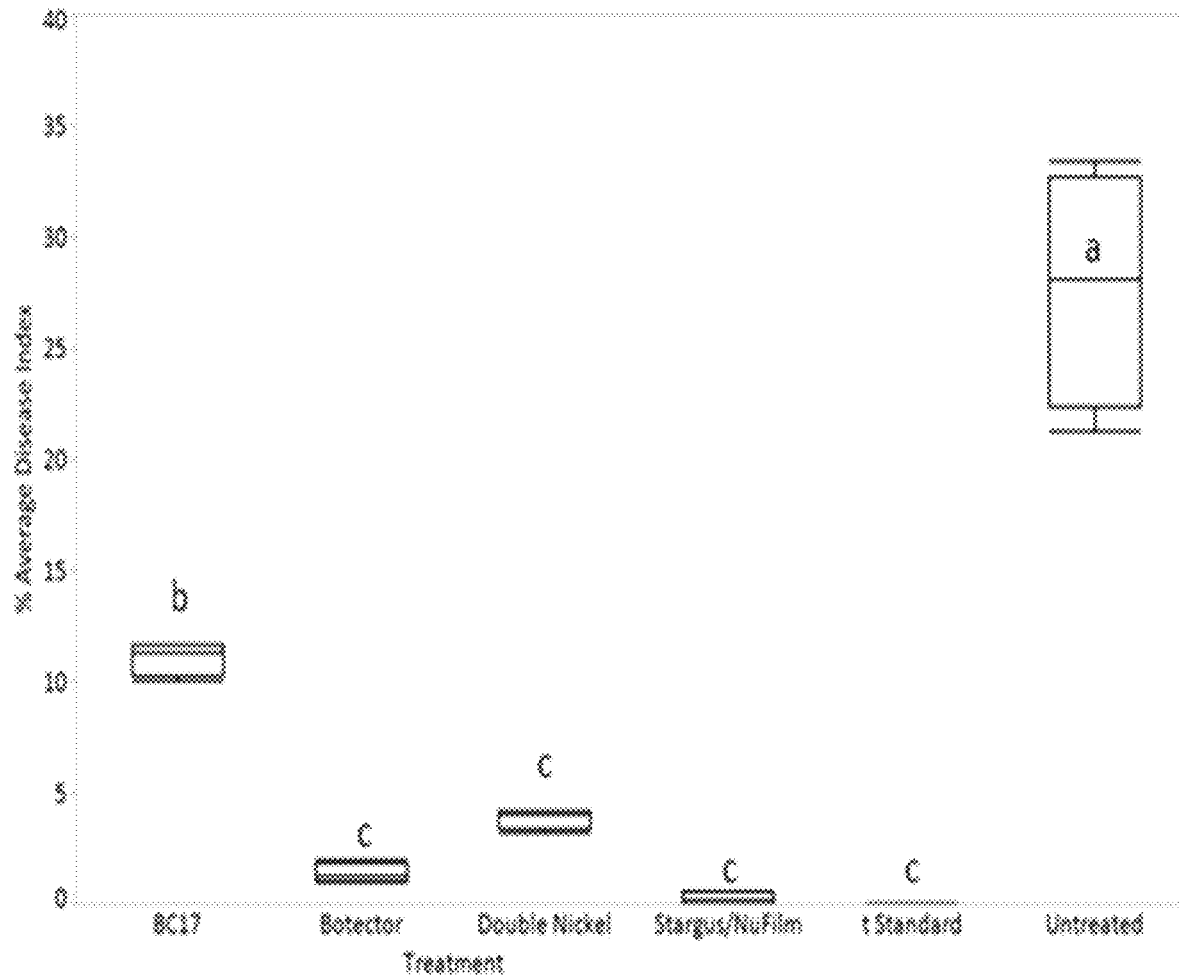

FIG. 33A illustrates the percent average disease severity of *Botrytis* in treated and untreated raspberry bushes. FIG. 33B illustrates the percent average disease index of *Botrytis* in treated and untreated raspberry bushes.

Figure 34A:
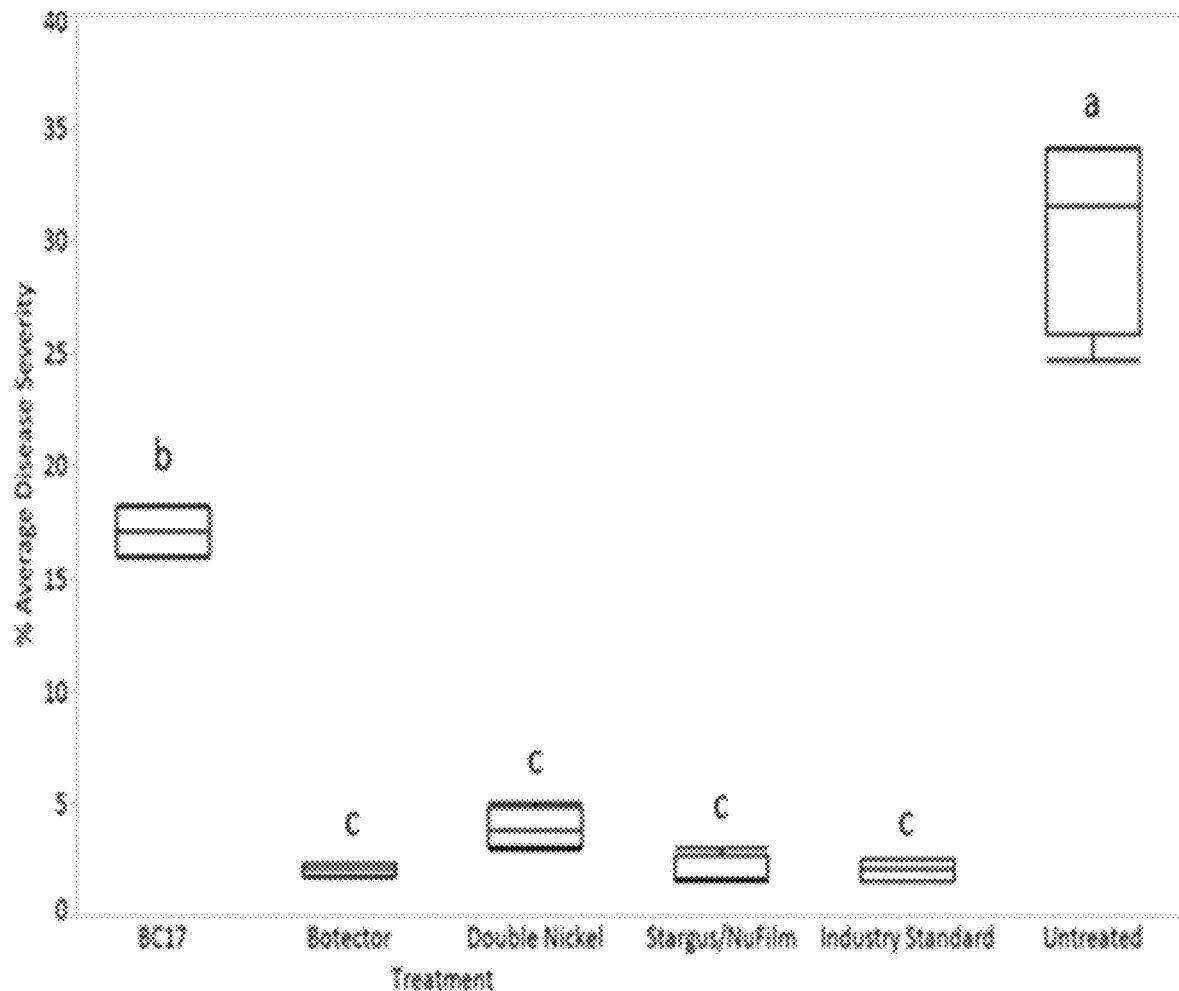
Figure 34B:
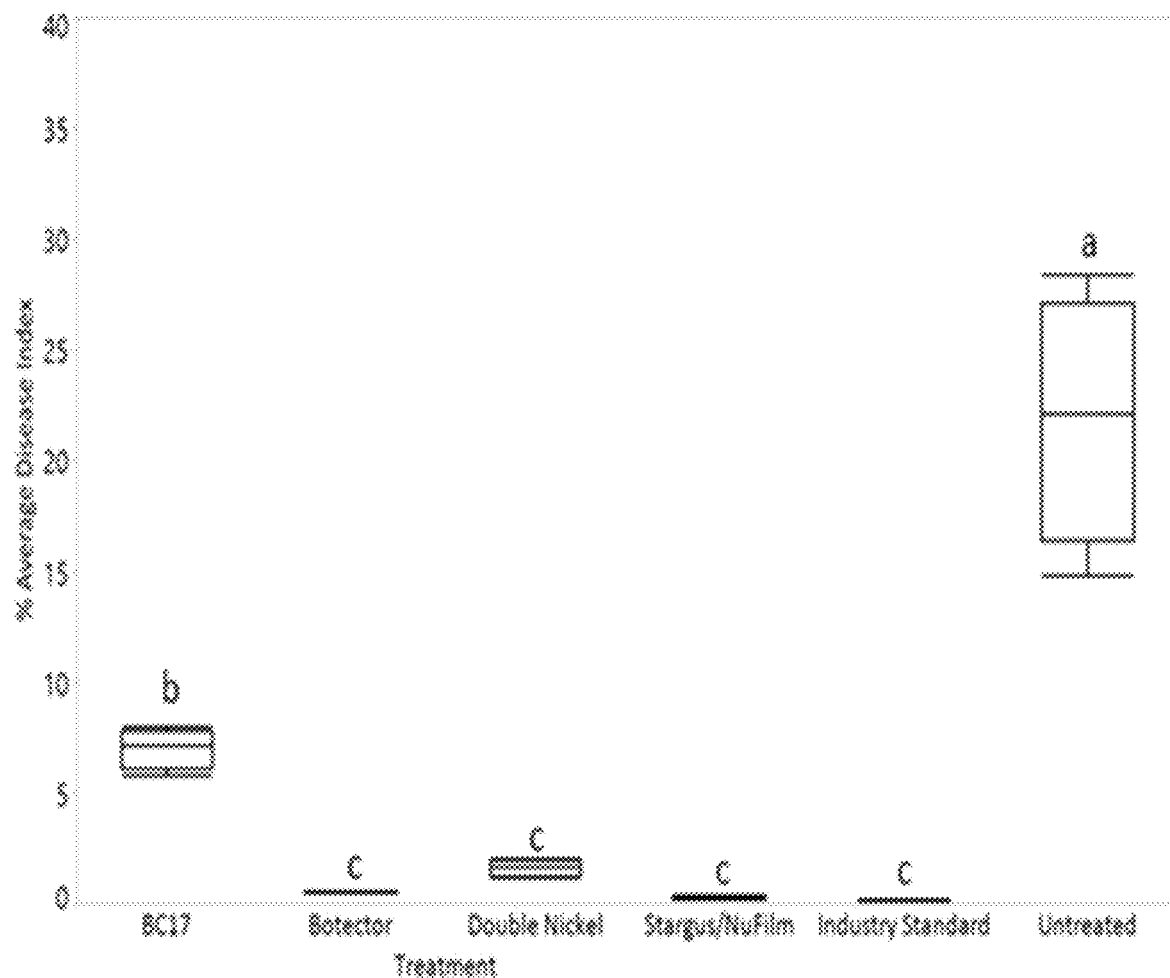

FIG. 34A illustrates the percent disease severity of powdery mildew in treated and untreated raspberry leaves. FIG. 34B illustrates the percent disease index of powdery mildew in treated and untreated raspberry leaves.

Figure 35A:
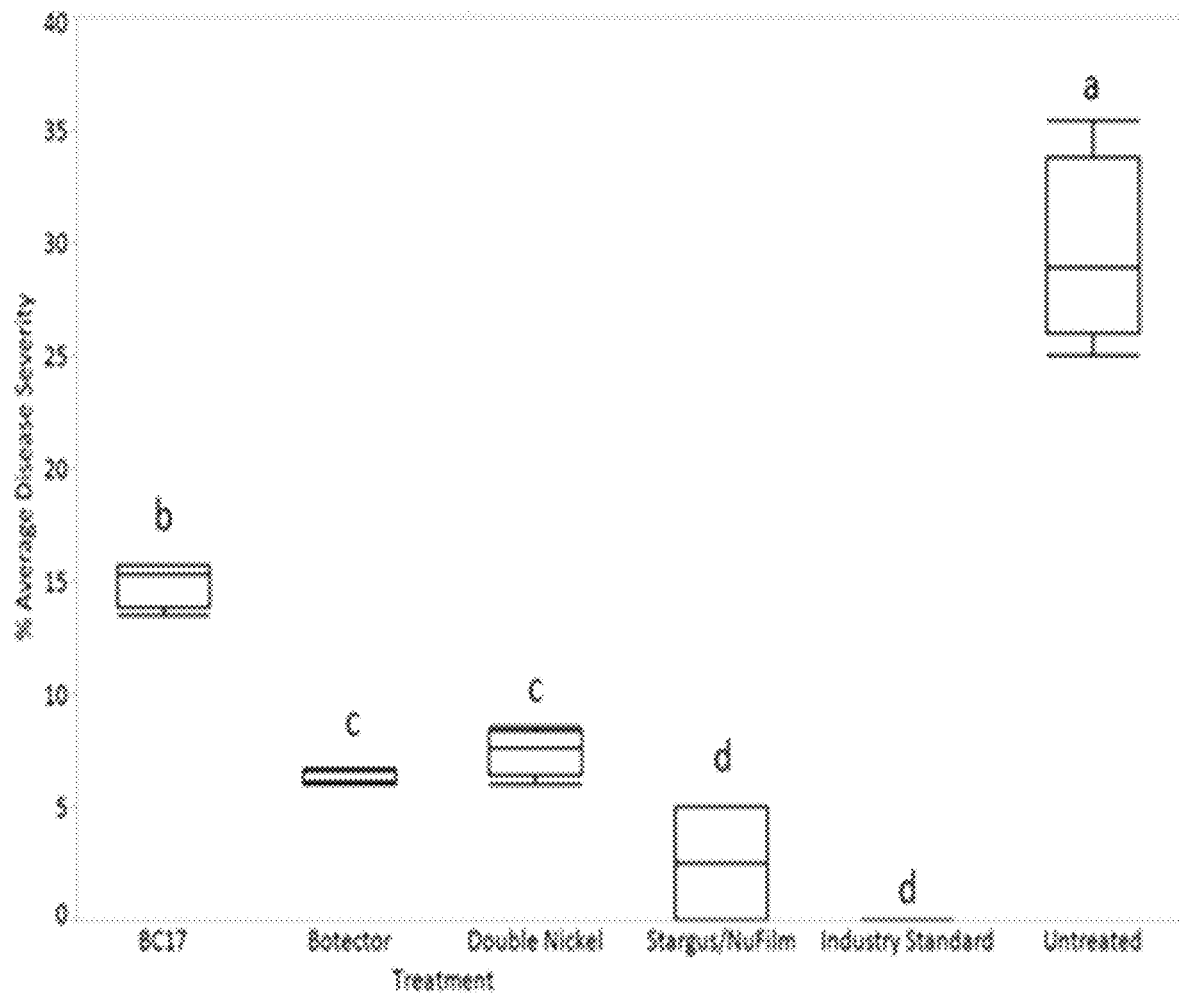
Figure 35B:
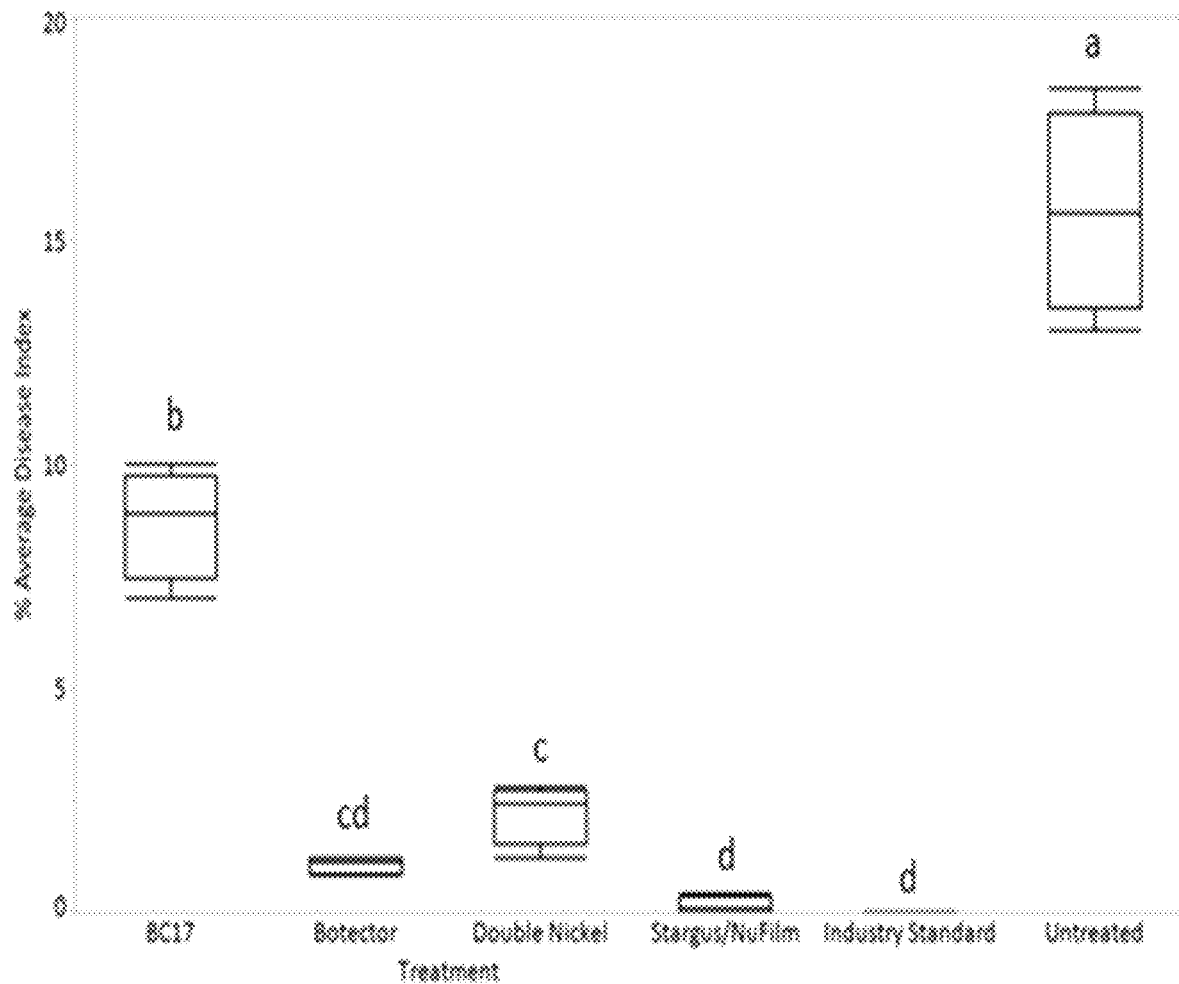

FIG. 35A illustrates the percent disease severity of powdery mildew in treated and untreated raspberries. FIG. 35B illustrates the percent disease index of powdery mildew in treated and untreated raspberries.

Figure 36:
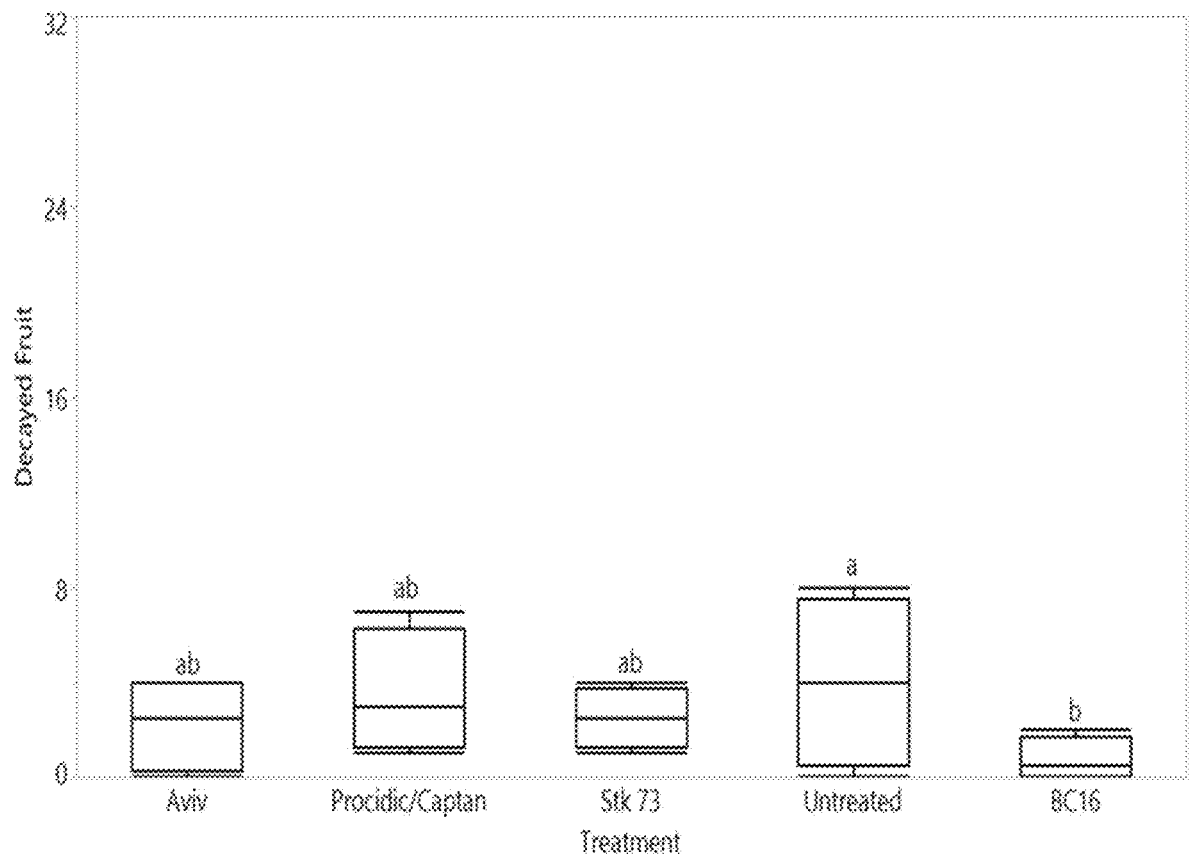

FIG. 36 illustrate the number of decayed strawberries infected by *Botrytis* and *Rhizopus* in treated and untreated plants.

Figure 37:
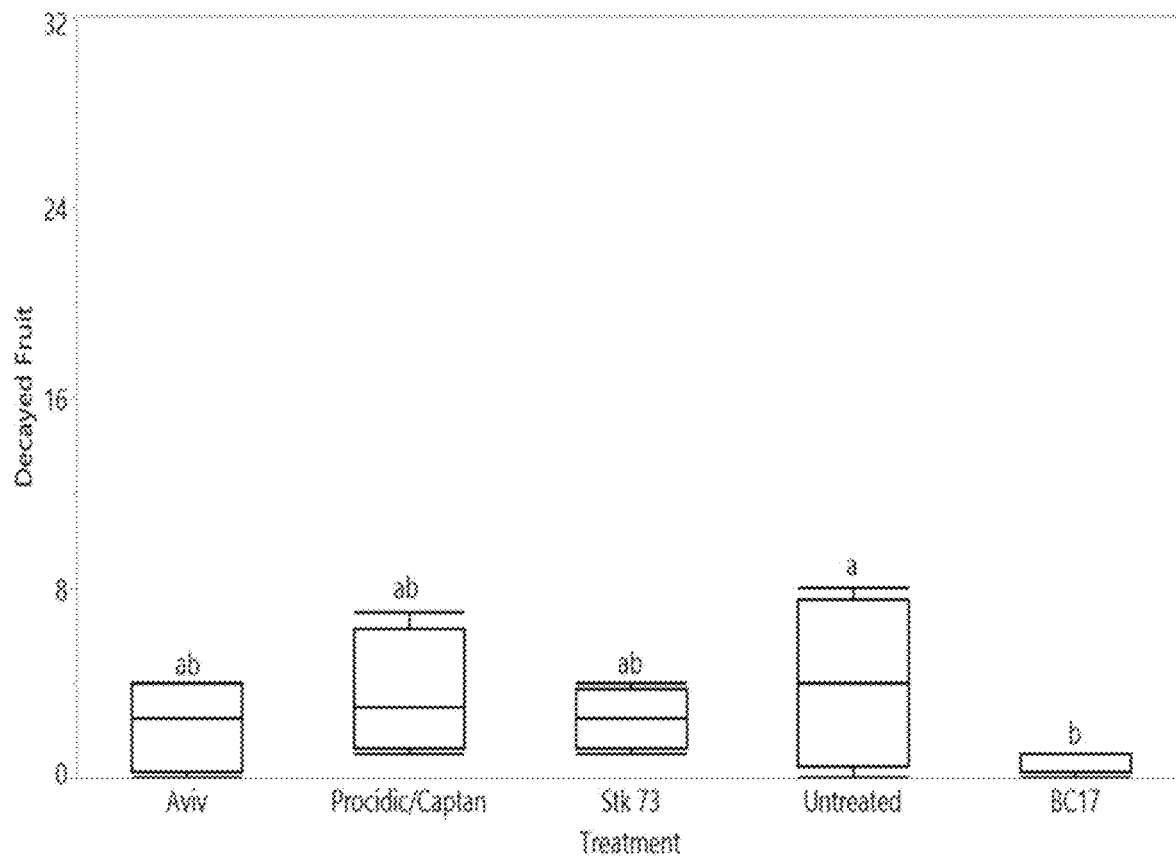

FIG. 37 illustrate the number of decayed strawberries infected by *Botrytis* and *Rhizopus* in treated and untreated plants.

Figure 38:
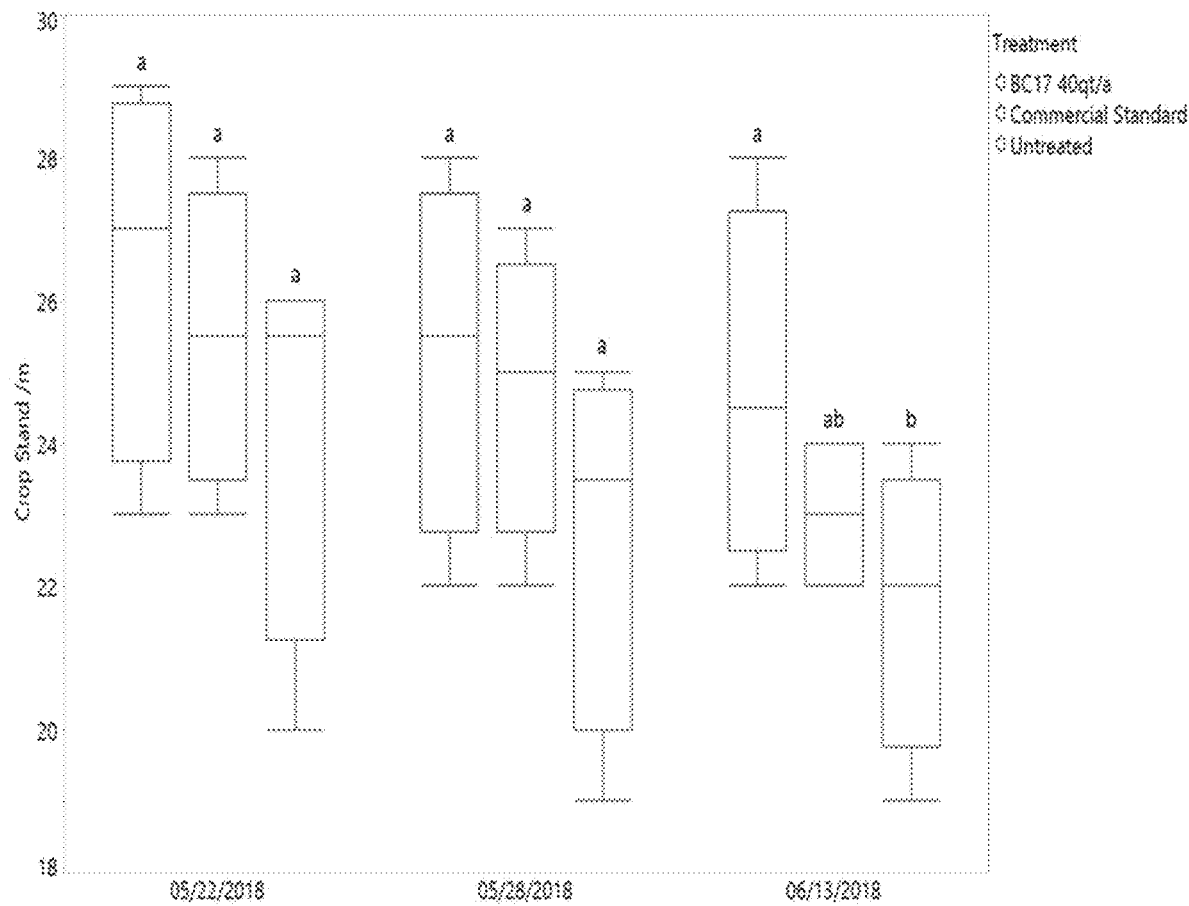

FIG. 38 illustrate the crop stand per meter of soybean plants infected by *Pythium* in treated and untreated plants.

Figure 39:
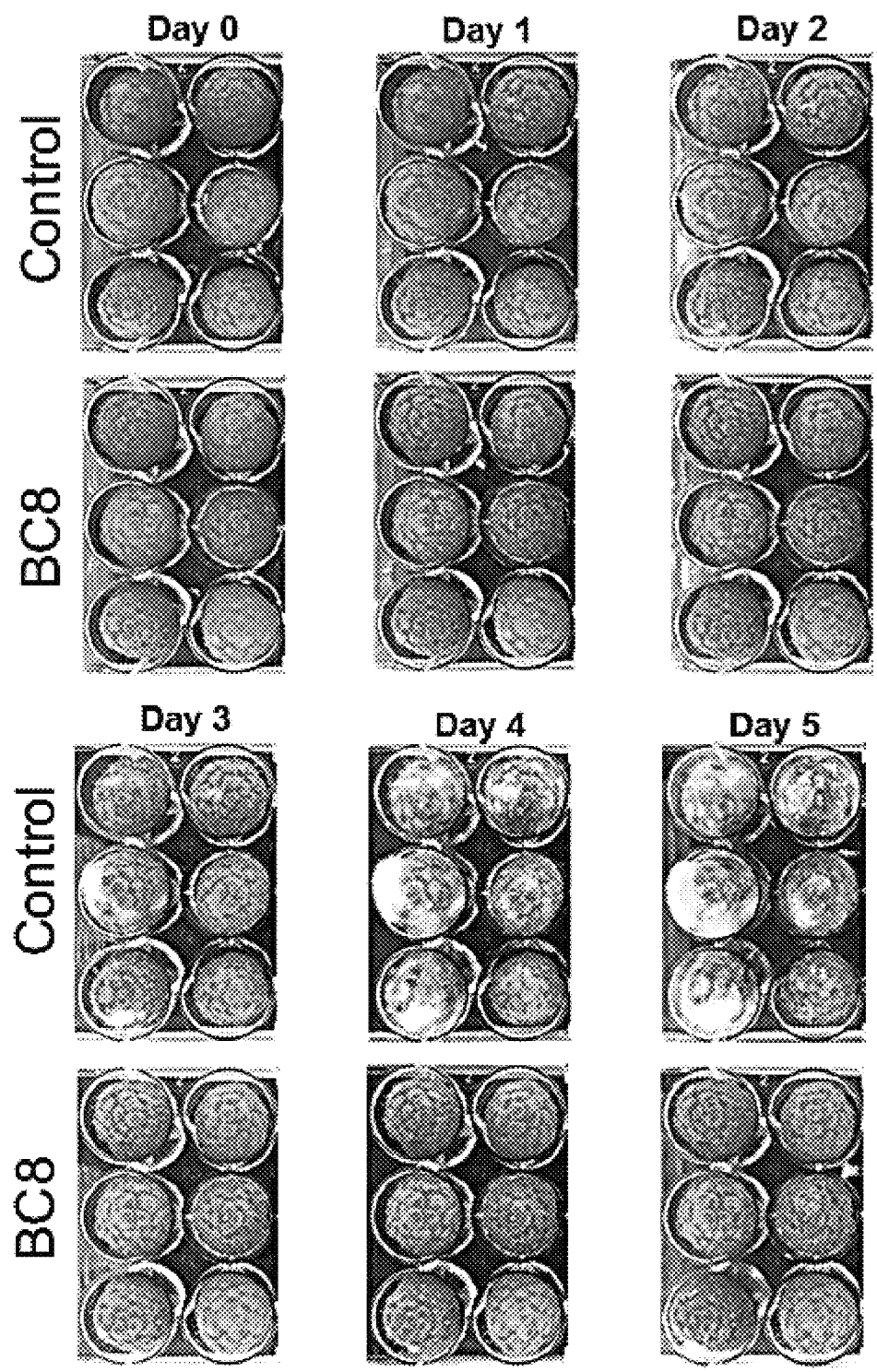

FIG. 39 illustrates treated and untreated raspberries which have been infected with *Botrytis cinerea*.

Figure 40:
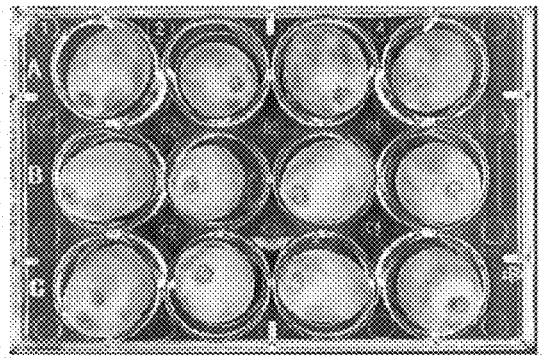
Figure 40:
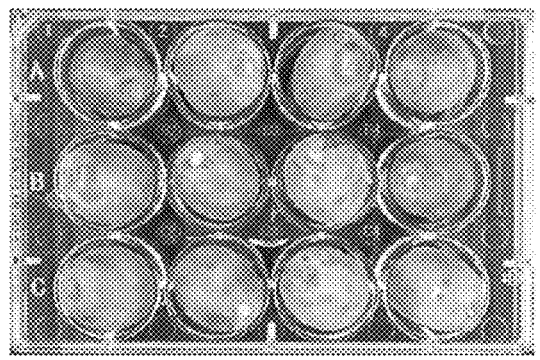
Figure 40:
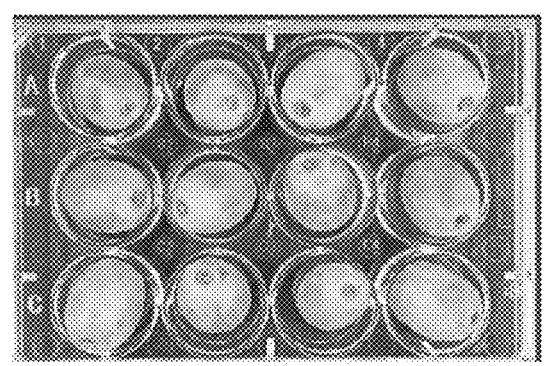

FIG. 40 illustrates treated and untreated grapes which have been infected with *Botrytis cinerea*.

Figure 41:
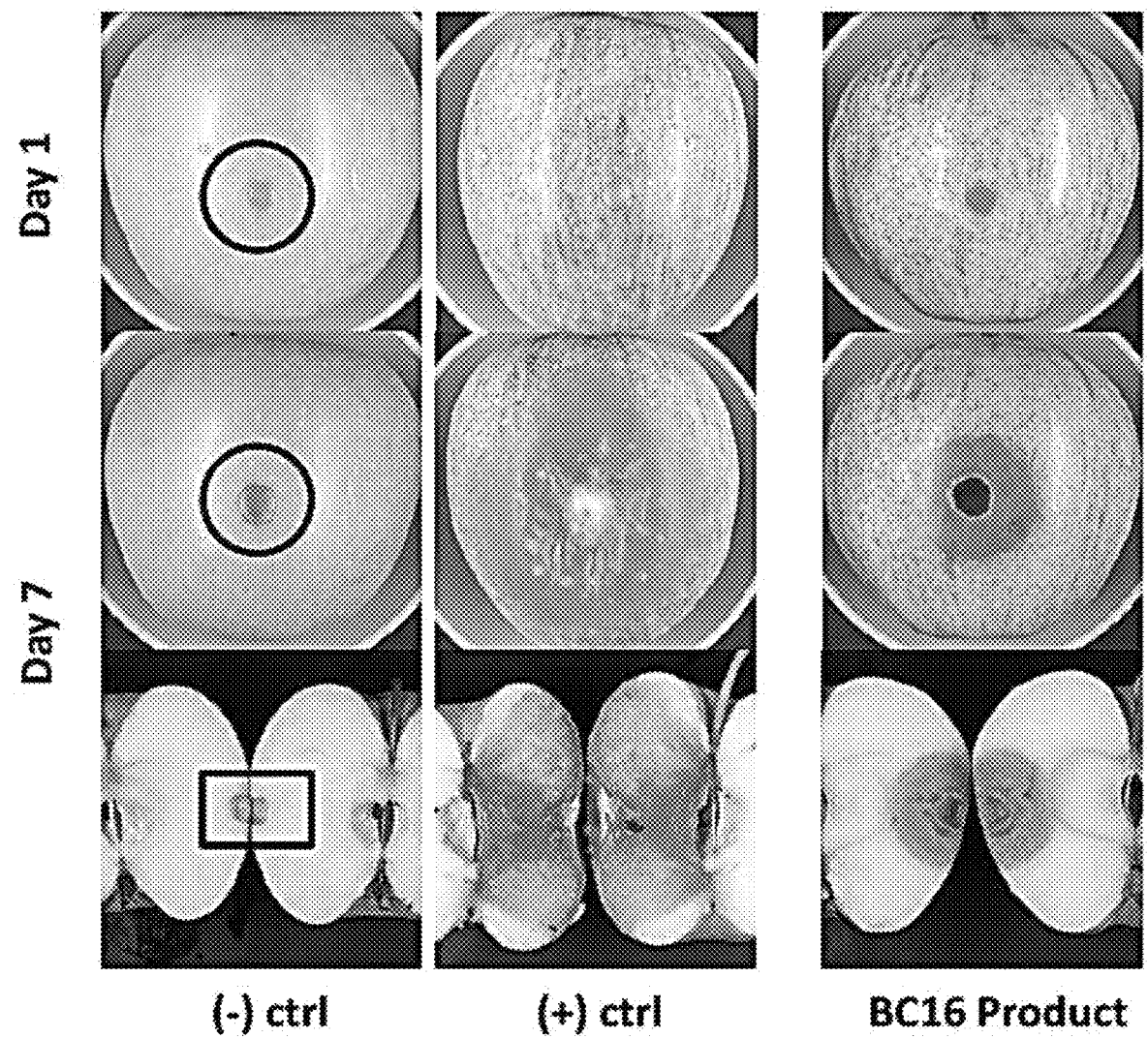

FIG. 41 illustrates treated and untreated apples which have been infected with *Botrytis cinerea*.

Figure 42:
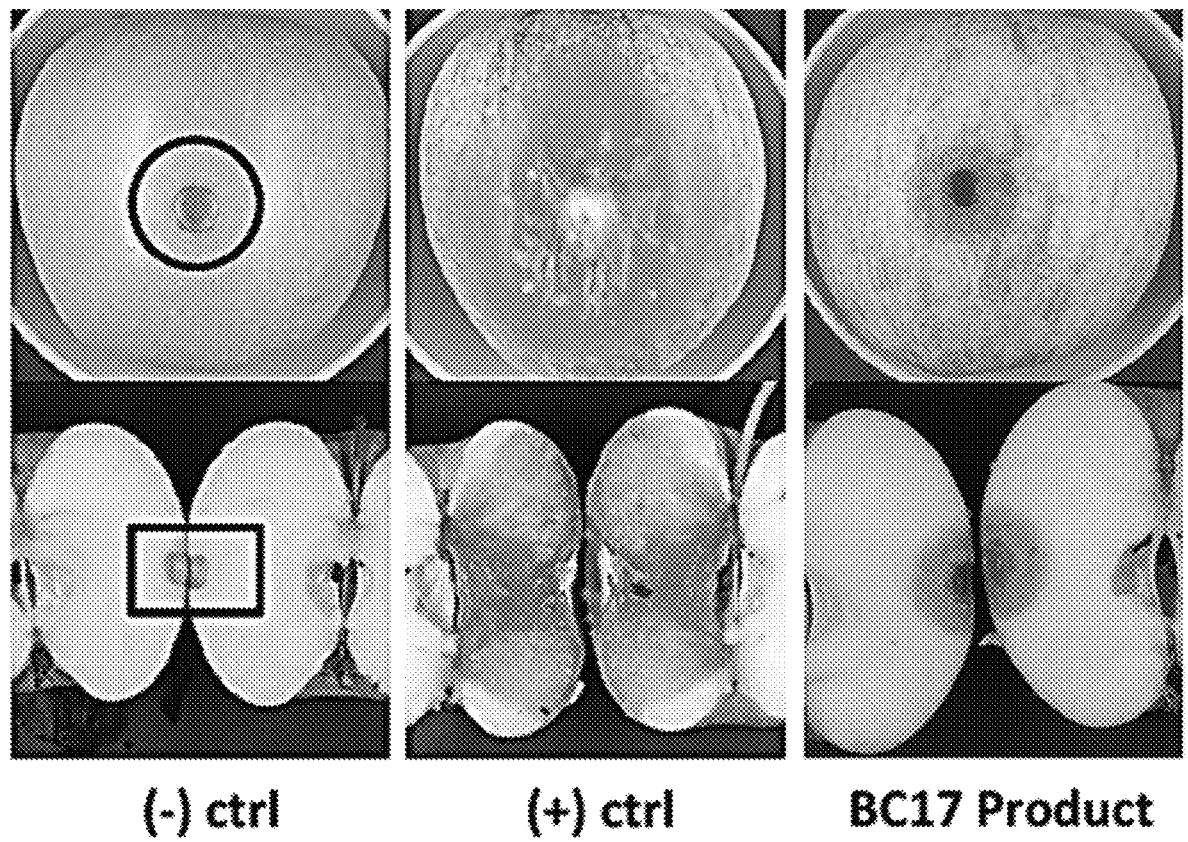

FIG. 42 illustrates treated apples which have been infected with *Botrytis cinerea*.

Figure 43:
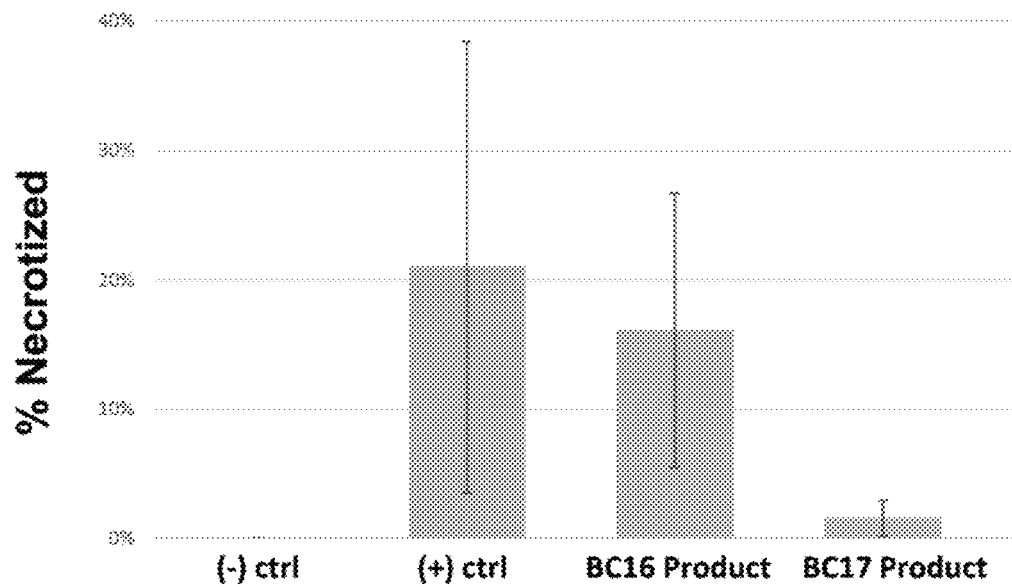

FIG. 43 illustrates the percentage of the apple that was necrotized in treated and untreated apples which have been infected with *Botrytis cinerea*.

Figure 44:
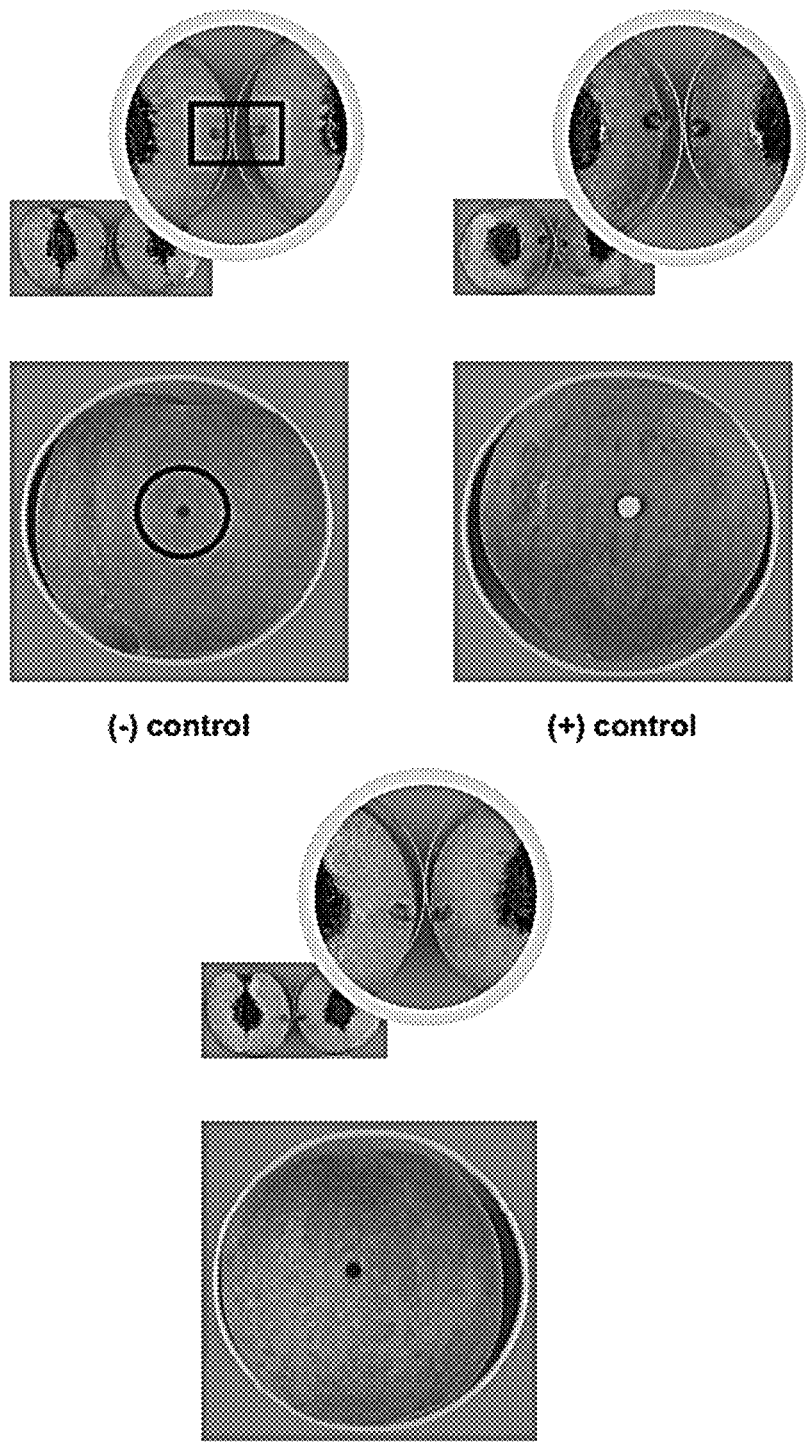

FIG. 44 illustrates treated and untreated peaches which have been infected with *Botrytis cinerea*.

DETAILED DESCRIPTION

Numerous fungal pathogens can infect plants of agricultural importance, resulting in food rot and food spoilage while the plants are in the field or after being harvested. For example, Grey Mold, caused by the fungal pathogen *Botrytis cinerea*, can often be found on fruits, such as strawberries and raspberries, both in the field and at the grocery store. Finding ways to reduce loss caused by fungal pathogens is highly desirable by anyone involved in food production and consumption, and chemical and biological based control strategies have previously been developed. However, the use of chemical- and biological-based fungicides on food crops, while effective, can provide unintended side effects (e.g., toxicity) in addition to being undesirable from a consumer standpoint. Additionally, currently available commercial biocontrol compositions may not provide the desired pathogen or plant specificity or efficacy. Finally, there may be significant burden on recording and reporting applications of synthetic chemical pesticides that is burdensome to farmers and growers.

The biocontrol compositions described herein can have anti-fungal activity against fungi of agricultural importance and can be formulated to be used at various points in the production process. For example, these biocontrol compositions can be formulated for use prior to harvest, such as for example incorporating the composition into an irrigation line or administration in combination with a fertilizer, as well as post-harvest during processing, packaging, transportation, storage, and commercial display of the produce, such as for example spraying the harvested produce with the composition or application of the composition to a packaging material used to store or ship the produce. Furthermore, these biocontrol compositions can show improved efficacy when compared to commercial biocontrol compositions.

As used herein, the term "disease severity index" generally refers to a score representing the degree of disease symptoms visible on the plant. For example, a given disease severity index may have a particular number (or range of numbers) of spots on the leaves indicative of a disease. For example, a plant that has more symptoms of the disease has a higher disease severity index than a plant that has a lower disease severity index. Different species of plants may have a different disease severity index associated with it.

As used herein, the term "disease severity" or "average disease severity" or "percent average disease severity", generally refers to the degree of disease symptoms which is visible on a plant or population of plants. The disease severity may be calculated by the percentage of the plant that is covered by disease symptoms. The percent average disease severity may be calculated for a population using by assessing the disease severity of each plant and averaging the disease severity of each plant.

As used herein, the term "disease index", "average disease index" or "percent average disease index" generally refers to a score for a population of plants representing the degree of disease symptoms visible in a population of plants. The disease index may be calculated as the disease incidence multiplied by the disease severity. The average disease index may be calculated based on a disease severity index or score for an individual plant, number of plants with that disease severity index, the total number of plants, the maximal disease index, and the percent disease incidence in order to create a weighted average representing the average disease severity. In a non-limiting example, a general calculation of the percent average disease index may be done as a [sum (number of plants in a given score multiplied by the score)]/[(total number of plants multiplied by the maximal score)] multiplied by 100.

Compositions for the Prevention or Reduction of Crop Loss and Food Spoilage

Disclosed herein are biocontrol compositions which can prevent or reduce the growth of a fungal pathogen on a plant, a seed, or a produce thereof. The term "produce" can be used herein to refer to the edible portion of a plant, such as for example, the leaves, the stem, the seeds, the root, the flowers or the fruit. The term "plant" can be used herein to refer to any portion of the plant, such as for example the leaves, the stem, the seeds, the root, or the fruit. Preventing or reducing the growth of fungal pathogens on the plant, the seed, or the produce thereof can reduce the amount of crop loss and food spoilage prior to, during, or after harvesting the produce from the plant.

The at least one microbe can be a bacterium or a yeast. The at least one microbe can comprise a microbe from a genus selected from the group consisting of: *Bacillus, Burkholderia, Cutaneotrichosporon, Cyberlindnera, Gluconacetobacter, Gluconobacter, Hanseniaspora, Paraburkholderia, Pseudomonas, Torulaspora*, and any combination thereof.

The at least one microbe can comprise a microbe selected from the group consisting of: *Bacillus amyloliquefaciens, Bacillus subtilis, Bacillus velezensis, Cutaneotrichosporon jirovecii, Cutaneotrichosporon moniliiforme*, Cutaneotrichosporon mucoides, Cyberlindnera mrakii, Cyberlindnera saturnus, Gluconacetobacter liquefaciens, Gluconobacter cerinus, Hanseniaspora uvarum, Paraburkholderia phytofirmans, Pseudomonas fluorescens, Pseudomonas frederiksbergensis, Pseudomonas lini, Pseudomonas migulae, Torulaspora delbrueckii and any combination thereof.

The at least one microbe can be a microbe from the genus Bacillus. The at least one microbe can be a microbe from the genus Burkholderia. The at least one microbe can be a microbe from the genus Cutaneotrichosporon. The at least one microbe can be a microbe from the genus Cyberlindnera. The at least one microbe can be a microbe from the genus Gluconacetobacter. The at least one microbe can be a microbe from the genus Gluconobacter. The at least one microbe can be a microbe from the genus Hanseniaspora. The at least one microbe can be a microbe from the genus Paraburkholderia. The at least one microbe can be a microbe from the genus Pseudomonas. The at least one microbe can be a microbe from the genus Torulaspora.

The at least one microbe can be Bacillus amyloliquefaciens. The at least one microbe can be Bacillus subtilis. The at least one microbe can be Bacillus velezensis. The at least one microbe can be Cutaneotrichosporon jivrovecii. The at least one microbe can be Cutaneotrichosporon moniliiforme. The at least one microbe can be Cutaneotrichosporon mucoides. The at least one microbe can be Cyberlindnera mrakii. The at least one microbe can be Cyberlindnera saturnus. The at least one microbe can be Gluconacetobacter liquefaciens. The at least one microbe can be Gluconobacter cerinus. The at least one microbe can be Hanseniaspora uvarum. The at least one microbe can be Paraburkholderia phytofirmans. The at least one microbe can be Paraburkholderia fluroescens. The at least one microbe can be Paraburkholderia frederiksbergensis. The at least one microbe can be Pseudomonas lini. The at least one microbe can be Pseudomonas migulae. The at least one microbe can be Torulaspora delbrueckii.

The at least one microbe can comprise at least one microbe with at least about: 70%, 75%, 80%, 85%, 87%, 90%, 91%, 92%, 93%, 94%, 95%, 96%, 97%, 98%, 99%, 99.5%, or 100% sequence identity to the rRNA of a microorganism selected from the group consisting of: Bacillus amyloliquefaciens, Bacillus subtilis, Bacillus velezensis, Cutaneotrichosporon jirovecii, Cutaneotrichosporon moniliiforme, Cutaneotrichosporon mucoides, Cyberlindnera mrakii, Cyberlindnera saturnus, Gluconacetobacter liquefaciens, Gluconobacter cerinus, Hanseniaspora uvarum, Paraburkholderia phytofirmans, Pseudomonas fluorescens, Pseudomonas frederiksbergensis, Pseudomonas lini, Pseudomonas migulae, Torulaspora delbrueckii, and any combination thereof. The rRNA can be a 16S rRNA, a 23S rRNA, an internal transcribed spacer (ITS), or a combination thereof. The at least one microbe can be a combination of microbe strains from one or more microbe species.

The biocontrol composition can comprise: (i) at least one microbe or a secondary metabolite of the at least one microbe, and (ii) a carrier, and wherein the at least one microbe has a 16S rRNA sequence greater than 98% identical to a 16S rRNA sequence selected from the group of SEQ ID NO: 1 and SEQ ID NO: 9 or wherein the at least one microbe has an ITS sequence greater than 98% identical to an ITS sequence selected from the group of SEQ ID NO: 17 and SEQ ID NO: 20 or wherein the at least one microbe has an ITS sequence greater than 90% identical to an ITS sequence of SEQ ID NO: 18.

The microbe can comprise an RNA sequence with at least about: 85%, 87%, 90%, 92%, 95%, 96%, 97%, 98%, 99%, 99.5%, or 100% sequence identity to a sequence selected from the group consisting of: SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID 23, SEQ ID 24, and SEQ ID 25.

The biocontrol composition can further comprise a second microbe, wherein the second microbe is not identical to the at least one microbe. The second microbe can comprise an RNA sequence with at least about: 85%, 87%, 90%, 92%, 95%, 96%, 97%, 98%, 99%, 99.5%, or 100% sequence identity to a sequence selected from the group consisting of: SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO 23, SEQ ID NO: 24, and SEQ ID NO 25. In some cases, the first microbe and the second microbe are the same species. For example, the first microbe and the second microbe may both be Bacillus amyloliquefaciens. In a further non-limiting example, a first microbe and a second microbe, and optionally more than two microbes, each different strains of the same species, may be included in a biocontrol composition as disclosed herein. In some cases, the first microbe and second microbe are not the same species. For example, the first microbe may be Gluconobacter cerinus and the second microbe may be Hanseniaspora uvarum. In some cases, the first microbe and second microbe are not the same genus. In some cases, the first microbe and second microbe are not in the same family. In some cases, the first microbe and second microbe are not in the same order. In some cases, the first microbe and second microbe are not in the same class. In some cases, the first microbe and second microbe are not in the same phylum. In some cases, the first microbe and second microbe are not in the same kingdom.

In one embodiment, the at least one microbe comprises at least one microbe with at least about: 85%, 87%, 90%, 92%, 95%, 96%, 97%, 98%, 99%, 99.5%, or 100% sequence identity to a rRNA sequence from a Bacillus species. The Bacillus species can be Bacillus amyloliquefaciens, Bacillus subtilis, or Bacillus velezensis. The rRNA sequence can be a 16S sequence. In one embodiment, the at least one microbe comprises at least one microbe with at least about: 85%, 87%, 90%, 92%, 95%, 96%, 97%, 98%, 99%, 99.5%, or 100% sequence identity to SEQ ID NO: 1 or SEQ ID NO: 23.

In one embodiment, the at least one microbe comprises at least one microbe with at least about: 85%, 87%, 90%, 92%, 95%, 96%, 97%, 98%, 99%, 99.5%, or 100% sequence identity to a rRNA sequence from a Gluconacetobacter species. The Gluconacetobacter species can be Gluconacetobacter liquefaciens. The rRNA sequence can be a 16S sequence. In one embodiment, the at least one microbe comprises at least one microbe with at least about: 85%, 87%, 90%, 92%, 95%, 96%, 97%, 98%, 99%, 99.5%, or 100% sequence identity to SEQ ID NO: 2, SEQ ID NO: 4, SEQ ID NO: 5, SEQ IS NO: 11, SEQ ID NO: 12, SEQ ID NO: 13, SEQ ID NO: 14, or SEQ ID NO: 16.

In one embodiment, the at least one microbe comprises at least one microbe with at least about: 85%, 87%, 90%, 92%, 95%, 96%, 97%, 98%, 99%, 99.5%, or 100% sequence identity to a rRNA sequence from a *Gluconobacter* species. The *Gluconobacter* species can be *Gluconobacter cerinus*. The rRNA sequence can be a 16S sequence. In one embodiment, the at least one microbe comprises at least one microbe with at least about: 85%, 87%, 90%, 92%, 95%, 96%, 97%, 98%, 99%, 99.5%, or 100% sequence identity to SEQ ID NO: 24.

In one embodiment, the at least one microbe comprises at least one microbe with at least about: 85%, 87%, 90%, 92%, 95%, 96%, 97%, 98%, 99%, 99.5%, or 100% sequence identity to a rRNA sequence from a *Burkholderia* species or a *Paraburkholderia* species. The *Paraburkholderia* species can be *Paraburkholderia phytofirmans*. The rRNA sequence can be a 16S sequence. In one embodiment, the at least one microbe comprises at least one microbe with at least about: 85%, 87%, 90%, 92%, 95%, 96%, 97%, 98%, 99%, 99.5%, or 100% sequence identity to SEQ ID NO: 3, SEQ ID NO: 7, or SEQ ID NO: 9.

In one embodiment, the at least one microbe comprises at least one microbe with at least about: 85%, 87%, 90%, 92%, 95%, 96%, 97%, 98%, 99%, 99.5%, or 100% sequence identity to a rRNA sequence from a *Pseudomonas* species. The *Pseudomonas* species can be *Pseudomonas fluorescens, Pseudomonas lini, Pseudomonas migulae*, or *Pseudomonas frederiksbergensis*. The rRNA sequence can be a 16S sequence. In one embodiment, the at least one microbe comprises at least one microbe with at least about: 85%, 87%, 90%, 92%, 95%, 96%, 97%, 98%, 99%, 99.5%, or 100% sequence identity to SEQ ID NO: 6, SEQ ID NO: 10, SEQ ID NO: 15, or SEQ ID NO: 22.

In one embodiment, the at least one microbe comprises at least one microbe with at least about: 85%, 87%, 90%, 92%, 95%, 96%, 97%, 98%, 99%, 99.5%, or 100% sequence identity to SEQ ID NO: 8.

In one embodiment, the at least one microbe comprises at least one microbe with at least about: 85%, 87%, 90%, 92%, 95%, 96%, 97%, 98%, 99%, 99.5%, or 100% sequence identity to an rRNA sequence from a *Cyberlindnera* species. The *Cyberlindnera* species can be *Cyberlinderna saturnus* or *Cyberlindera mrakkii*. The rRNA sequence can be an ITS sequence. In one embodiment, the at least one microbe comprises at least one microbe with at least about: 85%, 87%, 90%, 92%, 95%, 96%, 97%, 98%, 99%, 99.5%, or 100% sequence identity to SEQ ID NO: 17.

In one embodiment, the at least one microbe comprises at least one microbe with at least about: 85%, 87%, 90%, 92%, 95%, 96%, 97%, 98%, 99%, 99.5%, or 100% sequence identity to an rRNA sequence from a *Hanseniaspora* species. The *Hanseniaspora* species can be *Hanseniaspora uvarum*. The rRNA sequence can be an ITS sequence. In one embodiment, the at least one microbe comprises at least one microbe with at least about: 85%, 87%, 90%, 92%, 95%, 96%, 97%, 98%, 99%, 99.5%, or 100% sequence identity to SEQ ID NO: 18 or SEQ ID: 25. In one embodiment, the at least one microbe comprises at least one microbe with at least 90% sequence identity to SEQ ID NO: 18 or SEQ ID: 25. In one embodiment, the at least one microbe comprises at least one microbe with at least 95% sequence identity to SEQ ID NO: 18 or SEQ ID: 25. In one embodiment, the at least one microbe comprises at least one microbe with at least 99% sequence identity to SEQ ID NO: 18 or SEQ ID: 25.

In one embodiment, the at least one microbe comprises at least one microbe with at least about: 85%, 87%, 90%, 92%, 95%, 96%, 97%, 98%, 99%, 99.5%, or 100% sequence identity to an rRNA sequence from a *Torulaspora* species. The *Torulaspora* species can be *Torulaspora delbrueckii*. The rRNA sequence can be an ITS sequence. In one embodiment, the at least one microbe comprises at least one microbe with at least about: 85%, 87%, 90%, 92%, 95%, 96%, 97%, 98%, 99%, 99.5%, or 100% sequence identity to SEQ ID NO: 19.

In one embodiment, the at least one microbe comprises at least one microbe with at least about: 85%, 87%, 90%, 92%, 95%, 96%, 97%, 98%, 99%, 99.5%, or 100% sequence identity to an rRNA sequence from a *Cutaneotrichosporon* species. The *Cutaneotrichosporon* species can be *Cutaneotrichosporon monilitforme, Cutaneotrichosporon jirovecii*, or *Cutaneotrichosporon mucoides*. The rRNA sequence can be an ITS sequence. In one embodiment, the at least one microbe comprises at least one microbe with at least about: 85%, 87%, 90%, 92%, 95%, 96%, 97%, 98%, 99%, 99.5%, or 100% sequence identity to SEQ ID NO: 20 or SEQ ID NO: 21.

The biocontrol composition can comprise a consortium of microbes comprising a plurality of microbes. The plurality of microbes can be at least two microbes, at least three microbes, at least four microbes, at least five microbes, at least six microbes, at least seven microbes, at least eight microbes, at least nine microbes, or at least ten microbes. Each microbe of the plurality of microbes can be a different microbe. The biocontrol composition can comprise secondary metabolites from a consortium of microbes comprising a plurality of microbes, wherein the plurality of microbes is at least two microbes, at least three microbes, at least four microbes, at least five microbes, at least six microbes, at least seven microbes, at least eight microbes, at least nine microbes, or at least ten microbes.

The at least two microbes can comprise at least two microbes selected from the group consisting of: microbes with a 16S rRNA sequence selected from the group consisting of SEQ ID SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 22, SEQ ID NO: 23, SEQ ID NO: 24 and microbes with an ITS sequence selected from the group consisting of SEQ ID NO: 17, SEQ ID NO: 18, SEQ ID NO: 19, SEQ ID NO: 20, SEQ ID NO: 21, and SEQ ID NO 25. The at least two microbes can comprise a first microbe with a 16S rRNA sequence selected from SEQ ID NO: 1 or SEQ ID NO: 9 or wherein the first microbe has an ITS sequence greater than 98% identical to an ITS sequence selected from the group of SEQ ID NO: 17 and SEQ ID NO: 20 or wherein the first microbe has an ITS sequence greater than 90% identical to an ITS sequence of SEQ ID NO: 18. The at least two microbes can comprise a first microbe having an ITS sequence greater than 90% identical to SEQ ID NO:18 and a second microbe can be a *Gluconacetobacter* species. The *Gluconacetobacter* species can be *Gluconacetobacter liquefaciens*. The *Gluconacetobacter* species can be a *Gluconacetobacter* species having a 16S rRNA sequence selected from the group consisting of: SEQ ID NO: 2, SEQ ID NO: 4, SEQ ID NO: 5, SEQ ID NO: 11, SEQ ID NO: 12, SEQ ID NO: 13, SEQ ID NO: 14, and SEQ ID NO: 16. The at least two microbes can comprise a first microbe being a *Gluconobacter* species and a second microbe being a *Hanseniaspora* species. The at least two microbes can comprise a first microbe being a *Gluconobacter cerinus* and a second microbe being a *Hanseniaspora uvarum*.

The at least two microbes can comprise a first microbe with a 16S sequence greater than 90% identical to SEQ ID NO: 24 and a second microbe with a ITS sequence greater than 90% identical to SEQ ID NO: 25. The at least two microbes can comprise a first microbe with a 16S sequence greater than 95% identical to SEQ ID NO: 24 and a second microbe with a ITS sequence greater than 95% identical to SEQ ID NO: 25. The at least two microbes can comprise a first microbe with a 16S sequence greater than 98% identical to SEQ ID NO: 24 and a second microbe with a ITS sequence greater than 98% identical to SEQ ID NO: 25.

The at least three microbes can comprise a first microbe with a with a 16S rRNA sequence greater than 99% identical to SEQ ID: 23, a second microbe with a 16S rRNA sequence greater than 99% identical to SEQ ID: 23, a third microbe with 16S rRNA sequence greater than 99% identical to SEQ ID: 23, wherein the first microbe, second microbe, and third microbe comprise genomes that are not identical. In some cases, the genomes may differ by a single nucleotide polymorphism (SNP). In some cases the genomes may differ by more than one SNPs. In some cases, the genomes may differ by the number of the genes in each genome. In some cases, the genomes may differ by rearrangements, such as insertions, deletions, reordering, refactoring or lysogenic or inactive phage, insertion sequences, repetitive genomic sequence or other differing contents of genomic regions or genes. In some cases, the cellular DNA content may differ by the inclusion of one or more plasmids, which may differ from strain to strain. In some case, the genomes may code for different isoforms of the genes. For example, an expressed protein from the gene may contain a point mutation, a deletion, an insertion, which may affect the function of the protein. For example, an expressed protein from the gene may contain a point mutation, a deletion, an insertion, which may not affect the function of the protein, or which may not substantially affect the function of the protein.

The at least three microbes can comprise at least three microbes selected from the group consisting of microbes with a 16S rRNA sequence selected from the group consisting of microbes with a 16S rRNA sequence selected from the group consisting of SEQ ID SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 22, SEQ ID NO: 23, and SEQ ID NO:24 and microbes with an ITS sequence selected from the group consisting of SEQ ID NO: 17, SEQ ID NO: 18, SEQ ID NO: 19, SEQ ID NO: 20, SEQ ID NO: 21, and SEQ ID NO: 25. The at least three microbes can comprise at least one microbe with a 16S rRNA sequence selected from SEQ ID NO: 1, SEQ ID NO: 9, or SEQ ID 23 or an ITS sequence selected from SEQ ID NO: 17, SEQ ID NO: 18, or SEQ ID NO:20.

The at least four microbes can comprise at least four microbes selected from the group consisting of microbes with a 16S rRNA sequence selected from the group consisting of microbes with a 16S rRNA sequence selected from the group consisting of SEQ ID SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 22, SEQ ID NO: 23, and SEQ ID NO:24 and microbes with an ITS sequence selected from the group consisting of SEQ ID NO: 17, SEQ ID NO: 18, SEQ ID NO: 19, SEQ ID NO: 20, SEQ ID NO: 21, and SEQ ID NO: 25. The at least four microbes can comprise at least one microbe with a 16S rRNA sequence selected from SEQ ID NO: 1 SEQ ID NO: 9 or SEQ ID NO:23 or an ITS sequence selected from SEQ ID NO: 17, SEQ ID NO: 18, or SEQ ID NO:20.

The at least five microbes can comprise at least five microbes selected from the group consisting of microbes with a 16S rRNA sequence selected from the group consisting of microbes with a 16S rRNA sequence selected from the group consisting of SEQ ID SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 22, SEQ ID NO: 23, and SEQ ID NO:24 and microbes with an ITS sequence selected from the group consisting of SEQ ID NO: 17, SEQ ID NO: 18, SEQ ID NO: 19, SEQ ID NO: 20, SEQ ID NO: 21, and SEQ ID NO: 25. The at least five microbes can comprise at least one microbe with a 16S rRNA sequence selected from SEQ ID NO: 1 SEQ ID NO: 9 or SEQ ID 23 or an ITS sequence selected from SEQ ID NO: 17, SEQ ID NO: 18, or SEQ ID NO: 20.

Figure 2:
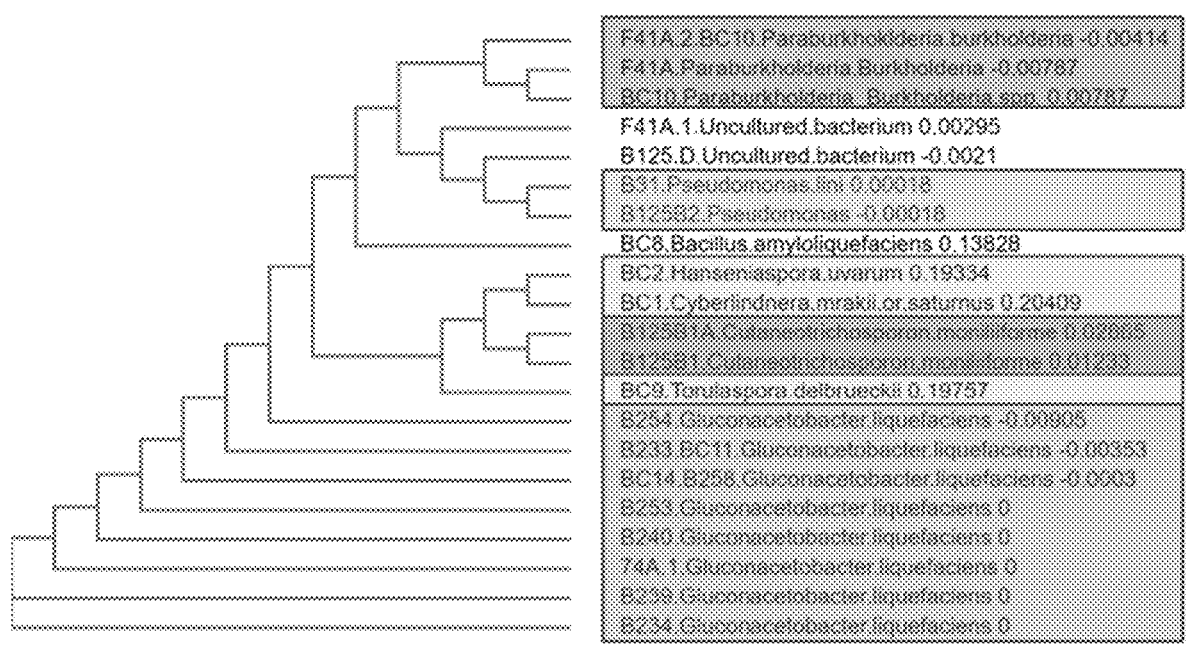
FIG. 2 illustrates phylogenetic relationships between 16S and ITS sequences in Table 1.

Table 1 illustrates the microbial strain identifiers, putative microbial genus or species, and corresponding SEQ ID NOs described herein. The at least one microbe can be a microbe in Table 1. Phylogenetic relationships of some of these strains are indicated in FIG. 2. Table 2 illustrates the sequences corresponding to these SEQ ID NOs.

TABLE 1

Microbial strains with anti-fungal activity

| Microbial strain identifier(s) | Putative microbial genus or species | SEQ ID NO. | 16S or ITS |
| --- | --- | --- | --- |
| 28B; BC8 | *Bacillus amyloliquefaciens* | SEQ ID NO: 1 | 16S |
| 74A.1; BC12 | *Gluconacetobacter liquefaciens* | SEQ ID NO: 2 | 16S |
| 41A2 | *Paraburkholderia* or *Burkholderia* | SEQ ID NO: 3 | 16S |
| 253A; B253 | *Gluconacetobacter liquefaciens* | SEQ ID NO: 4 | 16S |
| 254A; B254; BC13 | *Gluconacetobacter liquefaciens* | SEQ ID NO: 5 | 16S |
| B125.D, 125B | *Pseudomonas fluorescens* | SEQ ID NO: 6 | 16S |
| 41A; F41A | *Paraburkholderia* or *Burkholderia* | SEQ ID NO: 7 | 16S |
| 41A.1; F41A.1 | Unknown | SEQ ID NO: 8 | 16S |
| 41A.2; F41A.2; BC10 | *Paraburkholderia* or *Burkholderia* | SEQ ID NO: 9 | 16S |
| B31 | *Pseudomonas lini* | SEQ ID NO: 10 | 16S |
| 233B; BC11 | *Gluconacetobacter liquefaciens* | SEQ ID NO: 11 | 16S |
| 234B; B234 | *Gluconacetobacter liquefaciens* | SEQ ID NO: 12 | 16S |
| 239B; B239 | *Gluconacetobacter liquefaciens* | SEQ ID NO: 13 | 16S |
| B240; BC15 | *Gluconacetobacter liquefaciens* | SEQ ID NO: 14 | 16S |
| B125B2; B125.B2 | *Pseudomonas* sp. | SEQ ID NO: 15 | 16S |

TABLE 1-continued

Microbial strains with anti-fungal activity

| Microbial strain identifier(s) | Putative microbial genus or species | SEQ ID NO. | 16S or ITS |
|---|---|---|---|
| 258B; BCM | Gluconacetobacter liquefaciens | SEQ ID NO: 16 | 16S |
| 1C; BC1 | Cyberlindnera mrakii or Cyberlindnera saturnus | SEQ ID NO: 17 | ITS |
| 74.2; BC2 | Hanseniaspora uvarum | SEQ ID NO: 18 | ITS |
| 74.3; BC9 | Torulaspora delbrueckii | SEQ ID NO: 19 | ITS |
| 125B; B125B1A | Cutaneotrichosporon moniliiforme | SEQ ID NO: 20 | ITS |
| 125B.1; B125B1 | Cutaneotrichosporon or Trichosporon | SEQ ID NO: 21 | ITS |
| BC16 | Pseudomonas sp. | SEQ ID NO: 22 | 16S |
| BC17 | Bacillus amyloliquefaciens | SEQ ID NO: 23 | 16S |
| BC18 | Gluconobacter cerinus | SEQ ID NO: 24 | 16S |
| BC18 | Hanseniaspora uvarum | SEQ ID NO: 25 | ITS |

TABLE 2

Sequences

| SEQ ID NO | Sequence |
|---|---|
| SEQ ID NO: 1 | CAAGCGTTGTCCGGAATTNTTGGGCGTAAAGGGCTNCG CAGGCGGTTTNCTTAAGTCTGATGTGAAAGCCCCCGGC TCAACCGGGGAGGGTCATTTGGAAACTGGGGAACTTGA GTGCAGAAGAGGAGAGTGGAATTCCACGTGTAGCGGTG AAATGCGTAGAGATGTGGAGGAACACCAGTGGCGAAG GCGACTCTCTGGTCTGTAACTGACGCT |
| SEQ ID NO: 2 | CGGAATGAGTGGGCGTAAAGGGCGCGTAGGCGGTATGG ACAGTCAGATGTGAAATTCCTGGGCTTAACCTGGGGGC TGCATTTGATACGTCCAAAACTAGAGTGTGAGAGAGGG TTGTGGAATTCCCAGTGTAGAGGTGAAATTCGTAGATA TTGGGAAGAACACCGGTGGCGAAGGCGGCAACCTGGCT CATAACTGACGCTGA |
| SEQ ID NO: 3 | CGTTAATCGGAATTACTGGGCGTAAAGCGTGCGCAGGC GGTTCGCTAAGACAGATGTGAAATCCCCGGGCTTAACC TGGGAACTGCATTTGTGACTGGCGGGCTAGAGTATGGC AGAGGGGGTAGAATTCCACGTGTAGCAGTGAAATGCG TAGAGATGTGGAGGAATACCGATGGCGAAGGCAGCCCC CTGGGCCAATACTGACGCTCATGCA |
| SEQ ID NO: 4 | AAGGGGGCTAGCGTTGCTCGGAATGACTGGGCGTAAAG GCGCGTAGGCGGTATGGACAGTCAGATGTGAAATTCC TGGGCTTAACCTGGGGCTGCATTTGATACGTCCAAAC TAGAGTGTGAGAGAGGGTTGTGGAATTCCCAGTGTAGA GGTGAAATTCGTAGATATTGGGAAGAACACCGGTGGCG AAGGCGGCAACCTGGCTCATAACTGACGCTGAGGCGCG AAAGCGTGG |
| SEQ ID NO: 5 | GAAGGGGGCTAGCGTTGCTCGGAATGACTGGGCGTAAA GGGCGCGTAGGCGGTATGGACAGTCAGATGTGAAATTC CTGGGCTTAACCTGGGGGCTGCATTTGATACGTCCAAA CTAGAGTGTGAGAGAGGGTTGTGGAATTCCCAGTGTAG AGGTGAAATTCGTAGATATTGGGAAGAACACCGGTGGC GAAGGCGGCAACCTGGCTCATAACTGACGCTGAGGCGC GAAAGCGTGGGGAGCAAACAGGATTAGATACCCCGTA GTCCCTGTCTCTTATACACATCTCCGAGCCCACGAGAC A |
| SEQ ID NO: 6 | GCAAGCGTTAATCGGAATTACTGGGCGTAAAGCGCGCG TAGGTGGTTCGTTAAGTTGGATGTGAAATCCCCGGGCT CAACCTGGGAACTGCATTCAAAACTGTCGAGCTAGAGT ATGGTAGAGGGTGGTGGAATTTCCTGTGTAGCGGTGAA ATGCGTAGATATAGGAAGGAACACCAGTGGCGAAGGCA CCACCTGGACTGATACTGACACTGAGGTGCGAAAGCG TGGGGAGCAAACAGGATTAGATACCCCGTAG |
| SEQ ID NO: 7 | GTAATACGTAGGGTGCAAGCGTTAATCGGAATTACTGG GCGTAAAGCGTGCGCAGGCGGTTCGCTAAGACAGATGT GAAATCCCCGGGCTTAACCTGGGAACTGCATTTGTGAC TGGCGGGCTAGAGTATGGCAGAGGGGGTAGAATTCCA CGTGTAGCAGTGAAATGCGTAGAGATGTGGAGGAATAC CGATGGCGAAGGCAGCCCCCTGGGCCAATACTGACGCT CATGCACGAAAGCGTGGGGAGCAAACAGGATTAGATAC CCCCGTAGTCCCTGTCTCTTATACACATCTCCGAGCCC ACGAGACA |
| SEQ ID NO: 8 | GCAAGCGTTAATCGGAATTACTGGGCGTAAAGCGCGCG TAGGTGGTTTGTTAAGTTGGATGTGAAAGCCCCGGGCT CAACCTGGGAACTGCATTCAAAACTGACAAGCTAGAGT ATGGTAGAGGGTGGTGGAATTTCCTGTGTAGCGGTGAA ATGCGTAGATATAGGAAGGAACACCAGTGGCGAAGGCG ACCACCTGGACTGATACTGACACTGAGGTGCGAAAGCG TGGGGAGCAAACAGGATTAGATACCCCGTAGTCCCTG TCTCTTATACACATCTCCGAGCCCACGAGACA |
| SEQ ID NO: 9 | TGTTTTGTCGGCAGCGTCAGATGTGTATAAGAGACAGG TGTCAGCAGCCGCGGTAATACGTAGGGTGCAAGCGTTA ATCGGAATTACTGGGCGTAAAGCGTGCGCAGGNGNNTC GCTAAGACAGATGTGAAATCCCCGGGCTTAACCTGGGA ACTGCATTTGTGACTGGCGGGCTAGAGTATGGCAGAGG GGGTAGAATTCCACGTGTAGCAGTGAAATGCGTAGAG ATGTGGAGGAATACCGATGGCGAAGGCAGCCCCCTGGG CCAATACTGACGCTCATGCACGAAAGCGTGGGGAGCAA ACAGGATTAGATACCCCGGTAGTCCCTGTCTCTTATAC ACATCTCCGAGCCCACGAGACA |
| SEQ ID NO: 10 | CAAGCGTTAATCGGAATTACTGGGCGTAAAGCGCGCGT AGGTGGTTCGTTAAGTTGGATGTGAAATCCCCGGGCTC AACCTGGGAACTGCATTCAAAACTGTCGAGCTAGAGTA TGGTAGAGGGTGGTGGAATTTCCTGTGTAGCGGTGAAA TGCGTAGATATAGGAAGGAACACCAGTGGCGAAGGCGA CCACCTGGACTGATACTGACACTGAGGTGCGAAAGCGT |
| SEQ ID NO: 11 | TTGTTTCGTCGGCAGCGTCAGATGTGTATAAGAGACAG GTGTCAGCCGCCGCGGTAATACGAAGGGGGCTAGCGTT GCTCGGAATGACTGGGCGTAAAGGCGCGTAGGCGGTA TGGACAGTCAGATGTGAAATTCCTGGGCTTAACCTGGG GGCTGCATTTGATACGTCCAAACTAGAGTGTGAGAGAG GGTTGTGGAATTCCCAGTGTAGAGGTGAAATTCGTAGA TATTGGGAAGAACACCGGTGGCGAAGGCGGCAACCTGG CTCATAACTGACGCTGAGGCGNAAAGCGTGGGGAG |
| SEQ ID NO: 12 | AAGGGGGCTAGCGTTGCTCGGAATGACTGGGCGTAAAG GCGCGTAGGCGGTATGGACAGTCAGATGTGAAATTCC TGGGCTTAACCTGGGGGCTGCATTTGATACGTCCAAAC TAGAGTGTGAGAGAGGGTTGTGGAATTCCCAGTGTAGA GGTGAAATTCGTAGATATTGGGAAGAACACCGGTGGCG AAGGCGGCAACCTGGCTCATAACTGACGCTGAGGCGC |

TABLE 2-continued

Sequences

| SEQ ID NO | Sequence |
|---|---|
| SEQ ID NO: 13 | AAGGGGGCTAGCGTTGCTCGGAATGACTGGGCGTAAAG GGCGCGTAGGCGGTATGGACAGTCAGATGTGAAATTCC TGGGCTTAACCTGGGGGCTGCATTTGATACGTCCAAAC TAGAGTGTGAGAGAGGGTTGTGGAATTCCCAGTGTAGA GGTGAAATTCGTAGATATTGGGAAGAACACCGGTGGCG AAGGCGGCAACCTGGCTCATAACTGACGCTGAGGCG |
| SEQ ID NO: 14 | AAGGGGGCTAGCGTTGCTCGGAATGACTGGGCGTAAAG GGCGCGTAGGCGGTATGGACAGTCAGATGTGAAATTCC TGGGCTTAACCTGGGGGCTGCATTTGATACGTCCAAAC TAGAGTGTGAGAGAGGGTGTGGAATTCCCAGTGTAGA GGTGAAATTCGTAGATATTGGGAAGAACACCGGTGGCG AAAGGCGGCAACCTGGCTCATAACTGACGCTGAGGCGC GAAGCGT |
| SEQ ID NO: 15 | TGCAAGCGTTAATCGGAATTACTGGGCGTAAAGCGCGC GTAGGTGGTTCGTTAAGTTGGATGTGAAATCCCCGGGC TCAACCTGGGAACTGCATTCAAAACTGTCGAGCTAGAG TATGGTAGAGGGTGGTGGAATTTCCTGTGTAGCGGTGA AATGCGTAGATATAGGAAGGAACACCAGTGGCGAAGGC GACCACCTGGACTGATACTGACACTGAGGTGCGAAAGC GTGGGGAGC |
| SEQ ID NO: 16 | AGGGGGCTAGCGTTNCTCGGAATGACTGGGCGTAAAGG GCGCGTAGGCGGTATGGACAGTCAGATGTGAAATTCCT GGGCTTAACCTGGGGGCTGCATTTGATACGTCCAAACT AGAGTGTGAGAGAGGGTTGTGGAATTCCCAGTGTAGAG GTGAAATTCGTAGATATTGGGAAGAACACCGGTGGCGA AGGCGGCAACCTGGCTCATAACTGACGCTGAGGCGCGA |
| SEQ ID NO: 17 | AGGTGAACCTGCGGAAGGATCATTAAAGTATTCTTCGG TGCAGCCAGCGCTTCCACAGCGCGGCAGCCCAAACCTT CACGAAGTGGCCAAAGGTTCTTAAACACAAAAGATTTA CTATNATCTTTCAAAACTTT |
| SEQ ID NO: 18 | AATNGCGCNGCTTCTTTAGAGTGTCGCAGTAAAAGTAG TCTTGCTTGAATCTCAGTCAACGCTACACACATTCGGA GTTTTTTTATTTTATTTTATTTCTTTCGCTTTTGATTC AAGAGGTCCAGGCCAAAAACCAACCCCAACCATTTTAA TTTATTTTTAAATTATTTNAAACCTTTCA |
| SEQ ID NO: 19 | CCATTAAGAAGAAATTCTATATGAATGAAGTTAGAGGA CGTCTAAAGATACTGTAAGAGAGGATCTGGTTCAAGAC CAGCGCTTAATTGCGCGGTTGCGGCTNGGTTCGCCTTT TGCGGAACATGTCTTTTCTCGTTGTTAACTCTACTTCA ACTTCTACAACACTGTGGAGTTTTCTACACAACTTTTC TTCTTTGGGAAGATACGTCTTGTGCGTGCTTCCCAGAG GTGACAAACACAAACAACTTTTTATTATTATAAACCAG TCAA AACCAATTTCGTTATGAAATTAAAAATATTTAAAACTT TCAACAACGGATCTCTTGGTTCTCGCATCGATGAAGAA CGCAGCCTGTCTCTTATACACATCTCC |
| SEQ ID NO: 20 | GTGAATTGCTCTCTGAGCGTTAAACTATATCCATCTAC ACCTGTGAACTGTTGATTGACTTCGGTCGAATTACTTT TACAAACATTGTGTAATGAACGTCATGTTATTATAACA AAAATAAC |
| SEQ ID NO: 21 | TCGTAACAAGGTTTCCGTAGGTGAACCTGCGGAAGGAT CATTAGTGAATTGCTCTCTGAGCGTTAAACTATATCCA TCTACACCTGTGAACTGTTGATTGACTTCGGTCAATTA CTTTTACAAACATTGTGTAATGAACGTCATGTTATTAT AACAAAAATAACTTTCAACAACGGA |
| SEQ ID NO: 22 | CAAGCGTTAATCGGAATTACTGGGCGTAAAGCGCGCGT AGGTGGTTCGTTAAGTTGGATGTGAAATCCCCGGGCTC AACCTGGGAACTGCATTCAAAACTGTCGAGCTAGAGTA TGGTAGAGGGTGGTGGAATTTCCTGTGTAGCGGTGAAA TGCGTAGATATAGGAAGGAACACCAGTGGCGAAGGCGA CCACCTGGACTGATACTGACACTGAGGTGCGAAAGCGT |
| SEQ ID NO: 23 | ACGTAGGTGGCAAGCGTTGTCCGGAATTATTGGGCGTA AAGGGCTCGCAGGCGGTTTCTTAAGTCTGATGTGAAAG CCCCCGGCTCAACCGGGGAGGGTCATTGGAAACTGGGG AACTTGAGTGCAGAAGAGGAGAGTGGAATTCCACGTGT AGCGGTGAAATGCGTAGAGATGTGGAGGAACACCAGTG GCGAAGGCGACTCTCTGGTCTGTAACTGACGCTGAGGA GCGAAAGCGTGGGGAGCGAACAG |
| SEQ ID NO: 24 | CGAAGGGGCTAGCGTTGCTCGGAATGACTGGGCGTAA AGGGCGCGTAGGCGGTTTATGCAGTCAGATGTGAAATC CCCGGGCTTAACCTGGGAACTGCATTTGAGACGCATAG ACTAGAGGTCGAGAGAGGGTTGTGGAATTCCCAGTGTA GAGGTGAAATTCGTAGATATTGGGAAGAACACCGGTGG CGAAGGCGGCAACCTGGCTCGATACTGACGCTGAGGCG CGAAAGCGTGGGGAGCAAACAG |
| SEQ ID NO: 25 | AGTCGTAACAAGGTTTCCGTAGGTGAACCTGCGGAAGG ATCATTAGATTGAATTATCATTGTTGCTCGAGTTCTTG TTTAGATCTTTTACAATAATGTGTATCTTTATTGAAGA TGTGCGCTTAATTGCGCTGCTTCTTTAAAGTGTCGCAG TGAAAGTAGTCTTGCTTGAATCTCAGTCAACGCTACAC ACATTGGAGTTTTTTTACTTTAATTTAATTCTTTCTGC TTTGAATCGAAAGGTTCAAGGCAAAAAACAAACACAAA CAATTTTATTTTATTATAATTTTTTAAACTAAACCAAA ATTCCTAACGGAAATTTTAAAATAATTTAAAACTTTCA ACAACGGATCTCTTGGTTCTCT |

The at least one microbe can be grown in a culture. The at least one microbe can be isolated and purified from the culture. The at least one microbe purified from the culture can comprise a vegetative cell or spore of the at least one microbe. The culture can be a solid or semi-solid medium. The culture can be a liquid medium. The culture can be a bioreactor. Any suitable bioreactor can be used. Examples of bioreactors include, but are not limited to a flask, continuously stirred tank bioreactor (CSTR), a bubbleless bioreactor, an airlift reactor, and a membrane bioreactor. In some instances, a supernatant of the culture comprises a secondary metabolite of the least one microbe. The secondary metabolite of the at least one microbe can be isolated and purified from the supernatant. In some cases, the supernatant can be applied as the biocontrol composition as described elsewhere herein.

The biocontrol composition can comprise one or more secondary metabolites of the at least one microbe. The one or more secondary metabolites can have antifungal properties of its own. The one or more secondary metabolites may with other microbes in a biocontrol composition have antifungal properties. The one or more secondary metabolites can be isolated from a supernatant of the culture of the at least one microbe. The one or more secondary metabolites can comprise a lipopeptide, a dipeptide, an aminopolyol, a protein, a siderophore, a phenazine compound, a polyketide, or a combination thereof.

The lipopeptide can be a linear lipopeptide or a cyclic lipopeptide (CLP). Examples of lipopeptides include, but are not limitied to a surfactin, a fengycin, an iturin, a massetolide, an amphisin, an arthrofactin, a tolassin, a syringopeptide, a syringomycin, a putisolvin, a bacillomycin, a bacillopeptin, a bacitracin, a polymyxin, a daptomycin, a mycosubtilin, a kurstakin, a tensin, a plipastatin, a viscosin, and an echinocandin. The echinocandin can be echinocandib B (ECB). In some instances, the secondary metabolite is a surfatin, a fengycin, an iturin, or a combination thereof.

The dipeptide can be bacilysin or chlorotetain. The polyketide can be defficidin, macrolactin, bacillaene, butyrolactol A, soraphen A, hippolachnin A, or forazoline A. The secondary metabolite can be an aminopolyol. The aminopolyol can be zwittermicin A. The secondary metabolite can be a protein. The protein can be a bacisubin, subtilin, or a fungicin.

The siderophore can be a pyoverdine, thioquinolobactin, or a pyochelin. The phenazine compound can be a phenzine-1-carboxylic acid, a 1-hydroxyphenazine, or a phenazine-1-carboxaminde. The secondary metabolite can be a chitinase, a cellulase, an amylase, or a glucanase. The secondary metabolite can be a volatile antifungal compound.

The biocontrol composition can be formulated as a liquid formulation or a dry formulation. The liquid formulation can be a flowable or aqueous suspension. The liquid formulation can comprise the at least one microbe or a secondary metabolite thereof suspended in water, oil, or a combination thereof (an emulsion). A dry formulation can be a wettable powder, a dry flake, a dust, or a granule. A wettable powder can be applied to the plant, the seed, the flower, or the produce thereof as a suspension. A dust can be applied to the plant, the seed, or the produce thereof dry, such as to seeds or foliage. A granule can be applied dry or can be mixed with water to create a suspension. The at least one microbe or a secondary metabolite thereof can be formulated as a microencapsulation, wherein the at least one microbe or a secondary metabolite thereof has a protective inert layer. The protective inert layer can comprise any suitable polymer.

The biocontrol composition can further comprise an additional compound. The additional compound can be a carrier, a surfactant, a wetting agent, a penetrant, an emulsifier, a spreader, a sticker, a stabilizer, a nutrient, a binder, a desiccant, a thickener, a dispersant, a UV protectant, or a combination thereof. The carrier can be a liquid carrier, a mineral carrier, or an organic carrier. Examples of a liquid carrier include, but are not limited to, vegetable oil or water. Examples of a mineral carrier include, but are not limited to, kaolinite clay or diatomaceous earth. Examples of an organic carrier include, but are not limited to, grain flour. The surfactant can be an anionic surfactant, a cationic surfactant, an amphoteric surfactant, or a nonionic surfactant. The surfactant can be Tween 20 or Tween 80. The wetting agent can comprise a polyoxyethylene ester, an ethoxy sulfate, or a derivative thereof. In some cases a wetting agent is mixed with a nonionic surfactant. A penetrant can comprise a hydrocarbon. A spreader can comprise a fatty acid, a latex, an aliphatic alcohol, a crop oil (e.g. cottonseed), or an inorganic oil. A sticker can comprise emulsified polyethylene, a polymerized resin, a fatty acid, a petroleum distillate, or pregelantinized corn flour. The oil can be coconut oil, palm oil, castor oil, or lanolin. The stabilizer can be lactose or sodium benzoate. The nutrient can be molasses or peptone. The binder can be gum arabic or carboxymethylcellulose. The desiccant can be silica gel or an anhydrous salt. A thickener can comprise a polyacrylamide, a polyethylene polymer, a polysaccharide, xanthan gum, or a vegetable oil. The dispersant can be microcrystalline cellulose. The UV protectant can be oxybenzone, blankophor BBH, or lignin.

The biocontrol composition can further comprise dipicolinic acid.

The at least one microbe can comprise an effective amount of isolated and purified microbes isolated and purified from a liquid culture. The at least one microbe from the liquid culture can be air-dried, freeze-dried, spray-dried, or fluidized bed-dried to produce a dry formulation. The dry formulation can be reconstituted in a liquid to produce a liquid formulation.

The biocontrol composition can be formulated such that the at least one microbe can replicate once they are applied/or delivered to the target habitat (e.g. the soil, the plant, the seed, and/or the produce).

The biocontrol composition can have a shelf life of at least one week, one month, six months, at least one year, at least two years, at least three years, at least four years, or at least five years. The shelf life can indicate the length of time the biocontrol composition maintains at least 80%, at least 85%, at least 90%, at least 95%, at least 99%, or 100% of its anti-fungal properties. The biocontrol composition can be stored at room temperate, at or below 4° C., at or below 0° C., or at or below −20° C.

The biocontrol composition can comprise spores. Spore-containing compositions can be applied by methods described herein. Spore-containing compositions can extend the shelf life of the biocontrol composition. Spore-containing compositions can survive low pH or low temperatures of a target habitat. For example, spore-containing compositions may be applied to the soil at a colder temperature (for example, below 10° C.) and can have anti-fungal properties for a seed planted at a higher temperature (for example, 20° C.). The spores may become vegetative cells, allowing them any advantages of vegetative cells.

The biocontrol composition can comprise vegetative cells. Vegetative cell-containing compositions can be applied by methods described herein. Vegetative cells may proliferate and increase efficacy of the composition. For example, vegetative cells in the biocontrol composition may proliferate after application increasing the surface area the plant that is exposed to the biocontrol composition. In another example, vegetative cells in the biocontrol composition may proliferate after application increasing the amount of the time the biocontrol composition survives and thus extending the time the biocontrol composition has efficacy. The vegetative cells may proliferate and compete for nutrients with a fungal pathogen. The vegetative cells may actively produce one or more secondary metabolites with anti-fungal properties. The vegetative cells may become spores, allowing them any advantages of spores.

The biocontrol composition can have anti-fungal activity, such as prevention of growth of a fungal pathogen or reduction of growth of a fungal pathogen on a plant, a seed, or a produce thereof. The biocontrol composition can prevent growth of a fungal pathogen on the plant, seed, or produce thereof for at least 1, at least 2, at least 3, at least 4, or at least 5 days. The biocontrol composition can prevent growth of a fungal pathogen on the plant, seed, or produce thereof for at least 1, at least 2, at least 3, at least 4, at least 5 days, at least 6 days, at least 7 days, at least 8 days, at least 9 days, or at least 10 days. The biocontrol composition can prevent growth of a fungal pathogen on the plant, seed, or produce thereof for over 10 days.

The biocontrol composition can reduce growth of the fungal pathogen on the plant, seed, or produce thereof relative to growth of the fungal pathogen on a control that is a plant, a seed, flower, or a produce thereof not exposed to the biocontrol composition. The control can be a plant, a seed, or a produce thereof to which no anti-fungal agent has been applied or can be a plant, a seed, flower, or produce thereof to which a commercially available anti-fungal agent has been applied. Examples of commercially available anti-fungal agents include, but are not limited to, *Bacillus subtilis* strain QST713 (Serenade®), *Bacillus subtilis* strain GB02 (Kodiak®), *Bacillus subtilis* strain MBI 600 (Subtilex®), *Bacillus pumilus* strain GB34 (YieldShield), *Bacillus licheniformis* strain SB3086 (EcoGuard®). The biocontrol composition can reduce growth of a fungal pathogen on the plant, seed, or produce thereof for at least 1, at least 2, at least 3, at least 4, or at least 5 days. The biocontrol composition can reduce growth of a fungal pathogen on the plant, seed, or produce thereof for at least 1, at least 2, at least 3, at least 4, at least 5 days, at least 6 days, at least 7 days, at least 8 days, at least 9 days, or at least 10 days. The biocontrol composition can reduce growth of a fungal pathogen on the plant, seed, or produce thereof for over 10 days. The biocontrol composition can reduce growth of the fungal pathogen of at least 25% relative to growth of the fungal pathogen on the control. The biocontrol composition can reduce growth of the fungal pathogen of at least 60% relative to growth of the fungal pathogen on the control. The biocontrol composition can reduce growth of the fungal pathogen of at least 25%, 30%, 35%, 40%, 45%, 50%, 55%, 60% 65%, 70%, 75%, 80%, 85%, 90%, 95%, 99%, or more relative to growth of the fungal pathogen on the control.

The fungal pathogen can be a fungal pathogen in the genus *Albugo, Alternaria, Aphanomyces, Armillaria, Aspergillus, Botrytis, Botrydiplodia, Botrytinia, Bremia, Cercospora, Cercosporella, Cladosporium, Colletotrichum, Cordana, Corynespora, Cylindrocarpon, Daktulosphaira, Didymella, Elsinoe, Erysiphe, Eutypa, Fusarium, Ganoderma, Guignardia, Gymnoconia, Helminthosporium, Leptosphaeria, Leveillula, Macrophomina, Microsphaera, Monolinia, Mycosphaerella, Oidopsis, Passalora, Peronospora, Phomopsis, Phytophthora, Peronospora, Phoma, Plasmodiophora, Plasmopara, Podosphaera, Polyscytalum, Pseudocercospora, Puccinia, Pucciniastrum, Pythium, Ralstonia, Ramularia, Rhizoctonia, Rhizopus, Septoria, Sclerotinia, Sclerotium, Sphaerotheca, Sphaceloma, Spongospora, Stemphylium, Synchytrium, Thielaviopsis, Uncinula, Uromyces,* or *Verticillium*. The fungal pathogen can be *Albugo candida, Albugo occidentalis, Alternaria alternata, Alternaria cucumerina, Alternaria dauci, Alternaria solani Alternaria tenuis, Alternaria tenuissima, Alternaria tomatophila, Aphanomyces euteiches, Aphanomyces raphani, Armillaria mellea, Botrydia theobromae, Botrytis cinerea, Botrytinia fuckeliana, Bremia lactuca, Cercospora beticola, Cercosporella rubi, Cladosporium herbarum, Colletotrichum acutatum, Colletotrichum gloeosporioides, Colletotrichum lindemuthianum, Colletotrichum musae, Colletotrichum spaethanium, Cordana musae, Corynespora cassiicola, Daktulosphaira vitalliae, Didymella bryoniae, Elsinoe ampelina, Elsinoe mangiferae, Elsinoe veneta, Erysiphe cichoracearum, Erysiphe necator, Eutypa lata, Fusarium germinareum, Fusarium oxysporum, Fusarium solani, Ganoderma boninense, Guignardia bidwellii, Gymnoconia peckiana, Helminthosporium solani, Leptosphaeria coniothyrium, Leptosphaeria maculans, Leveillula taurica, Macrophomina phaseolina, Microsphaera alni, Monilinia fructicola, Monilinia vaccinii-corymbosi, Mycosphaerella angulate, Mycosphaerella brassicicola, Mycosphaerella fragariae, Mycosphaerella fijiensis, Oidopsis taurica, Passalora fulva, Peronospora sparse, Peronospora farinosa, Phoma exigua, Phomopsis obscurans, Phomopsis vaccinia, Phomopsis viticola, Phytophthora capsica, Phytophthora erythroseptica, Phytophthora infestans, Phytophthora parasitica, Plasmopara viticola, Plasmodiophora brassicae, Podosphaera macularis, Polyscytalum pustulans, Pseudocercospora vitis, Puccinia allii, Puccinia sorghi, Pucciniastrum vaccinia, Pythium debaryanum, Pythium sulcatum, Pythium ultimum, Ralstonia solanacearum, Ramularia tulasneii, Rhizoctonia solani, Rhizopus arrhizus, Rhizopus stoloniferz, Sclerotinia minor, Sclerotinia sclerotiorum, Sclerotium cepivorum, Sclerotium rolfsii, Sclerotinia minor, Sclerotinia sclerotiorum, Septoria apiicola, Septoria lactucae, Septoria lycopersici, Septoria petroelini, Sphaceloma perseae, Sphaerotheca macularis, Spongospora subterrannea, Stemphylium vesicarium, Synchytrium endobioticum, Thielaviopsis basicola, Uncinula necator, Uromyces appendiculatus, Uromyces betae, Verticillium albo-atrum, Verticillium dahliae, Verticillium theobromae,* or a combination thereof. The fungal pathogen can be *Fusarium oxysporum* or *Verticillium dahliae*. The fungal pathogen can be *Botrytis cinerea*. The fungal pathogen can be *Colletotrichum spaethanium*. The fungal pathogen can be *Erysiphe necator*. The fungal pathogen can be *Peronospora farinosa*. The fungal pathogen can be *Podosphaera maculari*. The fungal pathogen can be *Monilinia vaccinii-corymbosi*. The fungal pathogen can be *Puccinia sorghi*. The fungal pathogen can be a fungal pathogen causing Powdery Mildew. The fungal pathogen can be a fungal pathogen causing Downy Mildew. The fungal pathogen can be a fungal pathogen causing mummy berry. The fungal pathogen can be a fungal pathogen causing corn rust.

The plant, flower, seed, or produce thereof can be of an almond, apricot, apple, artichoke, banana, barley, beet, blackberry, blueberry, broccoli, Brussels sprout, cabbage, cannabis, capsicum, carrot, celery, chard, cherry, citrus, corn, cucurbit, date, fig, garlic, grape, herb, spice, kale, lettuce, oil palm, olive, onion, pea, pear, peach, peanut, papaya, parsnip, pecan, persimmon, plum, pomegranate, potato, quince, radish, raspberry, rose, rice, sloe, sorghum, soybean, spinach, strawberry, sweet potato, tobacco, tomato, turnip greens, walnut, or wheat. The plant, seed, flower, or produce thereof can be a plant or produce thereof can be from the family Rosaceae. The plant, flower, seed, or produce thereof from the family Rosaceae can be from the genus *Rubus*, such as a raspberry or blackberry, *Fragaria*, such as a strawberry, *Pyrus* such as a pear, *Cydonia* such as a quince, *Prunus*, such as an almond, peach, plum, apricot, cherry or sloe, *Rosa*, such as a rose, or *Malus*, such as an apple. The plant, seed, flower, or produce thereof can be a plant or produce thereof from the family Ericaceae. The plant, seed, flower, or produce thereof from the family Ericaceae can be from the genus *Vaccinium*, such as a blueberry. The plant, seed, flower, or produce thereof can be a plant or produce thereof from the family Ericaceae. The plant, seed, flower, or produce thereof from the family Ericaceae can be from the genus *Vaccinium*, such as a blueberry. The plant, seed, flower, or produce thereof can be a plant or produce thereof from the family Vitaceae. The plant, seed, flower, or produce thereof from the family Vitaceae can be from the genus *Vitis*, such as a grape.

Methods of Identification and Isolation of the Biocontrol Composition.

Methods of identifying and/or selecting for a biocontrol composition can comprise culturing the at least one microbe in isolation or with a plurality of other microbes and/or fungal pathogens. For example, the at least one microbe can be cultured with a fungal pathogen to identify efficacy of the at least one microbe to inhibit growth of the fungal pathogen. The efficacy of the at least one microbe to inhibit the growth of the fungal pathogen can be determined by the observing the growth parameters of the fungal pathogen. For example, the lack of living fungal pathogen close to the at least one microbe on a semi-solid or solid growth media may be used determine a high efficacy of inhibition. The optical density of a liquid media containing the at least one microbe and the fungal pathogen may be used to identify an efficacy of the at least one microbe.

The at least one microbe can be identified by a variety of methods. The at least one microbe can be subjected to a sequencing reaction. The sequencing reaction may identify a sequence of 16S rRNA, 12S rRNA, 18S rRNA, 28S rRNA, 13S rRNA and 23S rRNA, internal transcribed spacer (ITS), ITS1, ITS2, cytochrome oxidase I (COI), cytochrome b, or any combination thereof) The sequencing reaction may identify a 16S rRNA sequence, an ITS sequence, or a combination thereof. The sequencing reaction may be used to identify the species or strain of the at least one microbe.

The at least one microbe may be affected by other microbes. The microbes can behave synergistically when cultured together such that the anti-fungal properties are improved when cultured together compared to when cultured separately. For example, the at least one microbe may have increased viability when cultured with another microbe. The at least one microbe may have increased proliferation when cultured with another microbe. The at least one microbe may use chemicals or metabolites produced by another microbe. The at least one microbe may interact directly with another microbe. For example, the at least one microbe and another microbe may form biofilms or a multicellular structure. The at least one microbe may produce and/or secrete an increased amount of the secondary metabolite when cultured with another microbe. For example, the at least one microbe may produce an intermediate metabolite, which in turn is processed by another microbe resulting in the secondary metabolite. Methods disclosed elsewhere herein can be used to identify microbes which may benefit from culturing with another microbe, as well as identify biocontrol compositions comprising a first microbe and a second microbe wherein the second microbe is not identical to the first microbe.

In some cases, the at least one microbe may be affected by environmental conditions. The at least one microbe may grow or produce a secondary metabolite at a particular pH. For example, the pH at which the at least one microbe is grown in may be a pH of 3.0, 4.0, 5.0, 6.0, 6.2, 6.4, 6.6, 6.8, 7.0, 7.2, 7.4, 7.6, 7.8, 8.0, 9.0, 10.0 or higher. For example, the pH at which the at least one microbe is grown in may be a pH of 3.0, 4.0, 5.0, 6.0, 6.2, 6.4, 6.6, 6.8, 7.0, 7.2, 7.4, 7.6, 7.8, 8.0, 9.0, 10.0 or lower. The at least one microbe may grow or produce a secondary metabolite in the presence of salts. The salts may be buffer salts. The at least one microbe may grow or produce a secondary metabolite in the presence of sugars or carbohydrates The sugar or carbohydrate may be glucose or glycerol.

The biocontrol compositions can be cultured using a variety of media or substrate. The at least one microbe can be cultures on an agar dish. The at least one microbe can be cultured on a semi-solid agar dish. The at least one microbe can be cultured in a liquid media.

Selection of Microbial Consortia

Methods for identifying or selecting biocontrol compositions comprising microbial consortia can be used. For example, methods as disclosed in U.S. Patent Publication No. US 20180127796 can be used for identifying or selecting for microbial consortia. In some cases, a plurality of microbes can be grown together. In some cases, the method can comprise diluting a sample to form plurality of dilution, wherein a dilution in the plurality of dilutions comprises a subset of the plurality of microbes. The dilutions may allow for the generation of a plurality of subsets in which different microbes of the plurality of microbes are allowed to interact. The subset of the plurality of microbes can be subjected to culturing such that the microbes may proliferate. The subsets can be subjected to sequencing reactions such that sequences of the microbes can be obtained. From the sequencing reaction, the species, strain, or other taxonomic information can be obtained. Sequences to identify a particular microbe are discussed elsewhere herein. The subsets can be subjected to varying culturing times such can be subjected to sequencing reactions at various times to monitor the presences and/or relative abundance of a particular species, strain or other taxonomic category. By observing the changes in the presence and/or relative abundance of a particular species, strain or other taxonomic category, the interaction between multiple microbes can be determined. For example, a first microbe may have a higher relative abundance when cultured with a second microbe when compared to a relative abundance when not cultured with the second microbe. In this example, the first microbe may interact with the second microbe such that the first microbe's overall viability is increased. The plurality of dilutions can each be subjected to sequencing reactions such that the microbes of each dilution can be identified, and can allow for a multiplexed, high throughput approach.

The plurality of microbes can be diluted such that a subset of the plurality of microbes are grown together. In some cases, diluting the plurality of microbes serially to form a plurality of serial dilutions of the sample can be performed. Microbes in the plurality of serial dilutions of the sample can be due to dispersal or chance. The plurality of serial dilutions can be different in different implementations. In some embodiments, the plurality of serial dilutions of the sample can comprise, or about, 1:10, 1:100, 1:1000, 1:10000, 1:100000, 1:1000000, 1:10000000, 1:100000000, 1:1000000000, or a number or a range between any two of these values, dilutions of the sample. In some embodiments, the plurality of serial dilutions of the sample can comprise at least, or at most, 1:10, 1:100, 1:1000, 1:10000, 1:100000, 1:1000000, 1:10000000, 1:100000000, or 1:1000000000 dilutions of the sample. For example, a sample can be diluted 10 times into a 1:10 dilution of the sample using, for example, a buffer. The 1:10 dilution of the sample can be diluted 10 times into a 1:100 dilution of the sample. The plurality of serial dilutions can comprise the 1:10 dilution of the sample, 1:100 dilution of the sample, and other dilutions of the sample similarly prepared. As another example, a sample can be diluted 10 times into a 1:10 dilution of the sample using, for example, a buffer. The sample can be diluted 100 times into a 1:100 dilution of the sample. The plurality of serial dilutions can comprise the 1:10 dilution of the sample, 1:100 dilution of the sample, and other dilutions of the sample similarly prepared.

In some embodiments, cultivating the plurality of dilutions of the sample in the first cultivation condition comprises cultivating the plurality of dilutions of the sample in the first cultivation condition for a plurality of time durations, which can vary by as little as one minute, up to one year.

The plurality of microbes can be subjected to a sequencing reaction and specific microbes can be identified. Upon culturing the subsets for durations of time, the overall percentage representation of each microbe in the subset may change from the percentage at the start of culturing. For example, microbes which remain viable among other microbes after different periods of culturing may indicate a symbiotic relationship or interaction between the microbes of the culture and these microbes may form a microbial consortium. The microbial consortia can be tested for efficacy of inhibiting the growth of a fungal pathogen in a manner similar to methods used for identifying the efficacy of the at least one microbe as described elsewhere herein.

Isolation of particular microbes may also be performed for use in methods or compositions described elsewhere herein. For example, the plurality of microbes can be subjected to serial dilutions such that a colony of a particular microbe can be isolated. The serial dilutions can each be cultured in liquid, semi-solid, or solid media. On a semi-solid or solid media such as an agar plate, the plurality of microbes can form colonies. The colonies can be well dispersed so that a colony can contain a single strain or species of microbe. Isolation of a particular microbe can also be performed using physical separation methods such a centrifugation. For example, a plurality of microbes may be cultured in liquid media and centrifuged in order to isolate the microbes from the culture. A particular microbe may also be isolated using a particular growth condition. For example, a particular microbe may have higher viability when compared to another microbe when cultured in anaerobic conditions. A particular microbe may have a high viability compared to another microbe when cultured in a media rich in a particular nutrient.

Methods for Prevention or Reduction of Food Rot and Food Spoilage

Treating the Plant, the Seed, Flower, or the Produce Thereof with the Biocontrol Composition Prior to Harvest Methods of preventing or reducing the growth of a fungal pathogen on a plant, a seed, or a produce thereof can comprise applying to the plant, the seed, flower, or the produce, before it has been harvested, a biocontrol composition comprising at least one microbe described herein or one or more secondary metabolites thereof and a carrier. Harvesting the produce can refer to the removal of the edible portion of the plant from the remainder of the plant, or can refer to removal of the entire plant with subsequent removal of the edible portion later.

Applying the biocontrol composition prior to harvest can comprise dusting, injecting, spraying, or brushing the plant, the seed, or the produce thereof with the biocontrol composition. Applying the biocontrol composition can comprise adding the biocontrol composition to a drip line, an irrigation system, a chemigation system, a spray, or a dip. In some cases, the biocontrol composition is applied to the root of the plant, the seed of the plant, the foliage of the plant, the soil surrounding the plant or the edible portion of the plant which is also referred to herein as the produce of the plant The method can further comprise applying to the plant a fertilizer, an herbicide, a pesticide, other biocontrols, or a combination thereof. In some instances, the fertilizer, herbicide, pesticide, other biocontrols or combination thereof is applied before, after, or simultaneous with the biocontrol composition.

Method of preventing or reducing the growth of a fungal pathogen can comprise applying to the seed a biocontrol composition comprising at least one microbe described herein or a secondary metabolite thereof and a carrier. Applying the biocontrol composition to the seed of the plant can occur before planting, during planting, or after planting prior to germination. For example, the biocontrol composition can be applied to the surface of the seed prior to planting. In some cases, a seed treatment occurring before planting can comprise addition of a colorant or dye, a carrier, a binder, a sticker, an anti-foam agent, a lubricant, a nutrient, or a combination thereof to the biocontrol composition.

Method of preventing or reducing the growth of a fungal pathogen can comprise applying to the soil a biocontrol composition comprising at least one microbe described herein or a secondary metabolite thereof and a carrier. The biocontrol composition can be applied to the soil before, after, or during planting the soil with a seed, or before transfer of the plant to a new site. In one example, a soil amendment is added to the soil prior to planting, wherein the soil amendment results in improved growth of a plant, and wherein the soil amendment comprises the biocontrol composition. In some cases, the soil amendment further comprises a fertilizer.

Method of preventing or reducing the growth of a fungal pathogen can comprise applying to the root a biocontrol composition comprising at least one microbe described herein or a secondary metabolite thereof and a carrier. The biocontrol composition can be directly applied to the root. One example of a direct application to the root of the plant can comprise dipping the root in a solution that includes the biocontrol composition. The biocontrol composition can be applied to the root indirectly. One example of an indirect application to the root of the plant can comprise spraying the biocontrol composition near the base of the plant, wherein the biocontrol composition permeates the soil to reach the roots.

Treating the Produce Thereof with the Biocontrol Composition after Harvest

Methods of preventing or reducing the growth of a fungal pathogen on a produce can comprise applying to the produce, before or after it has been harvested, a biocontrol composition comprising at least one microbe described herein or a secondary metabolite thereof and a carrier.

Applying the biocontrol composition before or after harvest can comprise dusting, dipping, rolling, injecting, rubbing, spraying, or brushing the produce of the plant with the biocontrol composition. The biocontrol composition can be applied to the produce immediately prior to harvest or immediately after harvesting or within 1 day, 2 days, 3 days, 4 days, 5 days, 6 days, or 1 week of harvesting. In some cases, the biocontrol composition is applied by the entity doing the harvesting, in a process treating the produce immediately prior to harvest or post-harvest, by the entity packaging the produce, by the entity transporting the produce, or by the entity commercially displaying the produce for sale, or a consumer.

Applying the biocontrol composition after harvest can further comprise integrating the biocontrol composition into a process to treat the produce post-harvest. The produce can be treated immediately post-harvest, for example in one or multiple washes. The one or multiple washes can comprise the use of water that has had bleach (chlorine) and/or sodium bicarbonate added to it, or ozonated water. The produce may also be treated with oils, resins, or structural or chemical matrices. The biocontrol composition may be mixed with the oils, resins, or structural or chemical matrices for application. The produce can be treated before or after drying the produce. For example, the biocontrol composition can be added to a wax, gum arabic or other coating used to coat the produce. The biocontrol composition may be added at any point in the process, included in one of the washes, as part of a new wash, or mixed with the wax, gum arabic or other coating of the produce.

Treating a Packaging Material with the Biocontrol Composition

Methods of preventing or reducing the growth of a fungal pathogen on a produce can comprise applying to a packaging material used to transport or store the produce a biocontrol composition comprising at least one microbe described herein or a secondary metabolite thereof and a carrier.

The packaging material can comprise: polyethylene terephthalate (PET), molded fiber, oriented polystyrene (OPS), polystyrene (PS) foam, polypropylene (PP), or a combination thereof. The packaging material can comprise cardboard, solid board, Styrofoam, or molded pulp. The packaging material can comprise a substrate, such as cellulose. The packaging material can be a horizontal flow (HFFS) package, a vertical flow (VFFS) package, a thermoformed package, a sealed tray, or a stretch film. The thermoformed package can be a clam shell package. The packaging material can be a punnet, a tray, a basket, or a clam shell.

The packaging material treated with the biocontrol composition can be an insert. The insert can be a pad, a sheet, or a blanket. The insert can be placed into or over the punnet, the tray, the basket, or the clam shell. The insert can comprise cellulose or a cellulose derivative. The insert can comprise at least one layer of a micro porous polymer such as polyethylene or polypropylene and at least one layer of a superabsorbent polymer. In some cases, the insert comprises an outer layer and an inner layer. The inner layer can be a water-absorbing layer. The inner layer can comprise a carboxymethyl cellulose, cellulose ether, polyvinyl pyrrolidon, starch, dextrose, gelatin, pectin, or a combination thereof. The outer layer can be a water pervious layer.

Applying the biocontrol composition to the packaging material can comprise washing, spraying, or impregnating the packaging material with the biocontrol composition.

The terminology used herein is for the purpose of describing particular cases only and is not intended to be limiting. The below terms are discussed to illustrate meanings of the terms as used in this specification, in addition to the understanding of these terms by those of skill in the art. As used herein and in the appended claims, the singular forms "a", "an", and "the" include plural referents unless the context clearly dictates otherwise. It is further noted that the claims can be drafted to exclude any optional element. As such, this statement is intended to serve as antecedent basis for use of such exclusive terminology as "solely," "only" and the like in connection with the recitation of claim elements, or use of a "negative" limitation.

Certain ranges are presented herein with numerical values being preceded by the term "about." The term "about" is used herein to provide literal support for the exact number that it precedes, as well as a number that is near to or approximately the number that the term precedes. In determining whether a number is near to or approximately a specifically recited number, the near or approximating un-recited number may be a number which, in the context in which it is presented, provides the substantial equivalent of the specifically recited number. Where a range of values is provided, it is understood that each intervening value, to the tenth of the unit of the lower limit unless the context clearly dictates otherwise, between the upper and lower limit of that range and any other stated or intervening value in that stated range, is encompassed within the methods and compositions described herein are. The upper and lower limits of these smaller ranges may independently be included in the smaller ranges and are also encompassed within the methods and compositions described herein, subject to any specifically excluded limit in the stated range. Where the stated range includes one or both of the limits, ranges excluding either or both of those included limits are also included in the methods and compositions described herein.

Unless defined otherwise, all technical and scientific terms used herein have the same meaning as commonly understood by one of ordinary skill in the art to which the methods and compositions described herein belong. Although any methods and materials similar or equivalent to those described herein can also be used in the practice or testing of the methods and compositions described herein, representative illustrative methods and materials are now described.

EXAMPLES

Example 1

Screening of Microbes for Anti-Fungal Activity

Figure 1:
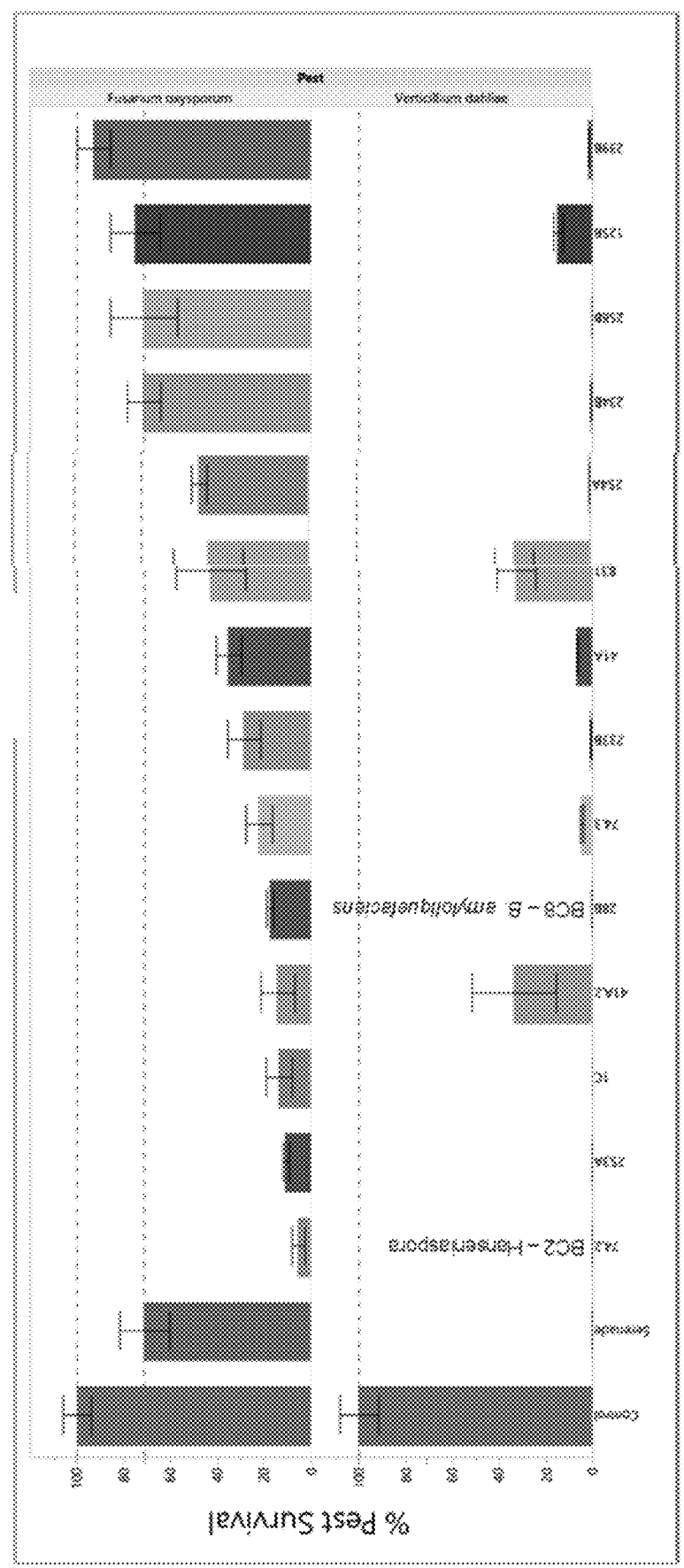
FIG. 1 illustrates % survival of *Verticillium dahliae* and *Fusarium oxysporum* on semi-solid agar following application of 14 candidate microbes compared to a control (Serenade®).
Figure 3:
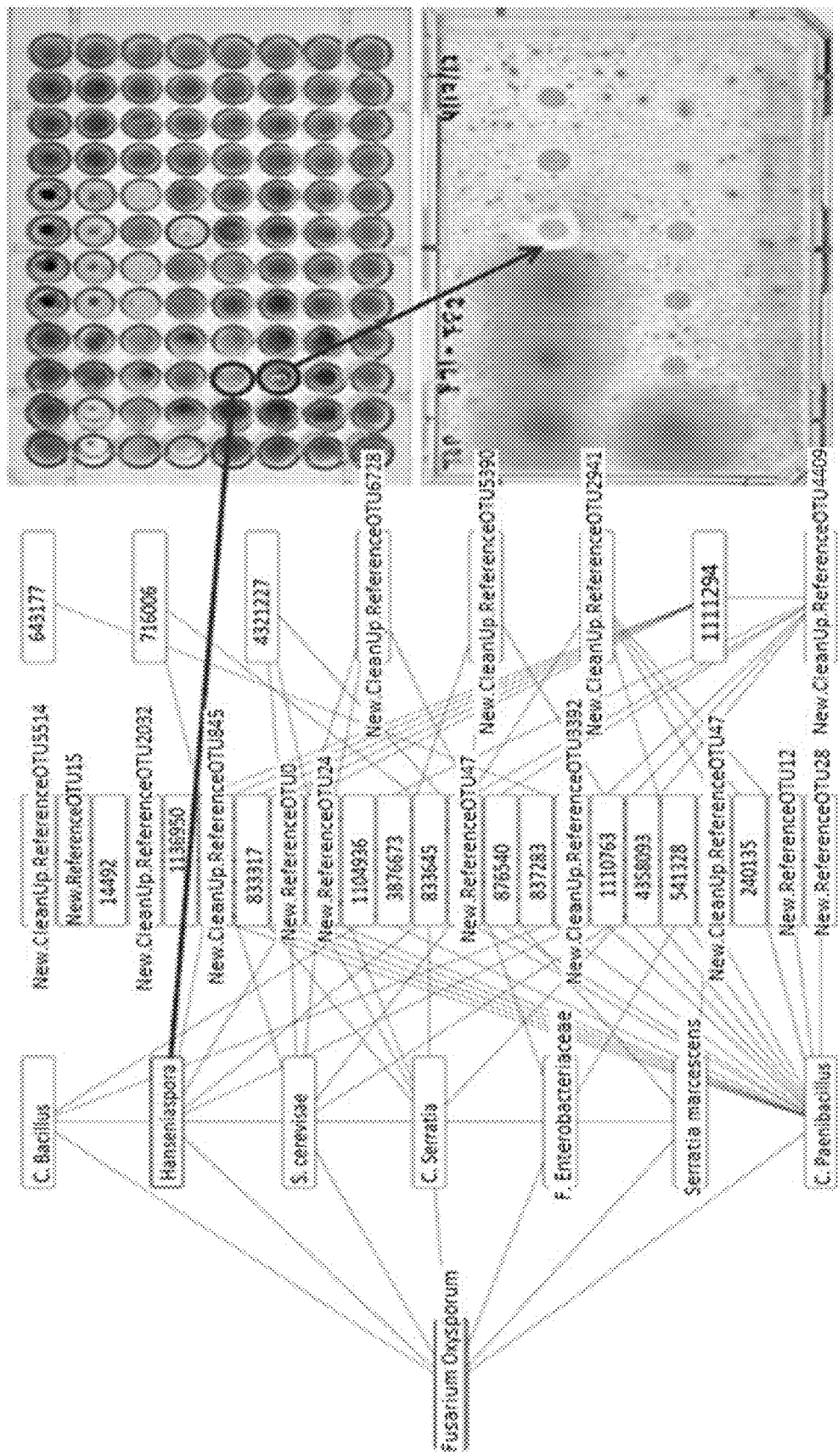
FIG. 3 illustrates identification of candidates using an understanding of interactions among species in an environment. *Hanseniaspora uvarum* was identified as interacting directly with *Fusarium oxysporum*, causing growth inhibition of the fungus. The ability of *Hanseniaspora uvarum* to inhibit growth of *Fusarium oxysporum* was confirmed, and *Hanseniaspora uvarum* was advanced as a product candidate. Shown here is the identified, first-tier interaction between *H. uvarum* and *F. oxysporum*; the identification and isolation of *H. uvarum*; and confirmation of the inhibition of *F. oxysporum* caused by *H. uvarum*.

Microbes were screened for their ability to prevent the growth of the fungal pests *Verticillium dahliae* and *Fusarium oxysporum*. Fourteen candidates were identified as active in a first-tier screen, which was to form clearing zones on lawns of fungi (for example, see FIG. 3 regarding identification of *Hanseniaspora uvarum* as inhibiting *Fusarium oxysporum*). These fourteen candidates were then screened in a second tier assay designed to simulate the structured soil environment by making use of semi-solid agar. In this assay, growth of fungi without treatment was set to 100%, and the reduction of growth was determined relative to the untreated fungi. The commercially-available product Serenade, containing an active ingredient of a QST 713 strain of *Bacillus subtilis*, was used as a control, and reduced the growth of *F. oxysporum* by ~25%, and *V. dahliae* by >99%. Of these candidates, 10 reduced the growth of *F. oxysporum* by more than Serenade®; 11 reduced the growth of *V. dahliae* at a level indistinguishable from Serenade (FIG. 1).

Candidate strains tested are found in Table 3, along with the closest identified microbial species or genus.

TABLE 3

Candidate microbial strains tested for anti-fungal activity compared to Serenade ®

| | Microbial strain identifier from FIG. 1 | Putative microbial genus or species | SEQ ID NO. | 16S or ITS |
|---|---|---|---|---|
| 1 | 74.2 | *Hanseniaspora uvarum* | SEQ ID NO: 18 | ITS |
| 2 | 253 | *Gluconacetobacter liquefaciens* | SEQ ID NO: 4 | 16S |
| 3 | 1C | *Cyberlindnera mrakii* or *Cyberlindnera saturnus* | SEQ ID NO: 17 | ITS |
| 4 | 41A.2 | *Paraburkholderia* or *Burkholderia* | SEQ ID NO: 9 | 16S |
| 5 | 28B | *Bacillus amyloliquefaciens* | SEQ ID NO: 1 | 16S |
| 6 | 74.3 | *Torulaspora delbrueckii* | SEQ ID NO: 19 | ITS |
| 7 | 233B | *Gluconacetobacter liquefaciens* | SEQ ID NO: 11 | 16S |
| 8 | 41A | *Paraburkholderia* or *Burkholderia* | SEQ ID NO: 7 | 16S |
| 9 | B31 | *Pseudomonas lini* | SEQ ID NO: 10 | 16S |

TABLE 3-continued

Candidate microbial strains tested for anti-fungal activity compared to Serenade ®

| Microbial strain identifier from FIG. 1 | | Putative microbial genus or species | SEQ ID NO. | 16S or ITS |
|---|---|---|---|---|
| 10 | 254A | Gluconacetobacter liquefaciens | SEQ ID NO: 5 | 16S |
| 11 | 234B | Gluconacetobacter liquefaciens | SEQ ID NO: 12 | 16S |
| 12 | 258B | Gluconacetobacter liquefaciens | SEQ ID NO: 16 | 16S |
| 13 | 125B | Cutaneotrichosporon moniliiforme | SEQ ID NO: 20 | ITS |
| 14 | 239B | Gluconacetobacter liquefaciens | SEQ ID NO: 13 | 16S |

Example 2

Figure 4:
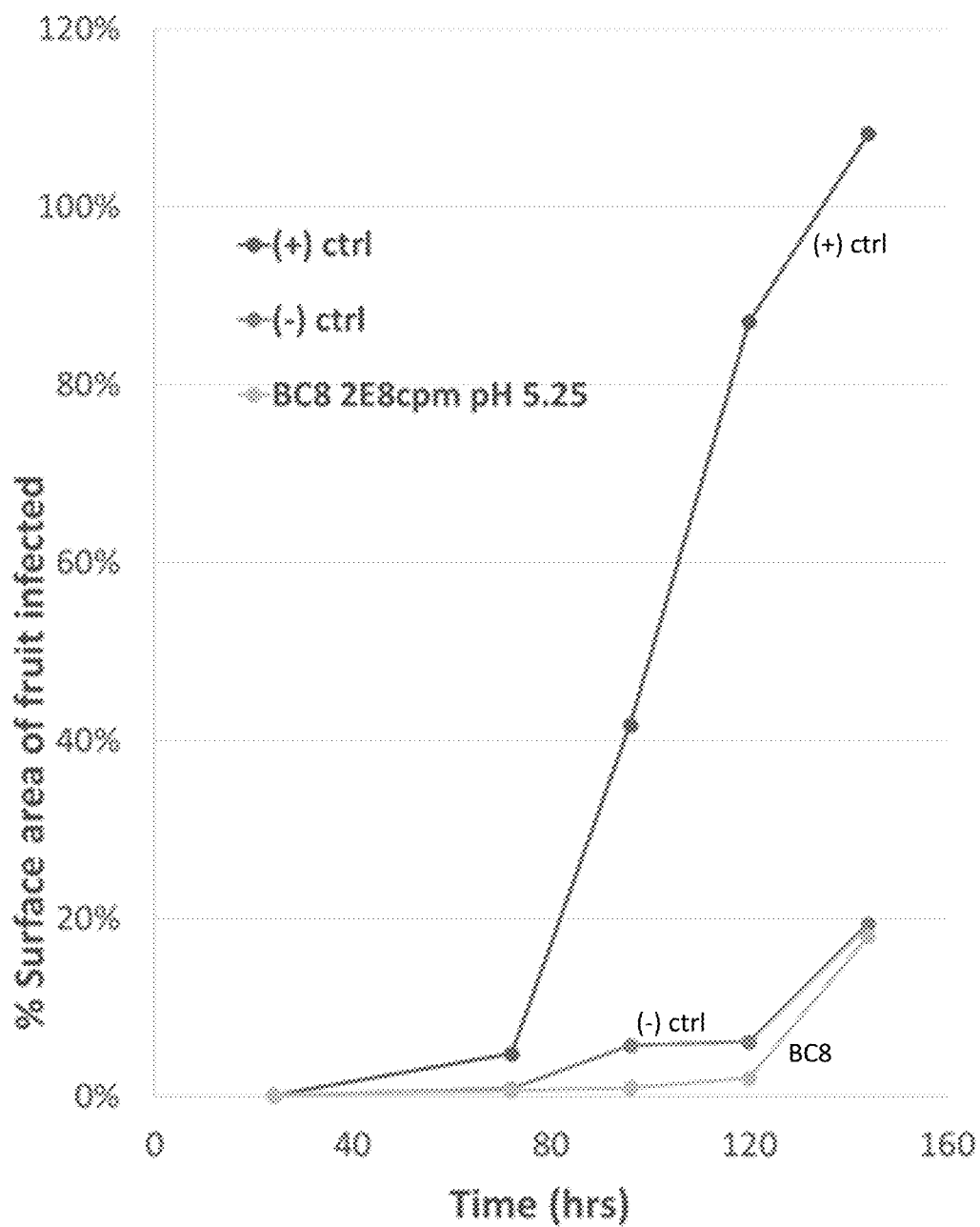
FIG. 4 illustrates the percent surface area of a raspberries infected with *Botrytis cinerea* after different treatments: a (+) control infected with *Botrytis cinerea*, an uninfected (−) control, and a sample infected with *Botrytis cinerea* but to which the supernatant from a culture of product candidate BC8 (*Bacillus amyloliquefaciens*; strain 28B) has been applied.
Figure 5A:
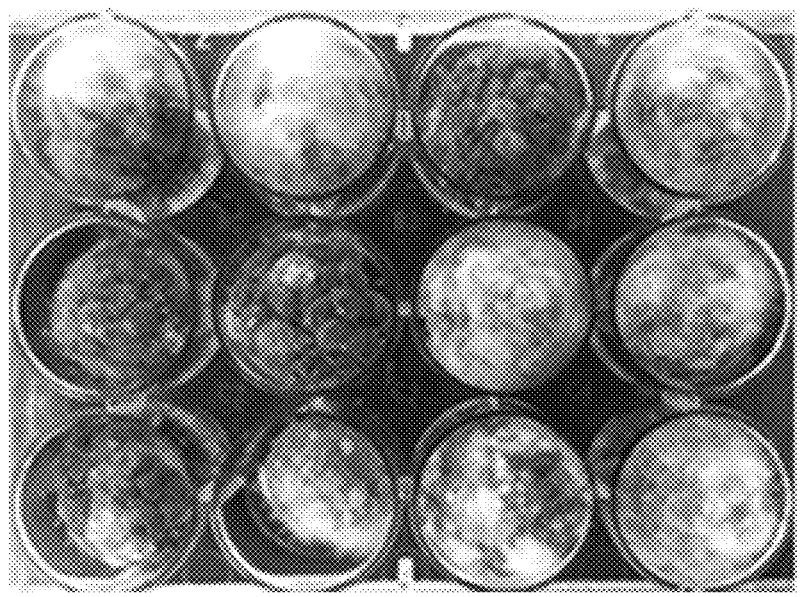
FIGS. 5A-5C illustrate fungal growth on raspberries after different treatments regimes.
Figure 5B:
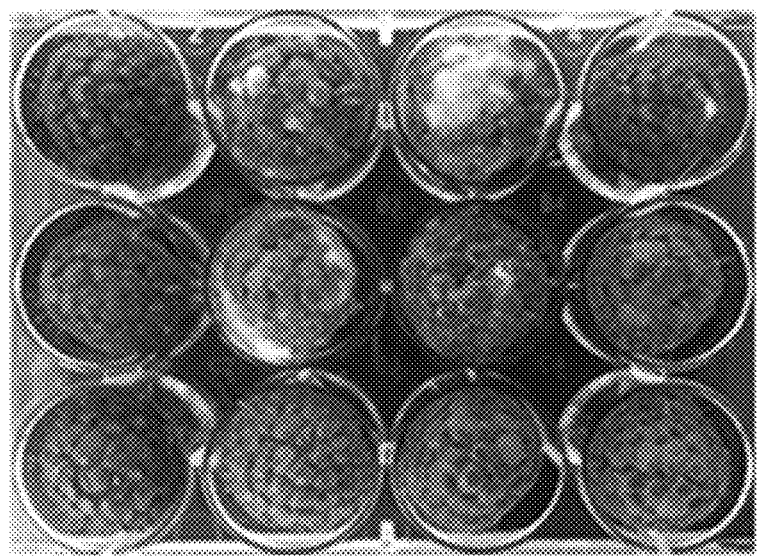
Figure 5C:
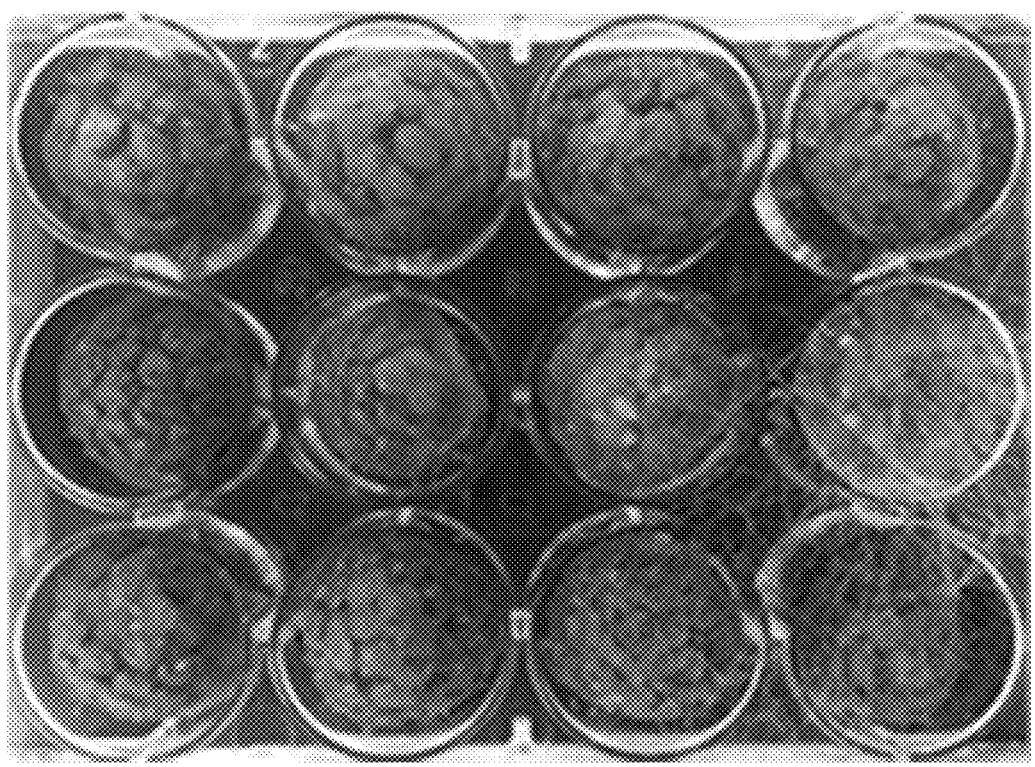

Anti-Fungal Activity of a *Bacillus amyloliquefaciens* (Strain 28B; BC8) Supernatant on Raspberries The anti-fungal activity of the supernatant from a culture of an isolated strain of *Bacillus amyloliquefaciens* (strain 28B; BC8) against *Botrytis cinerea* on raspberries was determined. After 120 hours, the raspberries to which the supernatant of the *Bacillus amyloliquefaciens* strain had been applied showed fungal growth similar to the negative control raspberries (which were not infected with *Botrytis cinerea*), with fungal growth covering less than 5% of the surface area of the raspberries. In contrast, the positive control raspberries (which had been infected with *Botrytis cinerea*) showed about 90% surface area covered with fungal growth after 120 hours (FIG. 4; FIGS. 5A-5C).

Example 3

Evaluation of Efficacy of BC8 Against *Botrytis cinerea* and *Colletotrichum spaethanium* Induced Blight on Blueberry Crop Efficacy of BC8 against *Botrytis cinerea* and *Colletotrichum spaethanium* induced blossom blights in blueberry was assessed. Blueberry bushes were treated with BC8 or control treatments. As control treatments, bushes were either left untreated or treated with Lifegard (Certis; active ingredient: *Bacillus mycoides*), a combination of Stargus (Marrone; active ingredient: *Bacillus amyloliquefaciens* strain F727) and Nufilm (Fertrell; mixture of terpene polymers and emulsifiers), or a sequential application of Bravo Weatherstik (Syngenta; active ingredient: Chlorothalonil (tetrachloroisophthalonitrile) 54%), Captevate (Arysta; active ingredient: fenhexamid, captan) and Pristine (BASF; active ingredient: pyraclostrobin, bosclid). All treatment segments also received standard commercial fertility and insecticide program. The treatment products were mixed in a water volume of 75 gallons (at 0.9 L/treatment or according to the label specification) and applied using a spray device to plants at regular intervals. Bushes were treated at the different stages of growth including, early green tip (EGT), late green tip (LGT), pink bud (PB), bloom (BLM), petal fall (PF), green fruit (GRF), 10% blue fruit (BLF). The bushes were grown and maintained according to grower standard practice.

*Botrytis cinerea* infection was assessed by counting the number of blossom blights per blueberry bush. Four replicates per treatment were conducted, in a randomized plot design format.

Figure 7:
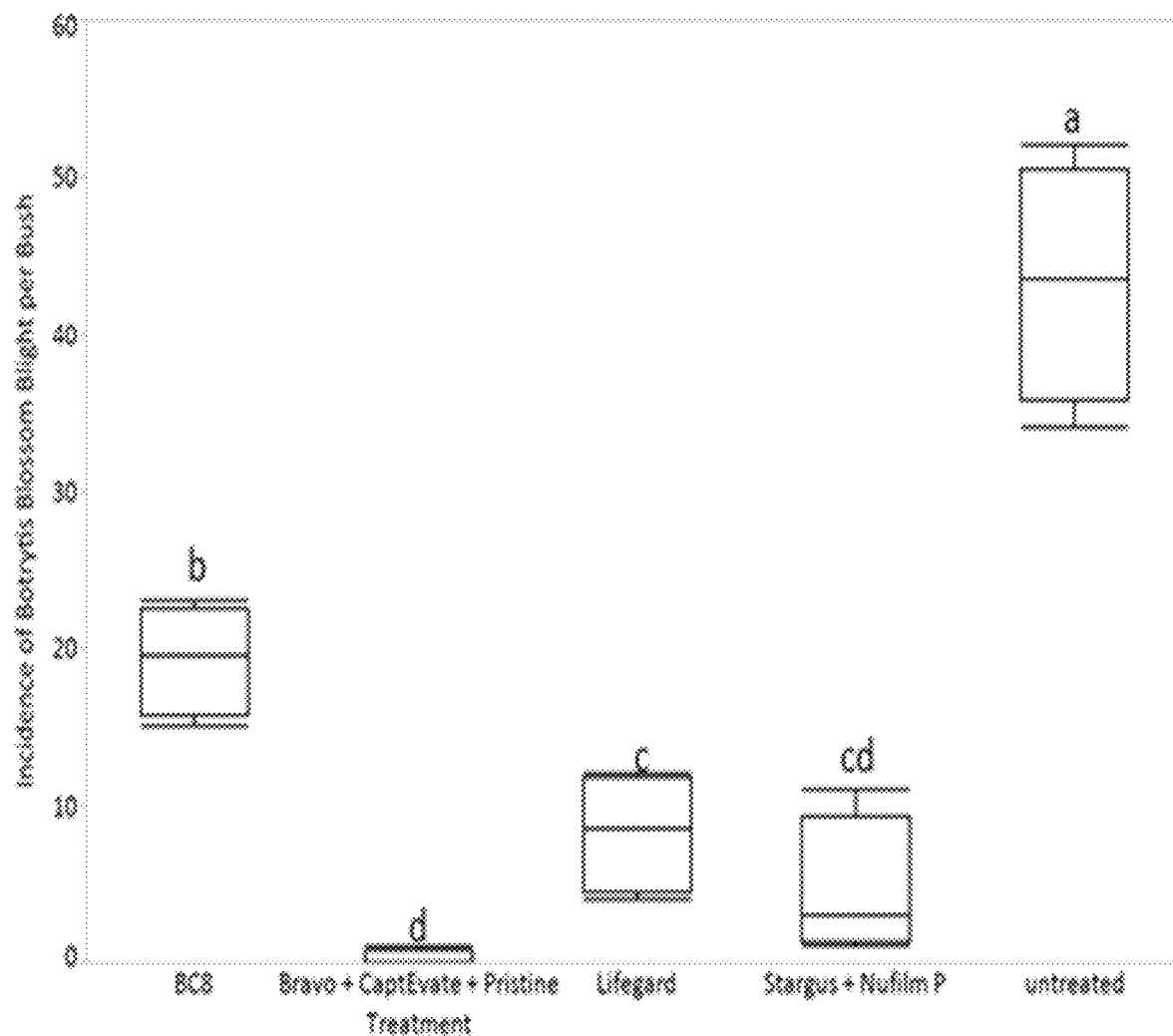
FIG. 7 illustrates incidence of *Botrytis* on blueberry bushes on treated and untreated plants

The results, expressed as incidence of *B. cinerea* induced Blossom Blight per Bush is shown in FIG. 7. BC8 was effective at reducing the incidence of blossom blight by about 55% compared to untreated controls.

Data were analyzed through a one-way analysis of variance (ANOVA) and means were compared using Fisher's least significant difference (LSD). Box plots labeled with the same letter within each graph are not significantly different (LSD p=0.05).

Example 4

Evaluation of Efficacy of BC8 Against Post-Harvest Decay Caused by *Botrytis cinerea* and *Colletotrichum spaethanium* on Blueberry Crop Efficacy of BC8 against post-harvest decay caused by *Botrytis cinerea* or *Colletotrichum* sp. infection on blueberry crop was assessed. Blueberry bushes were treated with BC8 or control treatments prior to harvest and blueberries obtained therefrom were observed post-harvest. As control treatments, bushes were either left untreated or treated with Lifegard (Certis), a combination of Stargus and Nufilm (Fertrell), or a sequential treatment of Bravo Weatherstik (Syngenta), Captevate (Aresta) and Pristine (Bayer).

Figure 8:
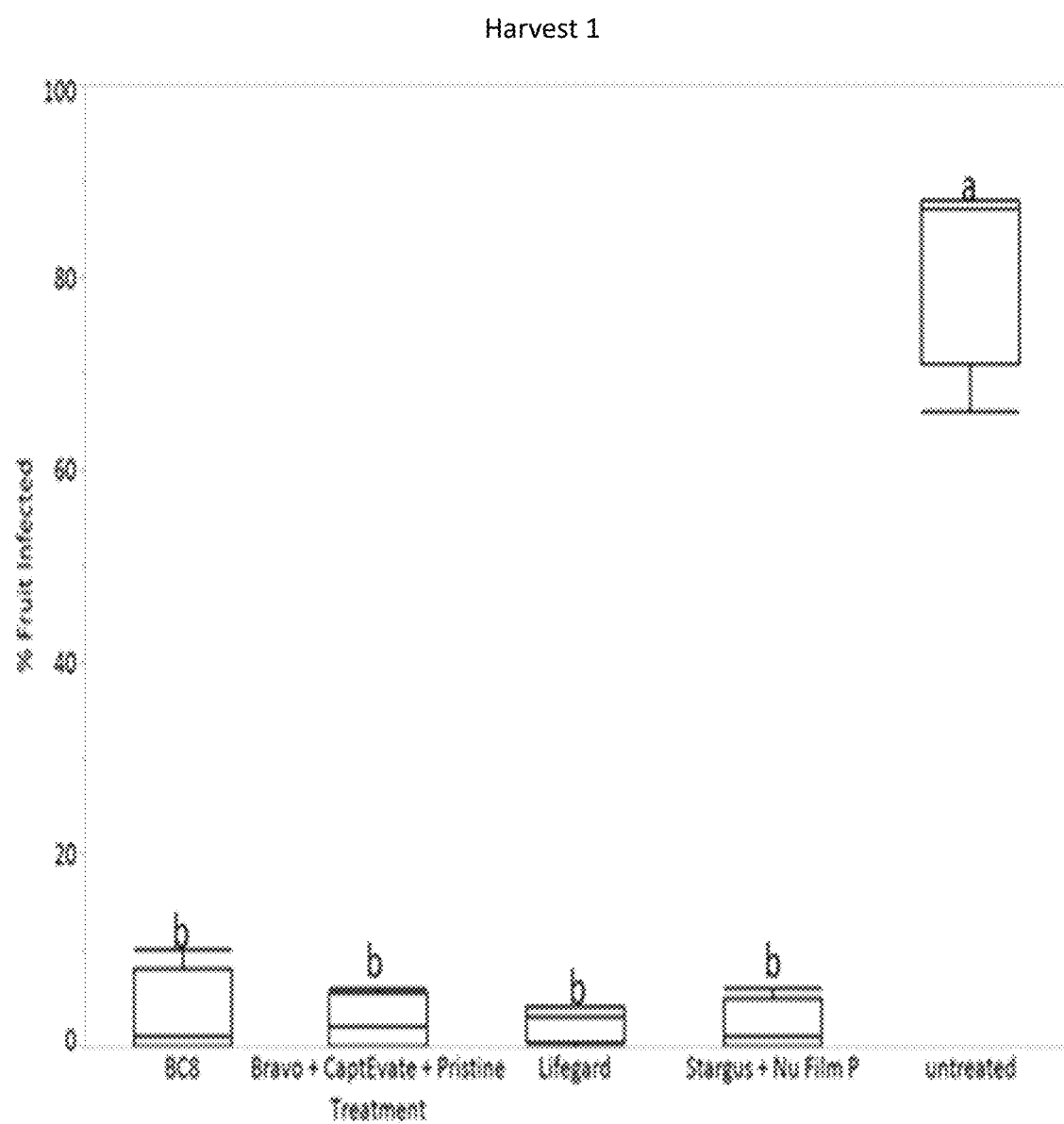
FIG. 8 illustrates the percent of blueberries infected by *Botrytis* on treated and untreated plants.

50 berries were harvested and assessed for post-harvest decay caused by *B. cinerea* and *Colletrotrichum* sp. after placement in humidity chambers at room temperature for 12-14 days. Results expressed as % Fruit Infected are shown in FIG. 8. The treated berries in the harvest had a 10% incidence of berry decay, while untreated berries in the harvest had an 85% incidence of decay (FIG. 8). BC8 was as effective as the commercial standard, a combination of Bravo Weatherstik (Syngenta), Captevate (Aresta) and Pristine (Bayer), in reducing post-harvest decay in blueberry crop (FIG. 8).

Data were analyzed through a one-way analysis of variance (ANOVA) and means were compared using Fisher's least significant difference (LSD). Box plots labeled with the same letter within each graph are not significantly different (LSD p=0.05).

Example 5

Figure 9:
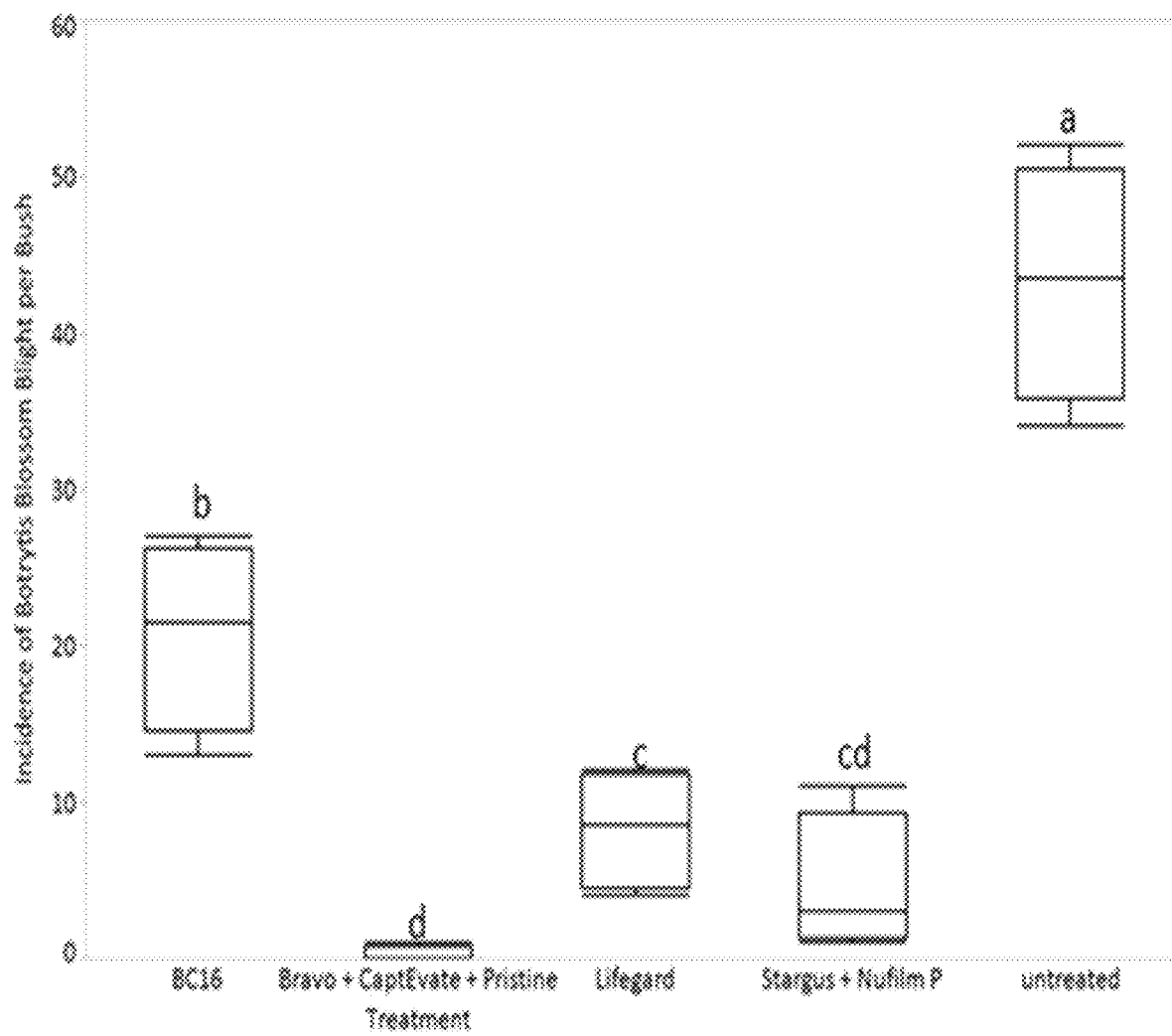
FIG. 9 illustrates the number of incidences of *Botrytis* Blossom Blight per blueberry bush on treated and untreated plants.

Evaluation of Efficacy of BC16 Against *Botrytis cinerea* and *Colletotrichum spaethanium* Induced Blight on Blueberry Crop BC16 was assessed for its efficacy against *Botrytis cinerea* and *Colletotrichum spaethanium* induced blossom blights in blueberry. Blueberry bushes were treated with BC16 or a control treatments. As control treatments, bushes were either left untreated or treated with Lifegard (Certis), a combination of Stargus and Nufilm (Fertrell), or a sequential treatment of Bravo Weatherstik (Syngenta), Captevate (Aresta) and Pristine (Bayer). All treatment segments also received standard commercial fertility and insecticide program. The treatment products were mixed in a water volume of 75 gallons (at 0.9 L/treatment or according to manufacturer's specifications) and applied using a spray device to plants at regular intervals. Bushes were treated at the different stages of growth including, early green tip (EGT), late green tip (LGT), pink bud (PB), bloom (BLM), petal fall (PF), green fruit (GRF), 10% blue fruit (BLF). The bushes were grown and maintained according to grower standard practice Incidence of *Botrytis cinerea* and *Colletotrichum spaethanium* infection was assessed by counting the number of blossom blights per blueberry bush. Four replicates per treatment were conducted, in a randomized plot design format. The results, expressed as incidence of Blossom Blight per Bush are shown in FIG. 9. BC16 was effective at reducing the incidence of blossom blight by about 52% compared to untreated controls.

Data were analyzed through a one-way analysis of variance (ANOVA) and means were compared using Fisher's least significant difference (LSD). Box plots labeled with the same letter within each graph are not significantly different (LSD p=0.05).

Example 6

Figure 10:
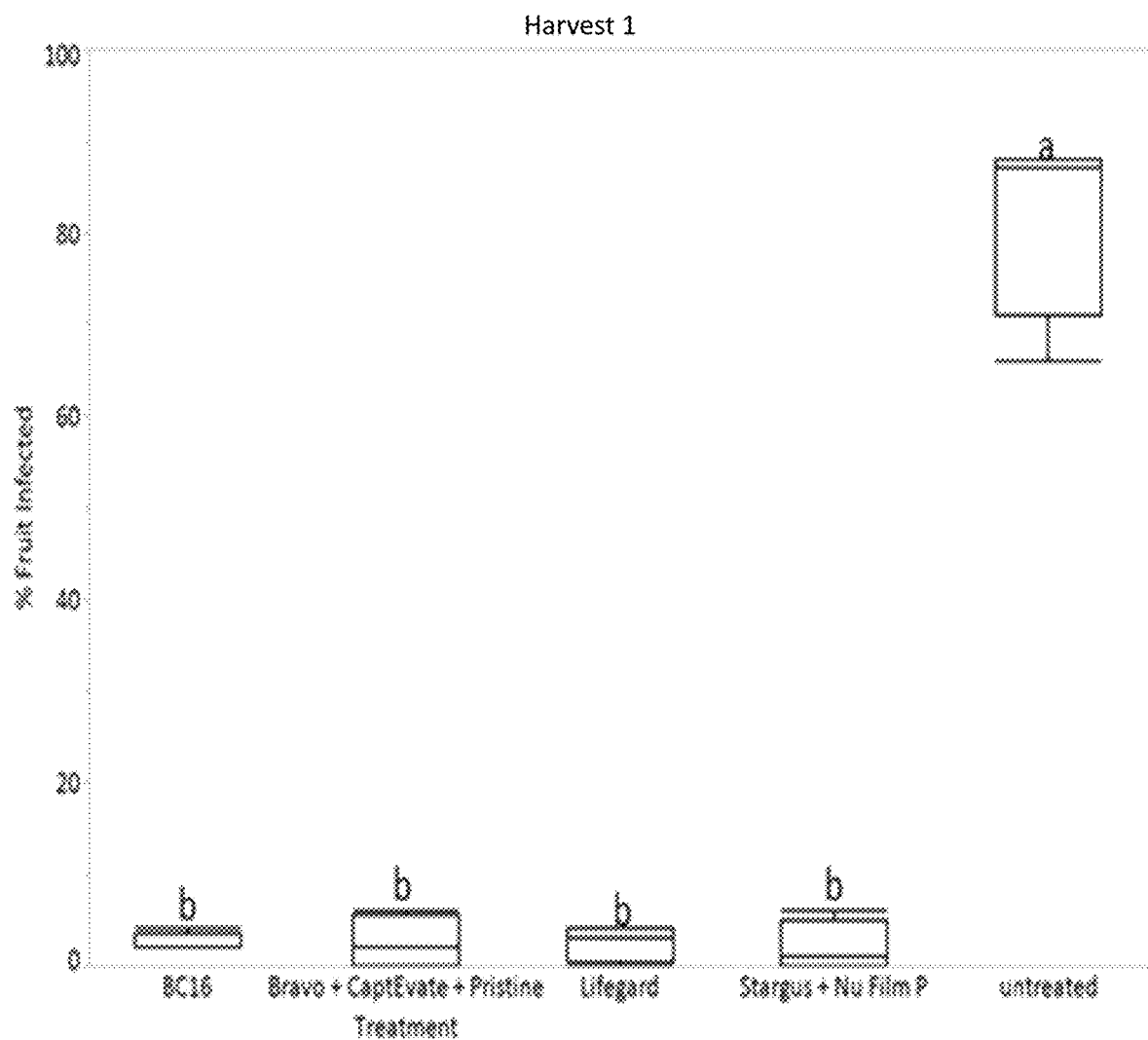
FIG. 10 illustrates the percent blueberries infected by *Botrytis* on treated and untreated plants.

Evaluation of Efficacy of BC16 Against Post-Harvest Decay Caused by *Botrytis cinerea* and *Colletotrichum spaethanium* on Blueberry Crop Efficacy of BC16 against post-harvest decay caused by *Botrytis cinerea* or *Colletotrichum* sp. infection on blueberry crop was assessed. Blueberry bushes were treated with BC16 or a control treatments prior to harvest and blueberries obtained therefrom were observed post-harvest. As control treatments, berries were either left untreated or treated with Lifegard (Certis), a combination of Stargus and Nufilm (Fertrell), or a sequential treatment of Bravo Weatherstik (Syngenta), Captevate (Aresta) and Pristine (Bayer). 50 berries were harvested and assessed for post-harvest decay caused by *B. cinerea* and *Colletotrichum* sp. after placement in humidity chambers at room temperature for 12-14 days. Results expressed as % Fruit Infected are shown in FIG. 10. BC16 treated bushes in harvest 1 had a 5% incidence of berry decay (FIG. 10), while untreated berries in harvest 1 had a decay of 85% in harvest 1 (FIG. 10). BC16 was as effective as Bravo Weatherstik (Syngenta), Captevate (Aresta) and Pristine (Bayer), the commercial standard, in reducing post-harvest decay in blueberry crop (FIG. 10).

Data were analyzed through a one-way analysis of variance (ANOVA) and means were compared using Fisher's least significant difference (LSD). Box plots labeled with the same letter within each graph are not significantly different (LSD p=0.05).

Example 7

Evaluation of Efficacy of BC17 Against *Botrytis cinerea* and *Colletotrichum spaethanium* Induced Blight on Blueberry Crop BC17 was assessed for its efficacy against *Botrytis cinerea* and *Colletotrichum spaethanium* induced blossom blights in blueberry. Blueberry bushes were treated with BC17 or a control product. As control treatments, bushes were either left untreated or treated with Lifegard (Certis), a combination of Stargus and Nufilm (Fertrell), or a sequential treatment of Bravo Weatherstik (Syngenta), Captevate (Aresta) and Pristine (Bayer). All treatment segments also received standard commercial fertility and insecticide program. The treatment products were mixed in a water volume of 75 gallons at 0.9 L/treatment or according to manufacturer's specifications and applied using a spray device to plants at regular intervals. Bushes were treated at the different stages of growth including, early green tip (EGT), late green tip (LGT), pink bud (PB), bloom (BLM), petal fall (PF), green fruit (GRF), 10% blue fruit (BLF). The bushes were grown and maintained according to grower standard practice.

*Botrytis cinerea* infection was assessed by counting the number of blossom blights per blueberry bush. Four replicates per treatment were conducted, in a randomized plot design format.

Figure 11:
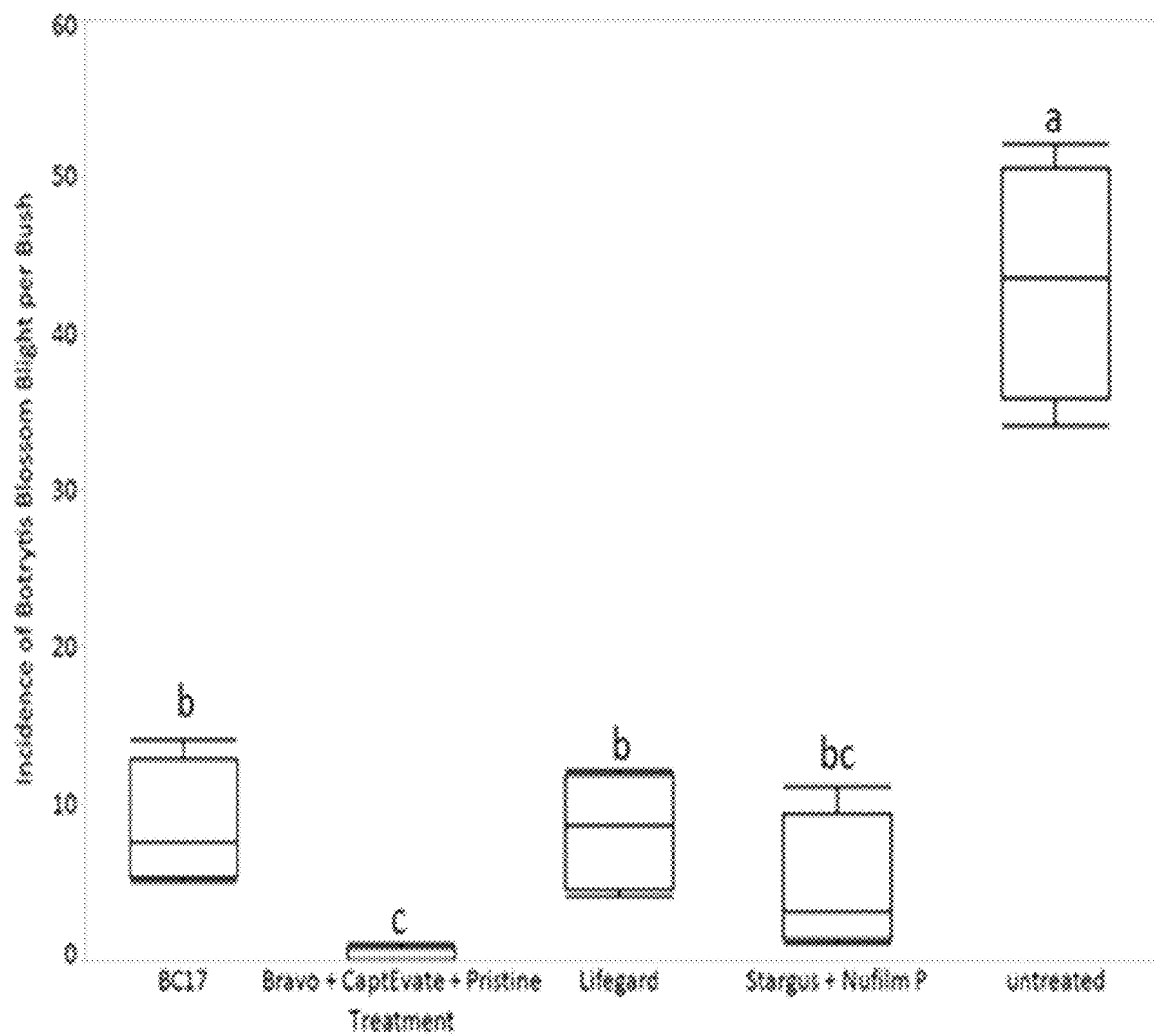
FIG. 11 illustrates the number of incidences of *Botrytis* Blossom Blight per blueberry bush on treated and untreated plants.

The results, expressed as incidence of Blossom Blight per Bush are shown in FIG. 11. BC17 was effective at reducing the incidence of blossom blight by 80% compared to untreated controls.

Data were analyzed through a one-way analysis of variance (ANOVA) and means were compared using Fisher's least significant difference (LSD). Box plots labeled with the same letter within each graph are not significantly different (LSD p=0.05).

Example 8

Evaluation of Efficacy of BC17 Against Post-Harvest Decay Caused by *Botrytis cinerea* and *Colletotrichum spaethanium* on Blueberry Crop BC17 was assessed for its efficacy against post-harvest decay caused by *Botrytis cinerea* or *Colletotrichum* sp. infection on blueberry crop. Blueberry bushes were treated with BC17 or a control treatments prior to harvest and blueberries obtained therefrom were observed post-harvest. As control treatments, berries were either left untreated or treated with Lifegard (Certis), a combination of Stargus and Nufilm (Fertrell), or a sequential treatment of Bravo Weatherstik (Syngenta), Captevate (Aresta) and Pristine (Bayer). 50 berries were harvested and assessed for post-harvest decay caused by *B. cinerea* and *Colletotrichum* sp. after placement in humidity chambers at room temperature for 12-14 days.

Figure 12:
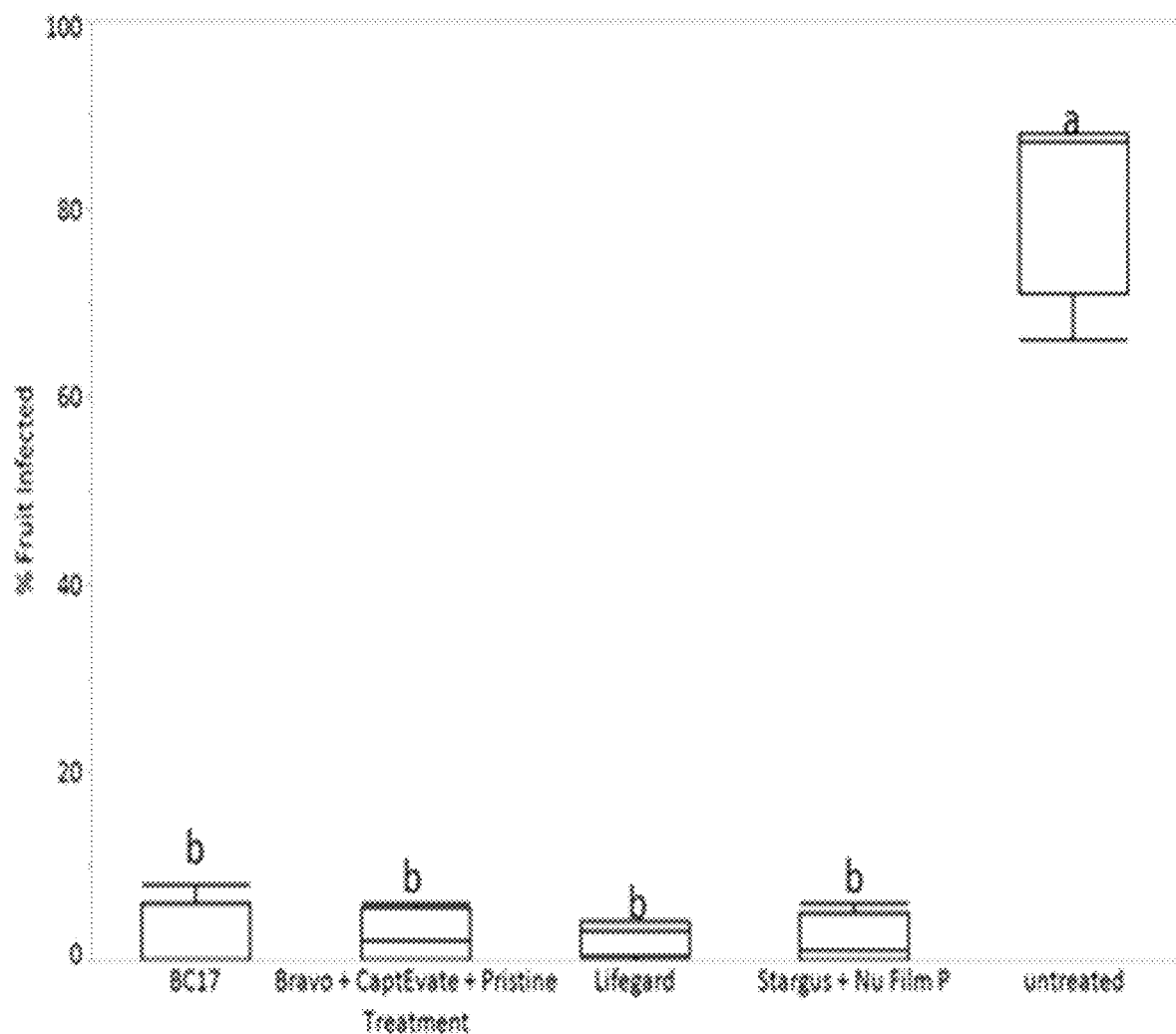
FIG. 12 illustrates the percent blueberries infected by *Botrytis* on treated and untreated plants.

Results expressed as % Fruit Infected are shown in FIG. 12. BC17 treated bushes had a 7% incidence of berry decay (FIG. 12), while untreated berries had a decay of 85%. (FIG. 12). BC17 was as effective as Bravo Weatherstik (Syngenta), Captevate (Aresta) and Pristine (Bayer), the commercial standard, in reducing post-harvest decay in blueberry crop (FIG. 12).

Data were analyzed through a one-way analysis of variance (ANOVA) and means were compared using Fisher's least significant difference (LSD). Box plots labeled with the same letter within each graph are not significantly different (LSD p=0.05).

Example 9

Evaluation of Efficacy of BC16 Against *Monilinia vaccinii-Corymbosi* Induced Mummyberry on Blueberry Crop BC16 was assessed for its efficacy against *Monilinia vaccinii-corynbosi* induced mummyberry on blueberry crop.

As control treatments, bushes were either left untreated or treated with a combination of Bravo Weatherstik (Syngenta), Indar 2F (Corteva Agriscience; active ingredient: fenbuconazole) and Pristine (Bayer). All treatment segments also received standard commercial fertility and insecticide program. The treatment products were mixed in a water volume of 75 gallons at 0.9 L/treatment or according to manufacturer's specifications and applied using a spray device to plants at regular intervals, approximately weekly. Bushes were treated at the different stages of growth including, early green tip (EGT), late green tip (LGT), pink bud (PB), bloom (BLM), petal fall (PF), green fruit (GRF), 10% blue fruit (BLF). The bushes were grown and maintained according to grower standard practice. Four replicates per treatment were conducted, in a randomized plot design format. Infection was assessed prior to fruit production and after berry production.

Figure 13A:
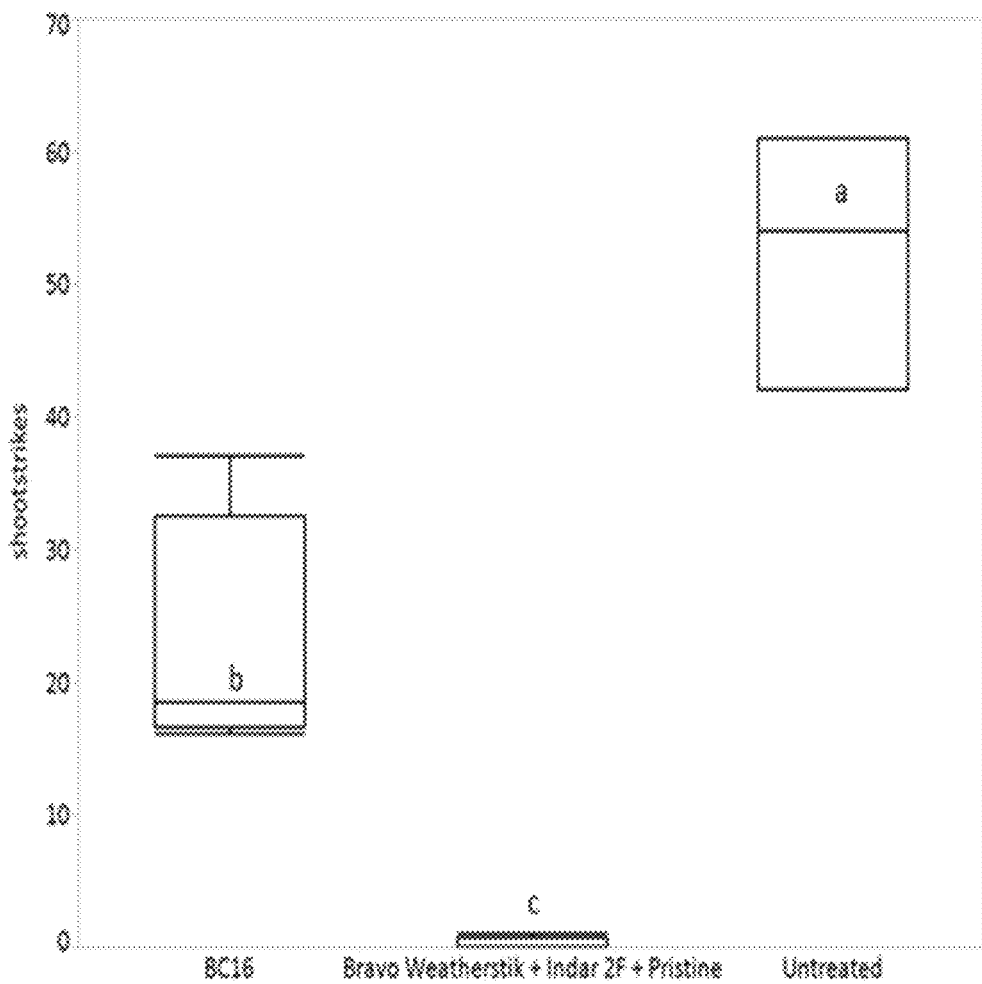
FIG. 13A illustrates the number of shootstrikes in treated and untreated blueberry bushes.

Mummyberry disease incidence due to *Monilinia vaccinn-coryrnbosi* infection was assessed by the presence of blueberry shoots affected by blight, commonly referred to as shootstrikes. The results, expressed as incidence of *M. vaccinn-corymbosi* induced shootstrikes (per Bush) are shown in FIG. 13A. Compared to untreated control, BC16 was effective at reducing the incidence of blossom blight by about 52%.

Figure 13B:
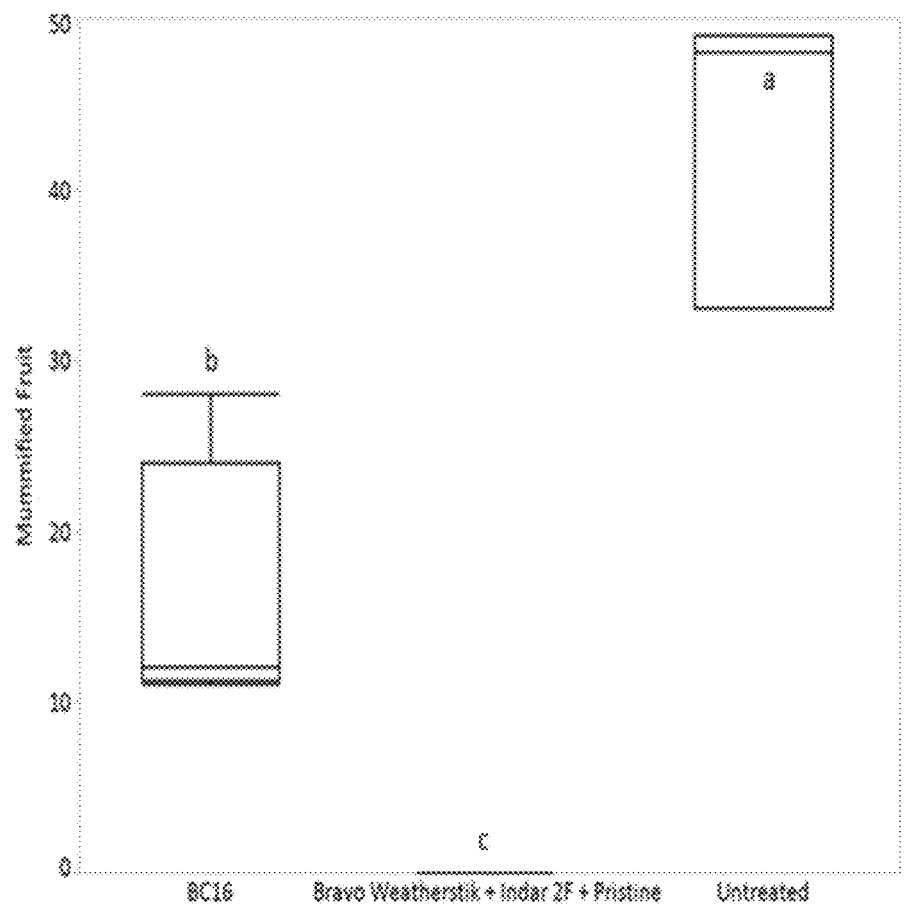
FIG. 13B illustrates the number of mummified fruit in treated and untreated blueberry bushes.

Incidence was also assessed by the mummified fruit phenotype characterized by the hardening and shriveling of infected berries. Blueberries dosed with BC16 were assessed for the presence of mummified fruit seven days after the crop attained the green fruit stage. The results, expressed as incidence of mummified fruit are shown in FIG. 13B. BC16 was effective at reducing the number of mummified fruit by about 59%, as compared to the untreated control.

All data were analyzed through a one-way analysis of variance (ANOVA) and means were compared using Fisher's least significant difference (LSD). Box plots labeled with the same letter within each graph are not significantly (LSD p=0.05).

Example 10

Evaluation of Efficacy of BC17 Against *Monilinia vaccinii-Corymbosi* Induced Mummyberry on Blueberry Crop BC17 was assessed for its efficacy against *Monilinia vaccinii-corynbosi* induced mummyberry on blueberry crop. Bushes were treated with BC17 or a control treatment. As control treatments, bushes were either left untreated or treated with a combination of Bravo Weatherstik (Syngenta), Indar 2F (Corteva Agriscience) and Pristine (BASF). All treatment segments also received standard commercial fertility and insecticide program. The treatment products were mixed in a water volume of 75 gallons at 0.9 L/treatment or according to manufacturer's specifications and applied using a spray device to plants at regular intervals. Bushes were treated at the different stages of growth including, early green tip (EGT), late green tip (LGT), pink bud (PB), bloom (BLM), petal fall (PF), green fruit (GRF), 10% blue fruit (BLF). Bushes were grown and maintained according to grower standard practice. Four replicates per treatment were conducted, in a randomized plot design format. Infection was assessed prior to fruit production and after berry production.

Figure 14A:
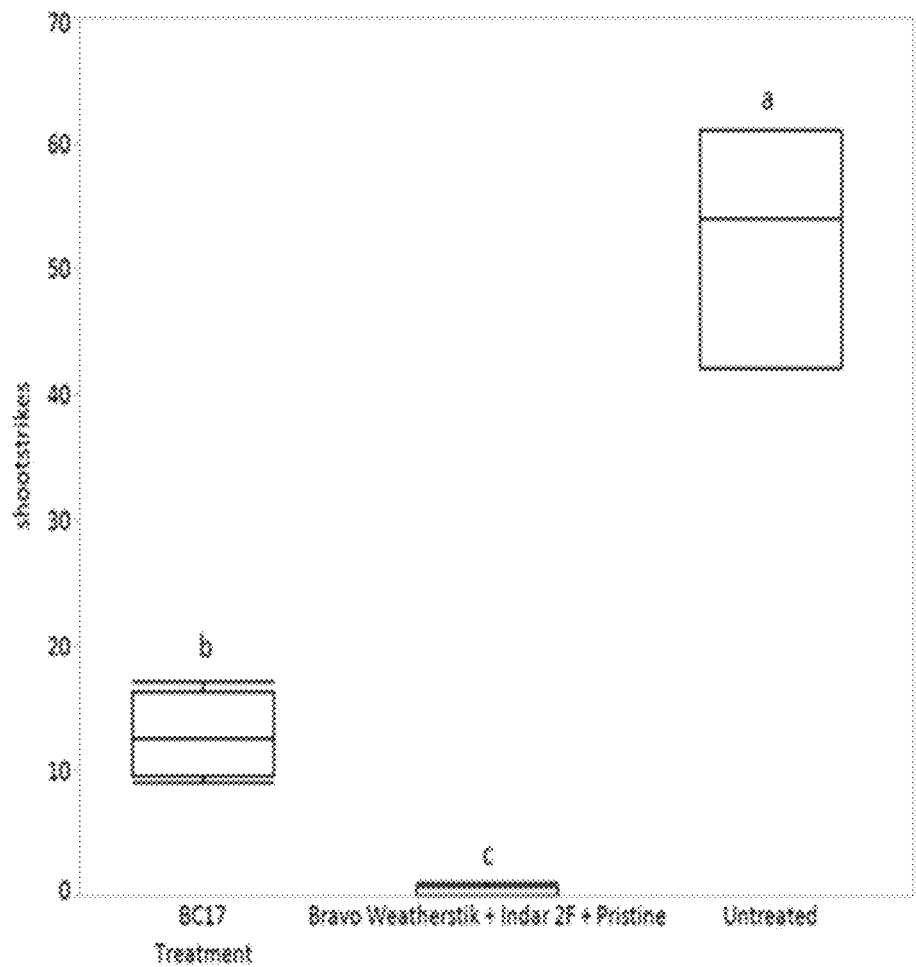
FIG. 14A illustrates the number of shootstrikes in treated and untreated blueberry bushes.

Mummyberry disease due to *Monilinia vaccinii-corymbosi* infection was assessed by the presence of blueberry shoots affected by blight, commonly referred to as shootstrikes. Results, expressed as incidence of shootstrikes per bush are shown in FIG. 14A. BC17 was effective at reducing the incidence of blossom blight by about 75% in comparison to untreated controls.

Figure 14B:
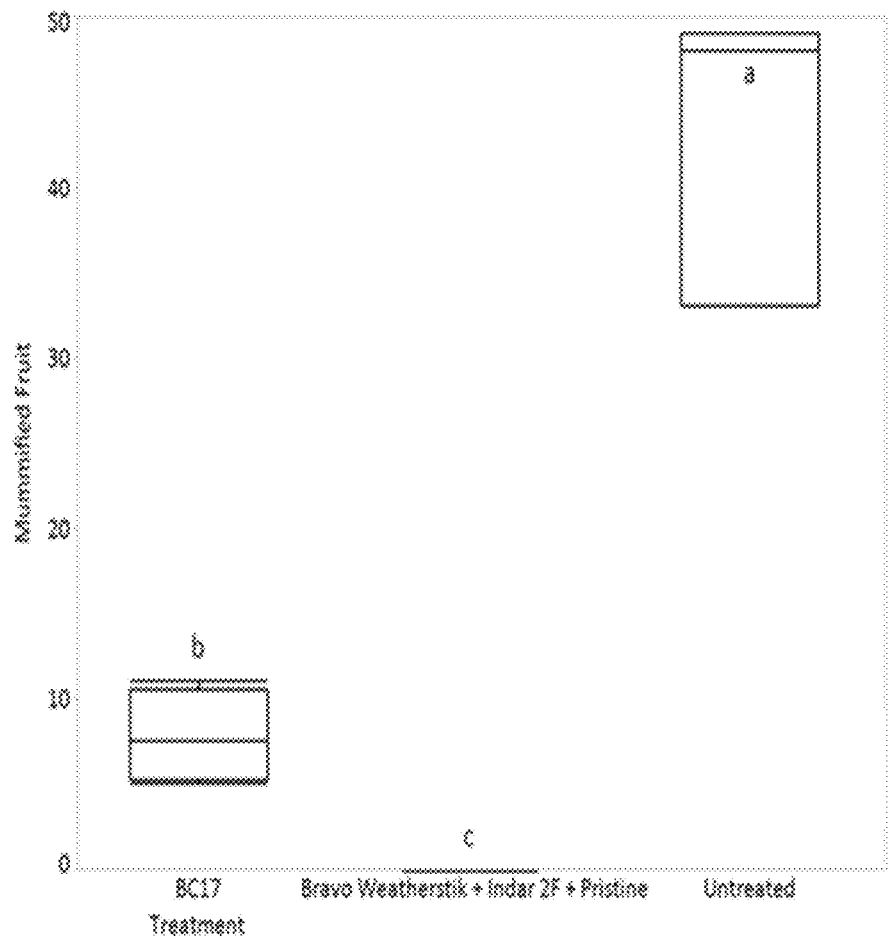
FIG. 14B illustrates the number of mummified fruit in treated and untreated blueberry bushes.

Disease incidence was also assessed by the mummified fruit phenotype characterized by the hardening and shriveling of infected berries. Blueberries dosed with BC17 were assessed for the presence of mummified fruit seven days after the crop attained the stage of green fruit. The results, expressed as incidence of mummified fruits are shown in FIG. 14B. BC17 was effective at reducing the number of mummified fruit by about 80% respectively, as compared to the untreated control.

All data were analyzed through a one-way analysis of variance (ANOVA) and means were compared using Fisher's least significant difference (LSD). Box plots labeled with the same letter within each graph are not significant (LSD p=0.05).

Example 11

Evaluation of Efficacy of BC8 Against Fungal Corn Pathogen *Puccinia sorghi*

BC8 was assessed for its efficacy against corn rust caused by the fungal pathogen *Puccinia sorghi* in corn crop. BC8 treatment consisted of three applications at the rate of 40 qt/acre at 7-10 day intervals. Two rows each of 20 feet length were treated with BC8 with one row preserved as buffer between treatment plots. Four replicates were conducted in each treatment protocol.

As control treatments, rows were either left untreated or treated Daconil SDG (Syngenta; active ingredient: chlorothalonil). All treatment segments also received standard commercial fertility and insecticide program. The bushes were grown and maintained according to grower standard practice.

The treatment products were mixed in a water volume of 20 gallons/acre and applied using a knapsack sprayer (7.5 foot boom with flat fan nozzles at 28 psi) to plants at regular intervals. Crops were treated at the beginning of the conventional timing (late June), or at first sign of disease (whichever occurred earlier).

Figure 15:
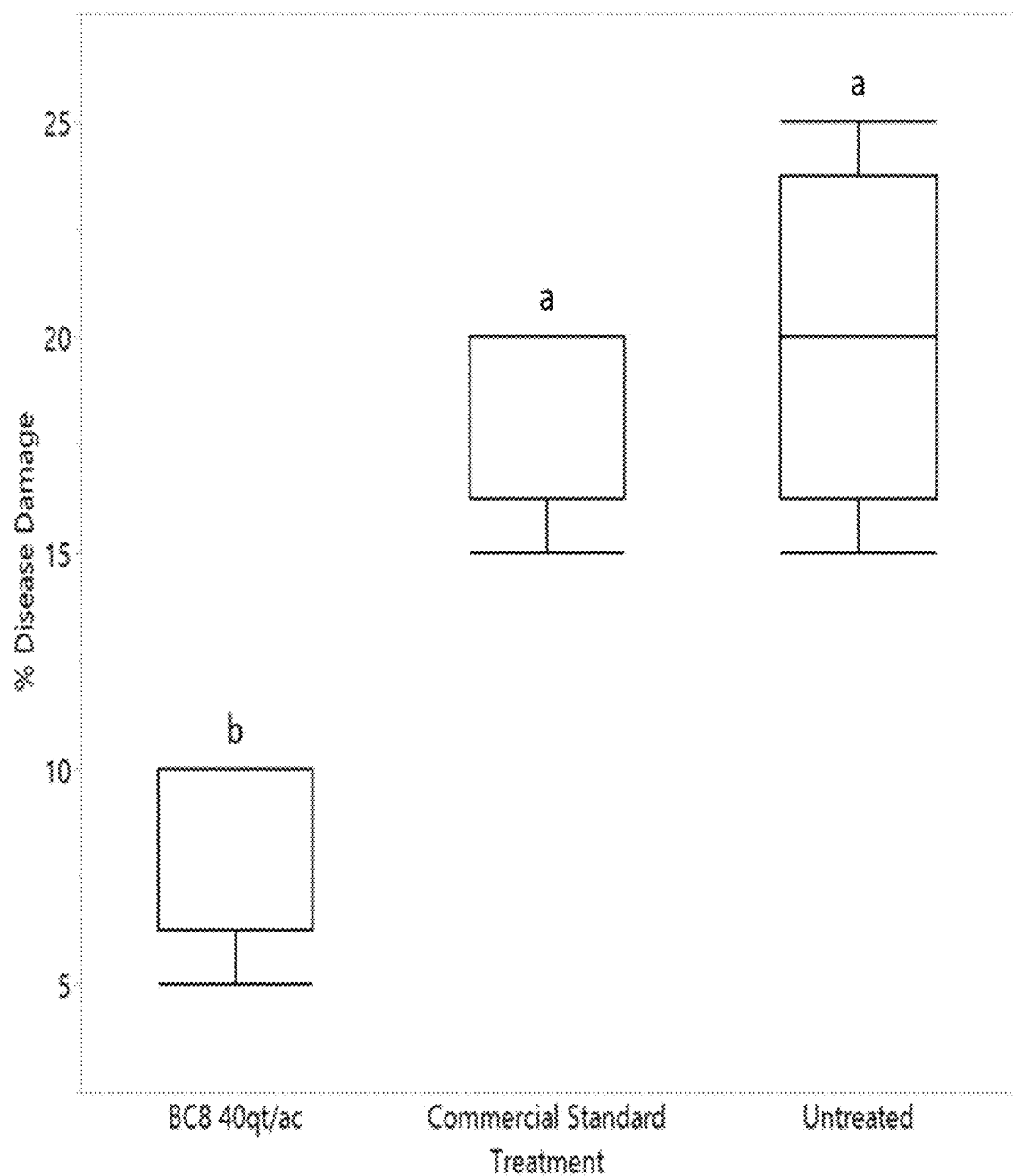
FIG. 15 illustrates the percent disease damage caused by corn rust in treated and untreated corn plants.

BC8 was effective at inhibiting rust and the damage caused by the disease in corn when compared to the untreated plots. The average disease damage in plots treated with BC8. 4 days after the last treatment was observed to be around 8.8% compared to untreated plots, where the disease damage was observed to be around 20% (FIG. 15). BC8 was more effective than the commercial treatment in inhibiting damage caused by corn rust in corn crop (FIG. 15).

All data were analyzed through a one-way analysis of variance (ANOVA) and means were compared using Fisher's least significant difference (LSD). Box plots labeled with the same letter within each graph are not significantly (LSD p=0.05).

Example 12

Evaluation of Efficacy of BC16 Against Fungal Corn Pathogen *Puccinia sorghi*

BC16 was assessed for its efficacy against corn rust caused by the fungal pathogen *Puccinia sorghi* in corn crop. BC16 treatment consisted of three applications at the rate of 20 qt/acre or 40 qt/acre at 7-10 day intervals. Two rows each of 20 feet length were treated with BC16 with one row preserved as buffer between treatment plots. Four replicates were conducted in each treatment protocol.

As control treatments, rows were either left untreated or treated Daconil SDG (Syngenta). All treatment segments also received standard commercial fertility and insecticide program. The corn crop was grown and maintained according to grower standard practice. The treatment products were mixed in a water volume of 20 gallons/acre and applied using a knapsack sprayer (7.5 foot boom with flat fan nozzles at 28 psi) to plants at regular intervals. Crops were treated at the beginning of the conventional timing (late June), or at first sign of disease (whichever occurred earlier).

Figure 16A:
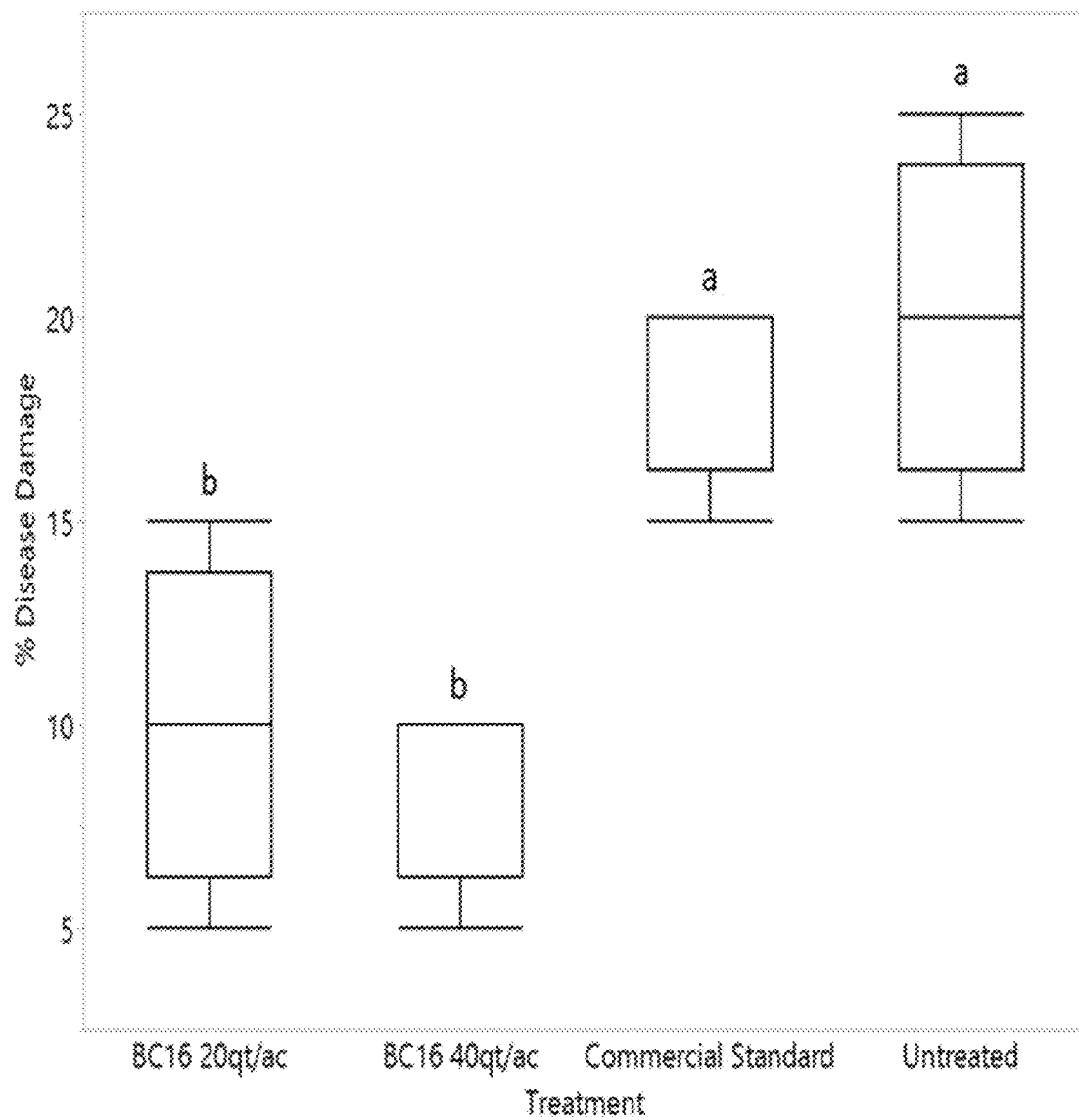
FIG. 16A illustrates the percent disease damage caused by corn rust in treated and untreated corn plants.

BC16 was effective at inhibiting rust and the damage caused by the disease in corn when compared to the untreated plots. The average disease damage in plots treated with BC16 at 20 qt/acre, 4 days after the last treatment, was observed to be around 10% compared to untreated plots, where the disease damage was observed to be around 20% (FIG. 16A). The average disease damage in plots treated with BC16 at 20 qt/acre, 4 days after the last treatment, was observed to be around 5% compared to untreated plots, where the disease damage was observed to be around 20% (FIG. 16A). BC16 was more effective in inhibiting damage caused by corn rust in corn crop than the standard commercial treatment (FIG. 16A).

Figure 16B:
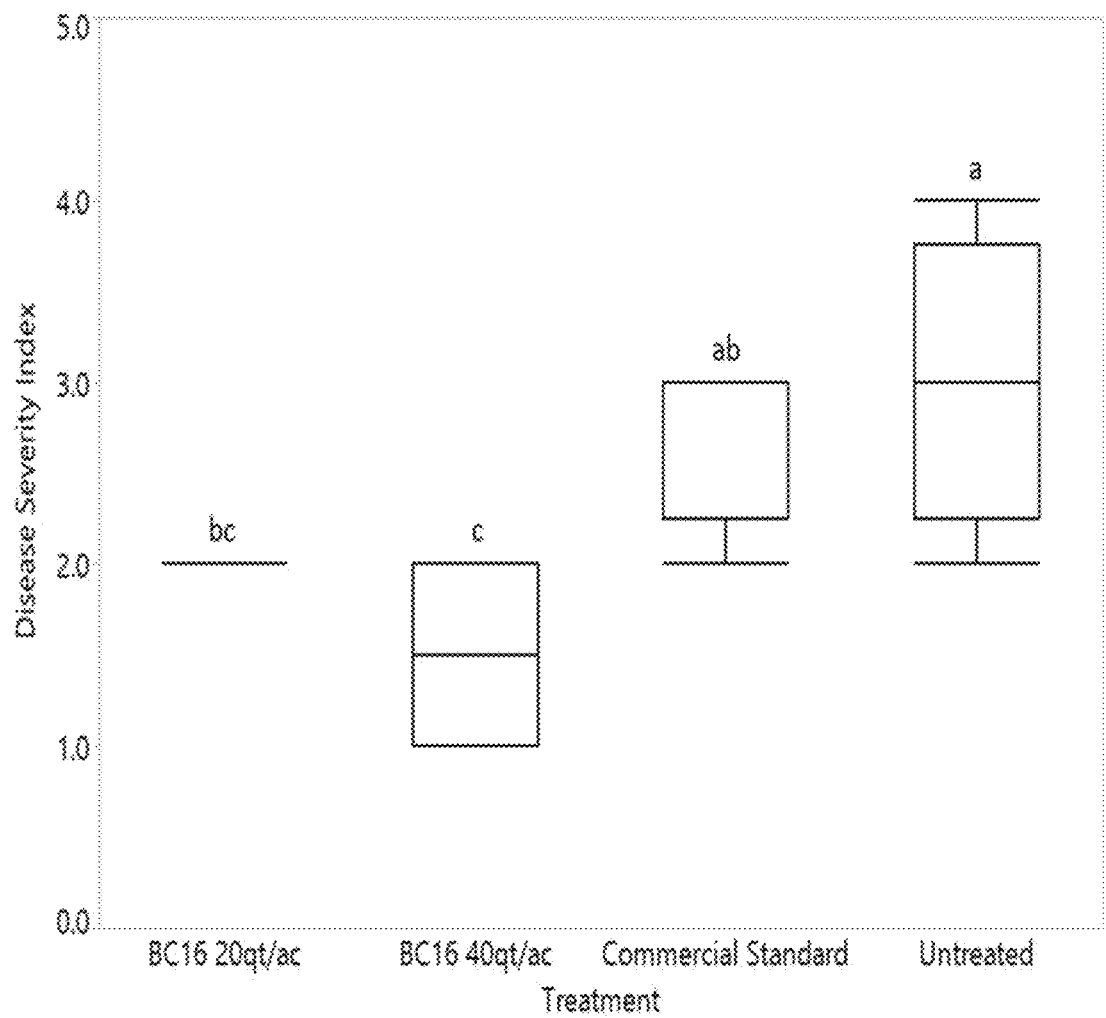
FIG. 16B illustrates the disease severity index of corn rust in treated and untreated corn plants.

Disease severity index was measured after three applications. Compared to untreated plots and plots treated with commercial standard, plots treated with BC16 at 20 qt/acre and at 40 qt/acre had reduced disease severity (FIG. 16B)

All data were analyzed through a one-way analysis of variance (ANOVA) and means were compared using Fisher's least significant difference (LSD). Box plots labeled with the same letter within each graph are not significantly different (LSD p=0.05).

Example 13

Evaluation of Efficacy of BC17 Against Fungal Corn Pathogen *Puccinia sorghi*

BC17 was assessed for its efficacy against corn rust caused by the fungal pathogen *Puccinia sorghi* in corn crop. BC17 treatment consisted of three applications at the rate of 20 qt/acre at 7-10 day intervals. Two rows each of 20 feet length were treated with BC17 with one row preserved as buffer between treatment plots. Four replicates were conducted in each treatment protocol.

As control treatments, bushes were either left untreated or treated Daconil SDG (Syngenta). All treatment segments also received standard commercial fertility and insecticide program. The bushes were grown and maintained according to grower standard practice. The treatment products were mixed in a water volume of 20 gallons/acre and applied using a knapsack sprayer (7.5 foot boom with flat fan nozzles at 28 psi) to plants at regular intervals. Crops were treated at the beginning of the conventional timing (late June), or at first sign of disease (whichever occurred earlier).

Figure 17A:
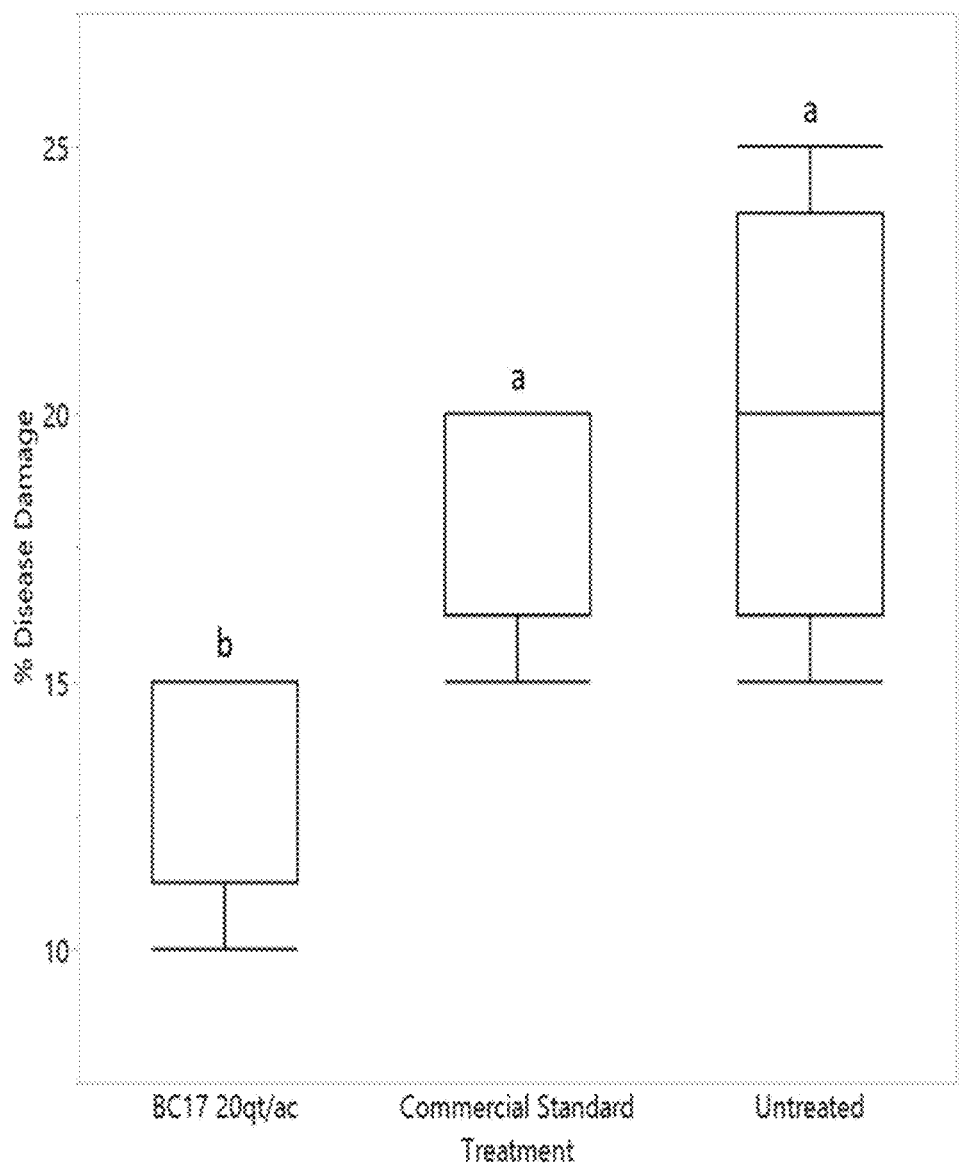
FIG. 17A illustrates the percent disease damage caused by corn rust in treated and untreated corn plants.

BC17 was effective at inhibiting corn rust and the damage caused by the disease in corn when compared to the untreated plots. The average disease damage in plots treated with BC17 at 20 qt/acre, 4 days after the last treatment, was observed to be around 10% compared to untreated plots, where the disease damage was observed to be around 20% (FIG. 17A). The average disease damage in plots treated with BC17 at 20 qt/acre, 4 days after the last treatment, was observed to be around 13.8% compared to untreated plots, where the disease damage was observed to be around 20% (FIG. 17A). BC17 was more effective in inhibiting damage caused by corn rust in corn crop than Daconil SDG (Syngenta), the standard commercial treatment (FIG. 17A).

Figure 17B:
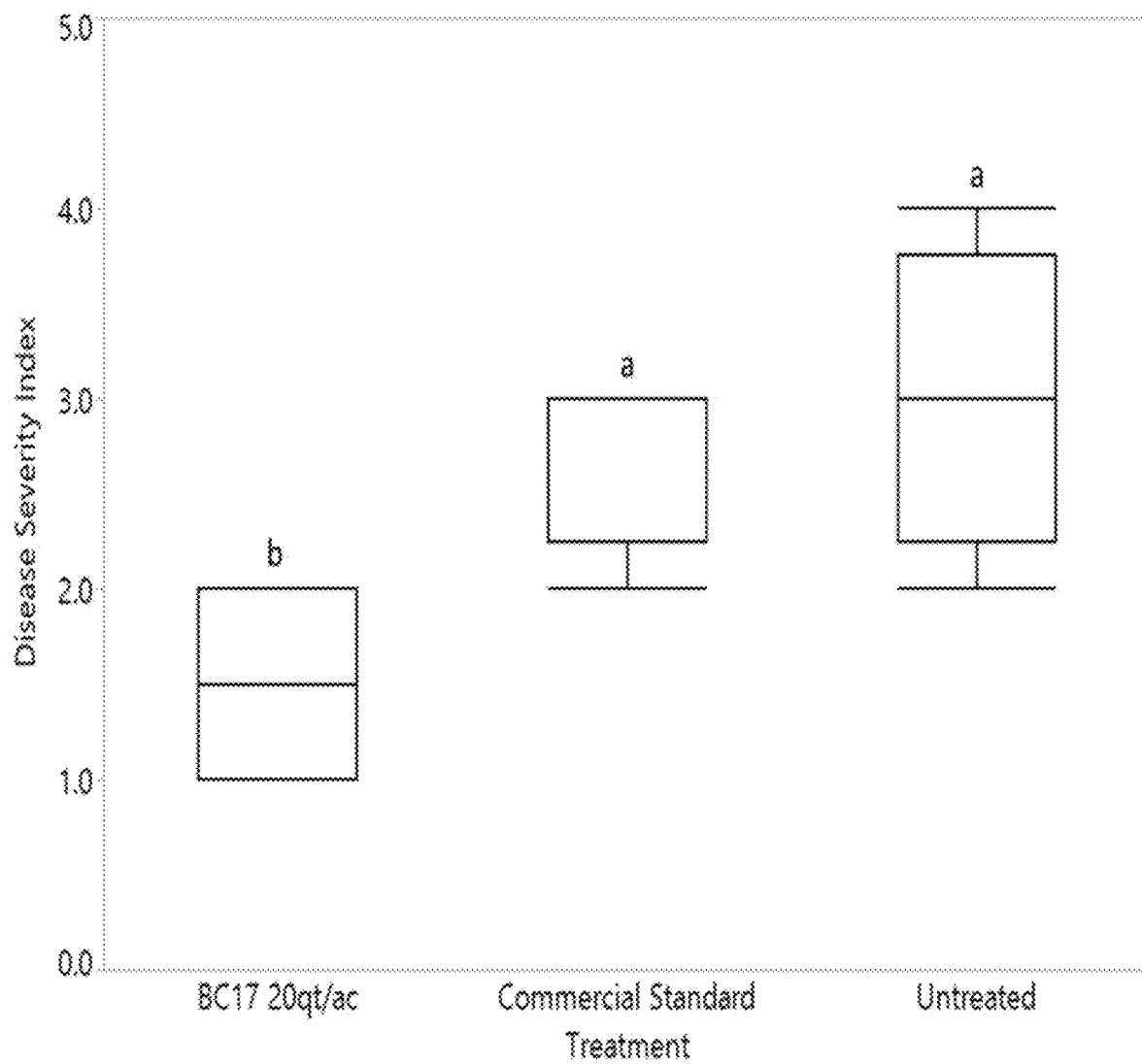
FIG. 17B illustrates the disease severity index of corn rust in treated and untreated corn plants.

Disease severity index was measured after three applications. Compared to untreated plots and the commercial standard treatment, plots treated with BC17 at 20 qt/acre had reduced disease severity (FIG. 17B)

All data were analyzed through a one-way analysis of variance (ANOVA) and means were compared using Fisher's least significant difference (LSD). Box plots labeled with the same letter within each graph are not significantly different (LSD p=0.05).

Example 14

Evaluation of Efficacy of BC8 Against *Plasmopara viticola* in Vignoles Grapes

Figure 18A:
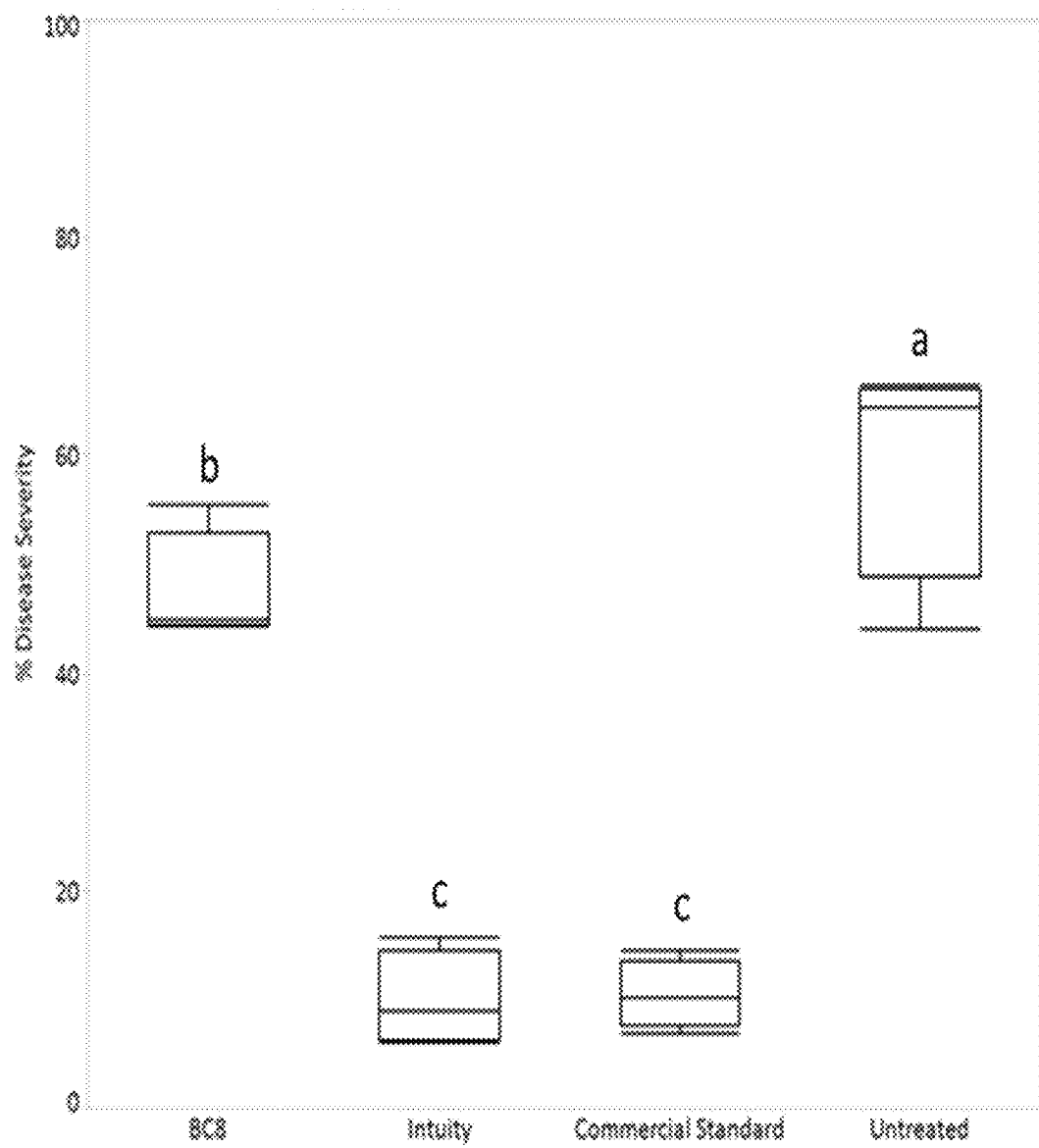
FIG. 18A illustrates the percent disease severity of downy mildew in treated and untreated grape leaves.
Figure 18B:
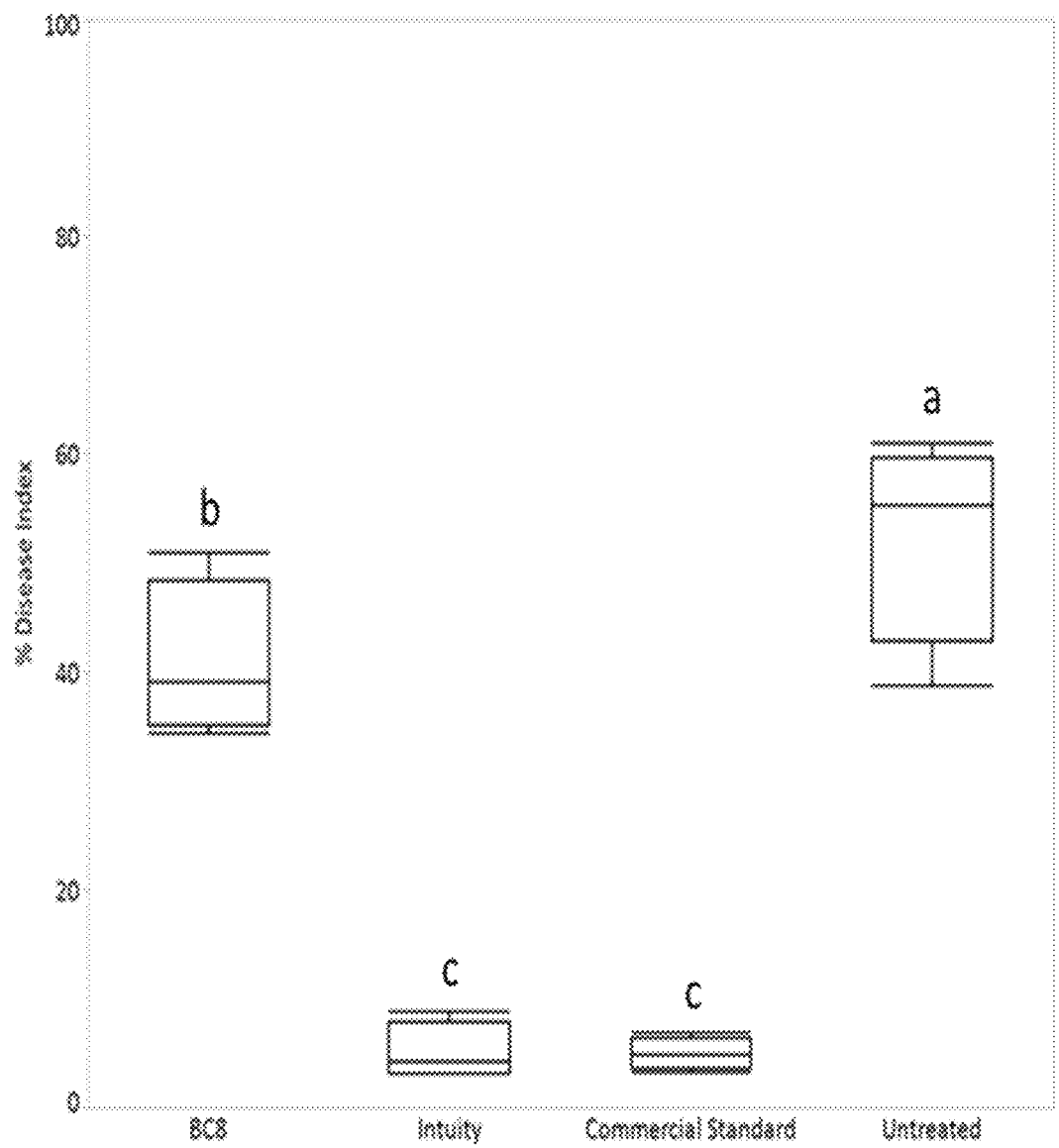
FIG. 18B illustrates the percent disease severity of downy mildew in treated and untreated grape leaves.

BC8 was assessed for its efficacy against the progression of downy mildew caused by *Plasmopara viticola* in Vignoles grapes. Vines were treated with either BC8 or a control treatment. BC8 treatment consisted of eight applications applied at 7-14 day intervals depending on growth stages. The first four applications were applied at the rate of 40 gallons/acre and the last four applications at the rate of 50 gallons/acre. As control treatments, vines were either left untreated or treated with a combination of RevusTop (Syngenta; active ingredients: madnipropamid, defenoconazole) and Intuity (Valent USA; active ingredient: mandestrobin) (referenced in FIG. 18A and FIG. 18B as Intuity), or a combination of Manzate (Keystone Pest Solutions; active ingredients: mancozeb) and Pristine (Bayer) (referenced in FIG. 18A and FIG. 18B as Commercial Standard). All treatment segments also received standard commercial fertility and insecticide program. The vines were grown and maintained according to grower standard practice. The treatment products were mixed in a water according to manufacturer's specifications and applied to the bushes using a Spray bloom device. Four experimental replicates were conducted for each treatment. A randomized plot design was adopted for the study.

BC8 treatment resulted in efficacious control of Downy mildew in leaves induced by *Plasmopara viticola*, shown by a reduction in both disease severity (FIG. 18A) and disease index (FIG. 18B), compared to leaves in untreated grape plants.

All data were analyzed through a one-way analysis of variance (ANOVA) and means were compared using Fisher's least significant difference (LSD). Box plots labeled with the same letter within each graph are not significantly different (LSD p=0.05).

Example 15

Evaluation of Efficacy of BC8 Against Rot Caused by *Botrytis cinerea* in Vignoles Grapes BC8 was assessed for its efficacy against rot caused by *Botrytis cinerea* in Vignoles grapes.

Figure 19A:
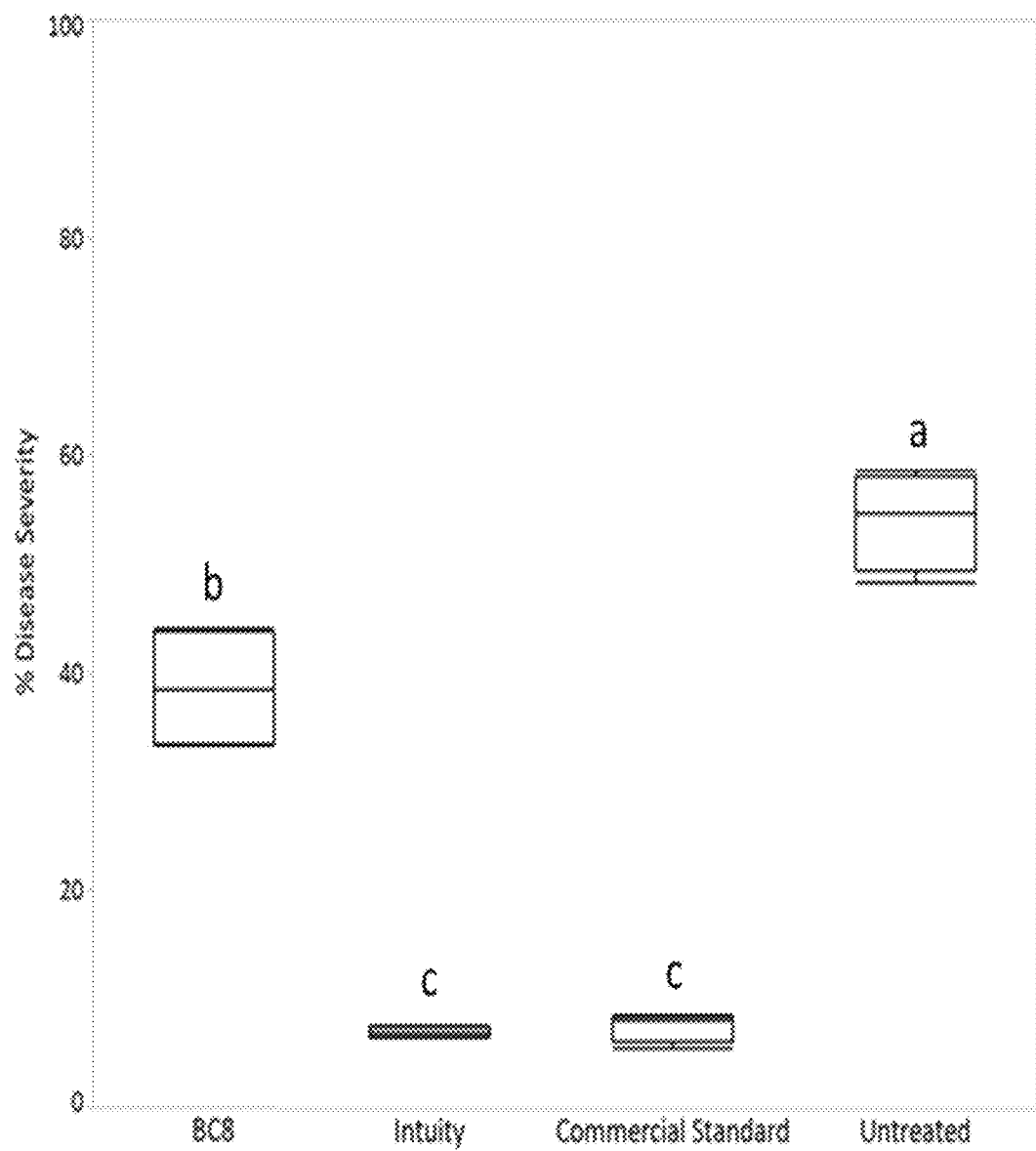
FIG. 19A illustrates the percent disease severity of *Botrytis* in treated and untreated grape bunches.
Figure 19B:
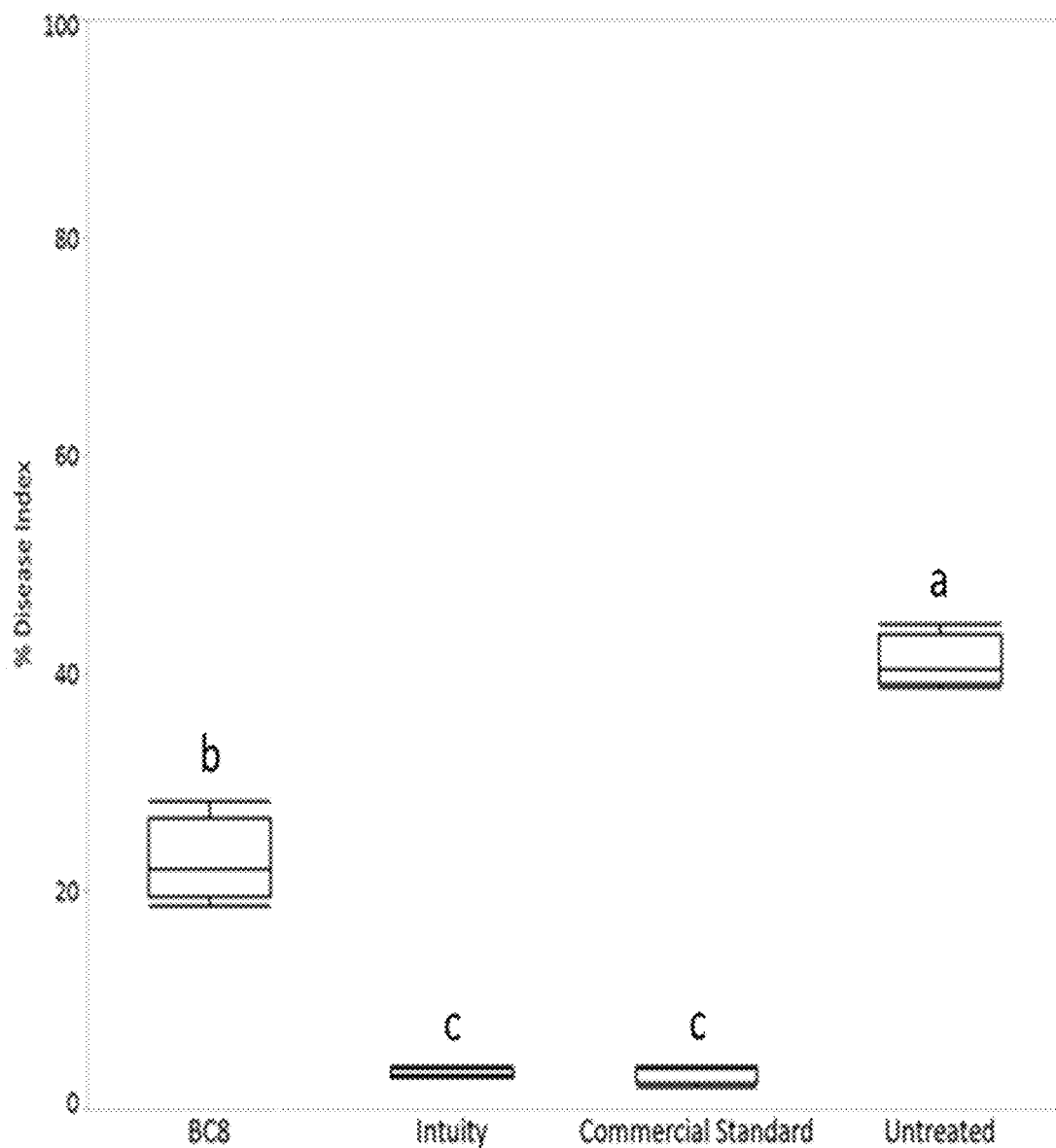
FIG. 19B illustrates the percent disease index of *Botrytis* in treated and untreated grape bunches.

Vines were treated with either BC8 or a control treatment. BC8 treatment consisted of eight application applied at 7-14 day intervals depending on growth stages. The first four applications were applied at the rate of 40 gallons/acre and the last four applications were at the rate of 50 gallons/acre. As control treatments, vines were either left untreated or treated with a combination of RevusTop (Syngenta) and Intuity (Valent USA) (referenced in FIG. 19A and FIG. 19B as Intuity), or a combination of Manzate (Keystone Pest Solutions) and Pristine (Bayer) (referenced in FIG. 19A and FIG. 19B as Commercial Standard). All treatment segments also received standard commercial fertility and insecticide program. Vines were grown and maintained according to grower standard practice.

The treatment products were mixed in water according to manufacturer's instruction applied to the vines using a Spray bloom device. Four experimental replicates were conducted for each treatment. A randomized plot design was adopted for the study. In total, 4 replicates were performed with 3 vines per plot.

BC8 treatment resulted in an effective control of rot induced by *Botrytis cinerea* cinerea in grape bunches, shown by a reduction in both disease severity by nearly 32% (FIG. 19A) and a reduction in disease index by about 50% (FIG. 19B), compared to untreated grape bunches.

All data were analyzed through a one-way analysis of variance (ANOVA) and means were compared using Fisher's least significant difference (LSD). Box plots labeled with the same letter within each graph are not significantly different (LSD p=0.05).

Example 16

Figure 20A:
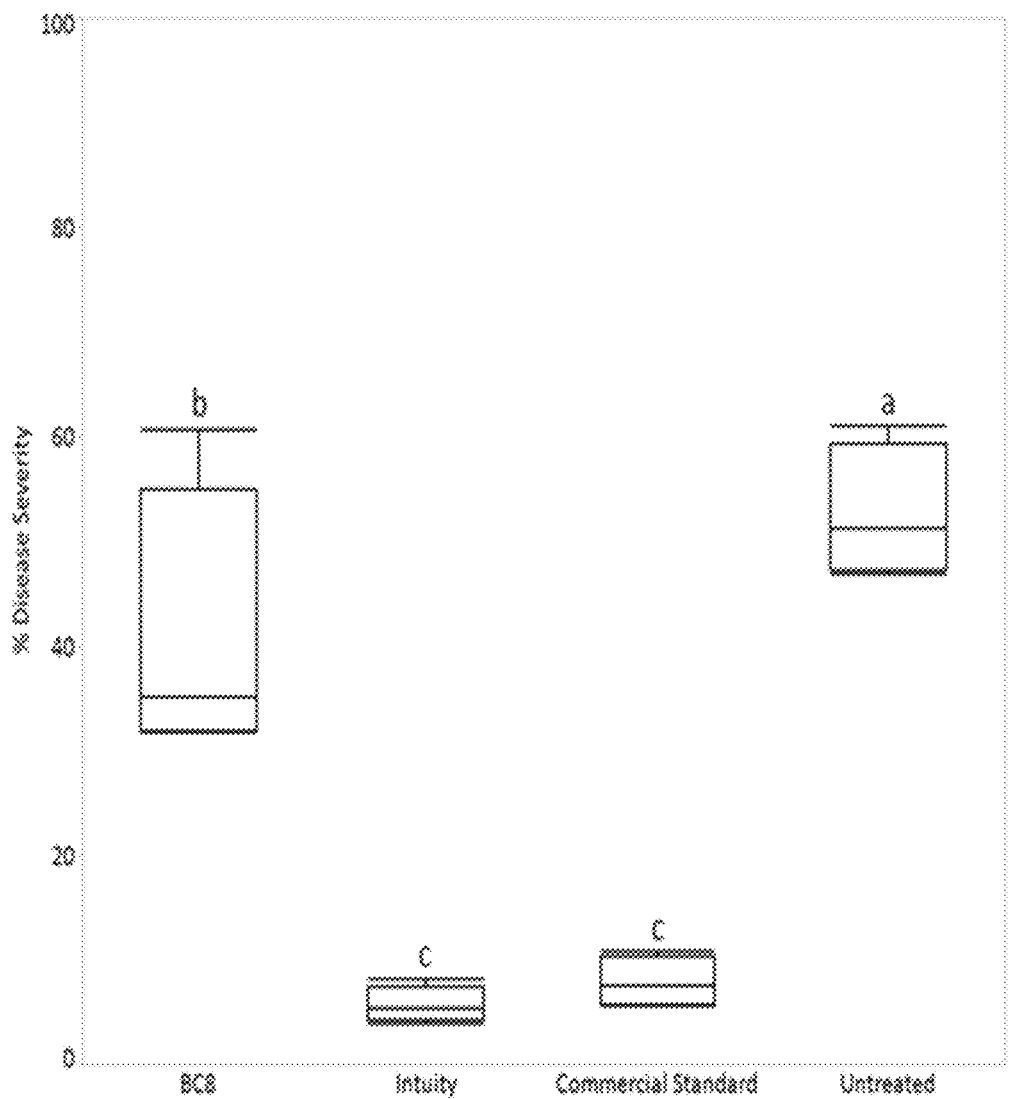
FIG. 20A illustrates the percent disease severity of powdery mildew in treated and untreated grape leaves.
Figure 20B:
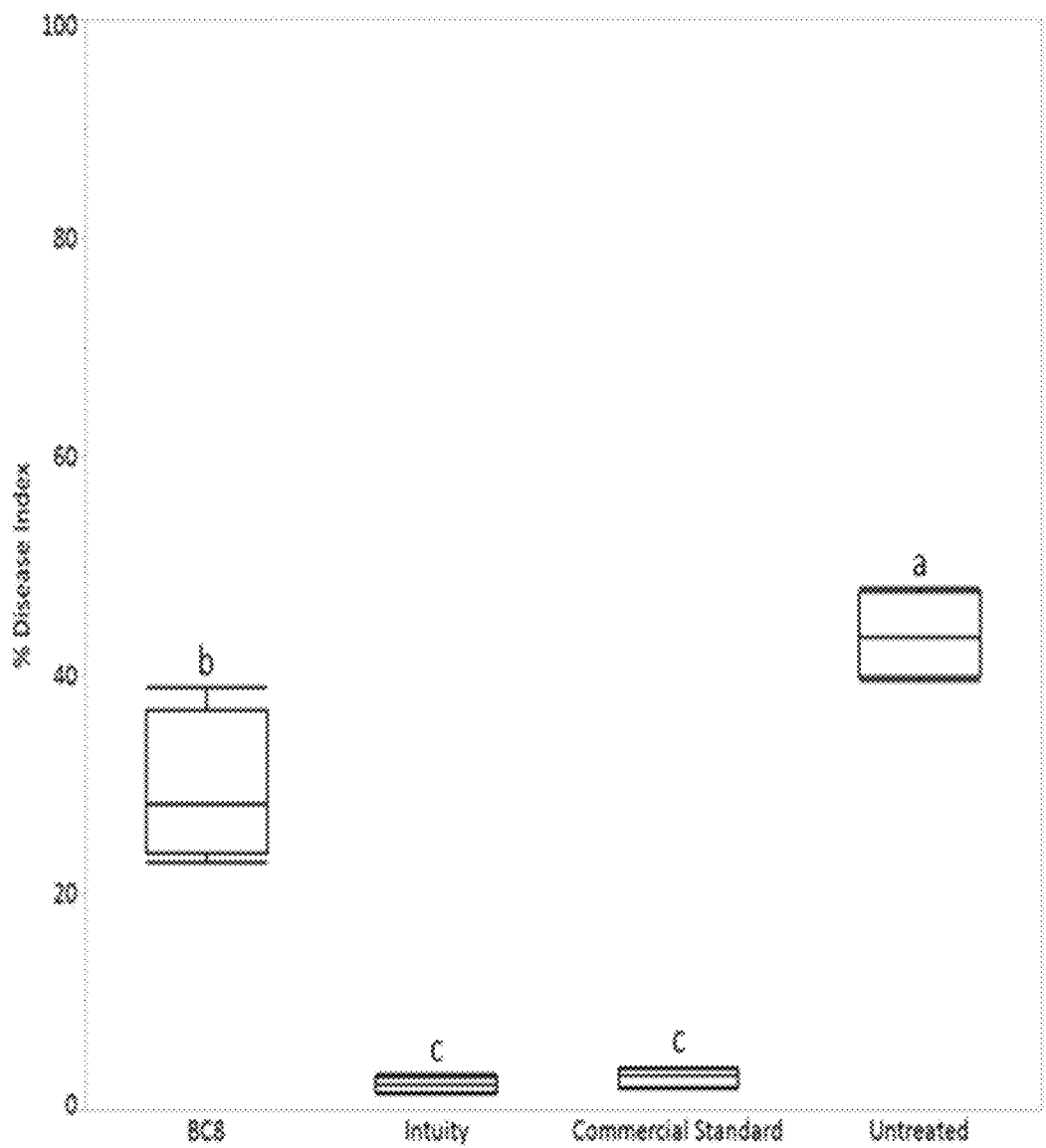
FIG. 20B illustrates the percent disease index of powdery mildew in treated and untreated grape leaves.

Evaluation of Efficacy of BC8 Against Powdery Mildew Induced by *Erysiphe necator* in Vignoles Grapes BC8 was assessed for its efficacy against powdery mildew caused by *Erysiphe necator* in Vignoles grapes. Vines were treated with either BC8 or a control treatment. BC8 treatment consisted of eight applications applied at 7-14 day intervals depending on growth stages. The first four applications were applied at the rate of 40 gallons/acre and the last four applications were applied at the rate of 50 gallons/acre. As control treatments, vines were either left untreated or treated with a combination of RevusTop (Syngenta) and Intuity (Valent USA) ("Intuity" in FIG. 20A and FIG. 20B), or a combination of Manzate (Keystone Pest Solutions) and Pristine (Bayer) ("Commercial Standard" in FIG. 20A and FIG. 20B). All treatment segments also received standard commercial fertility and insecticide program. Grapes were grown and maintained according to grower standard practice.

The treatment products were mixed in water according to manufacturer's specification and applied to the vines using a Spray bloom device. Four experimental replicates were conducted for each treatment. A randomized plot design was adopted for the study.

BC8 treatment reduced powdery mildew induced by *Erysiphe necator* in grape leaves, shown by a reduction in both disease severity by nearly 30% (FIG. 20A) and a reduction in disease index by about 50% (FIG. 20B), compared to leaves in untreated grape bunches.

All data were analyzed through a one-way analysis of variance (ANOVA) and means were compared using Fisher's least significant difference (LSD). Box plots labeled with the same letter within each graph are not significantly different (LSD p=0.05).

Example 17

Evaluation of Efficacy of BC16 Against *Plasmopara viticola* in Vignoles Grapes

Figure 21A:
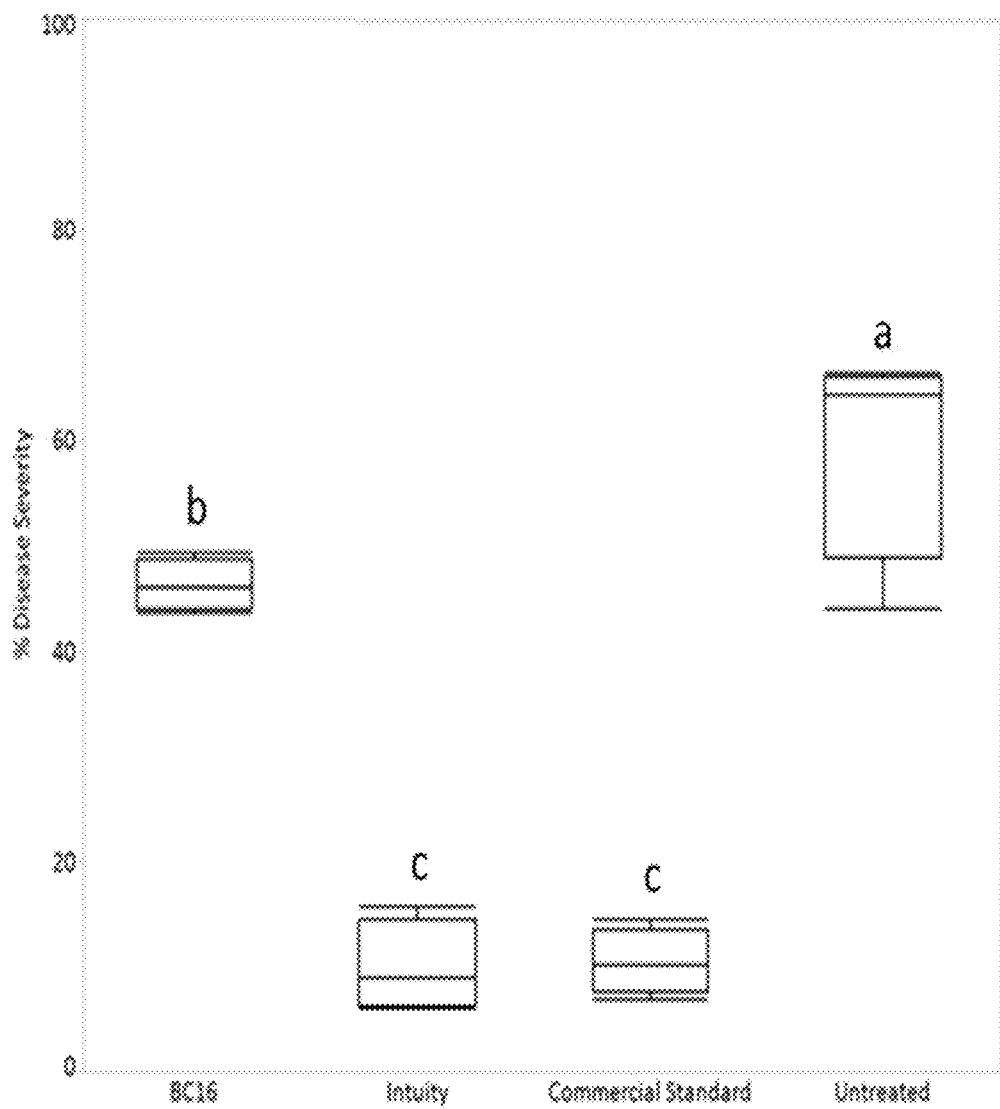
FIG. 21A illustrates the percent disease severity of downy mildew in treated and untreated grape leaves.
Figure 21B:
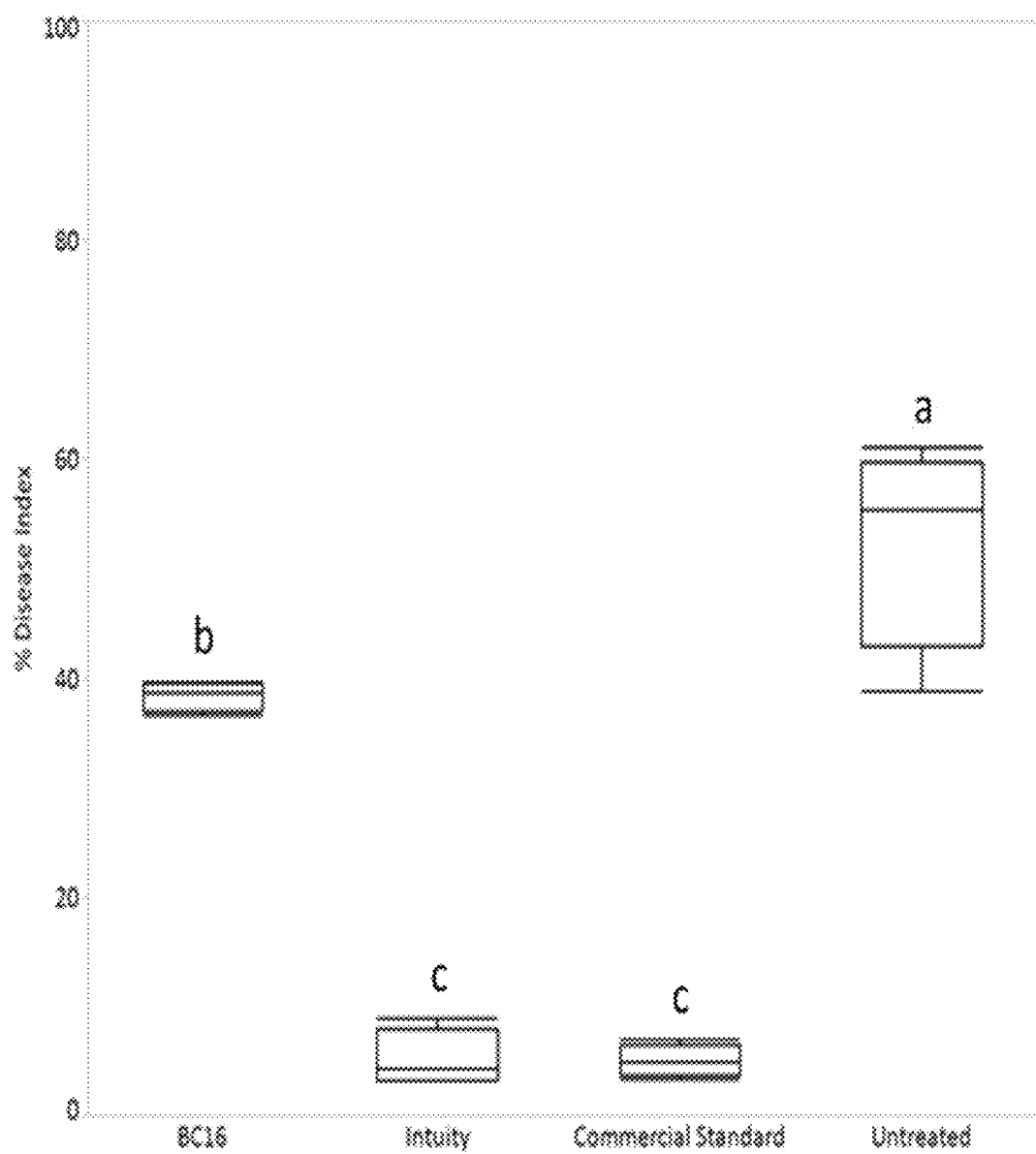
FIG. 21B illustrates the percent disease index of downy mildew in treated and untreated grape leaves.

BC16 was assessed for its efficacy against the progression of downy mildew caused by *Plasmopara viticola* in Vignoles grapes. Vines were treated with either a BC16 or a control treatment. BC16 treatment consisted of eight applications applied at 7-14 day intervals depending on growth stages. The first four applications were applied at the rate of 40 gallons/acre and the last four applications at the rate of 50 gallons/acre. As control treatments, vines were either left untreated or treated with a combination of RevusTop (Syngenta) and Intuity (Valent USA) ("Intuity" in FIG. 21A and FIG. 21B), or a combination of Manzate (Keystone Pest Solutions) and Pristine (Bayer) ("Commercial Standard" in FIG. 21A and FIG. 21B). All treatment segments also received standard commercial fertility and insecticide program. The grapes were grown and maintained according to grower standard practice.

The treatment products were mixed in water according to manufacturer's specifications and applied to the vine s using a Spray bloom device. Four experimental replicates were conducted for each treatment. A randomized plot design was adopted for the study.

BC16 treatment reduced Downy mildew in leaves induced by *Plasmopara viticola*, shown by a reduction in both disease severity (FIG. 21A) and disease index (FIG. 21B), compared to leaves in untreated grape plants.

All data were analyzed through a one-way analysis of variance (ANOVA) and means were compared using Fisher's least significant difference (LSD). Box plots labeled with the same letter within each graph are not significantly different (LSD p=0.05).

Example 18

Figure 22:
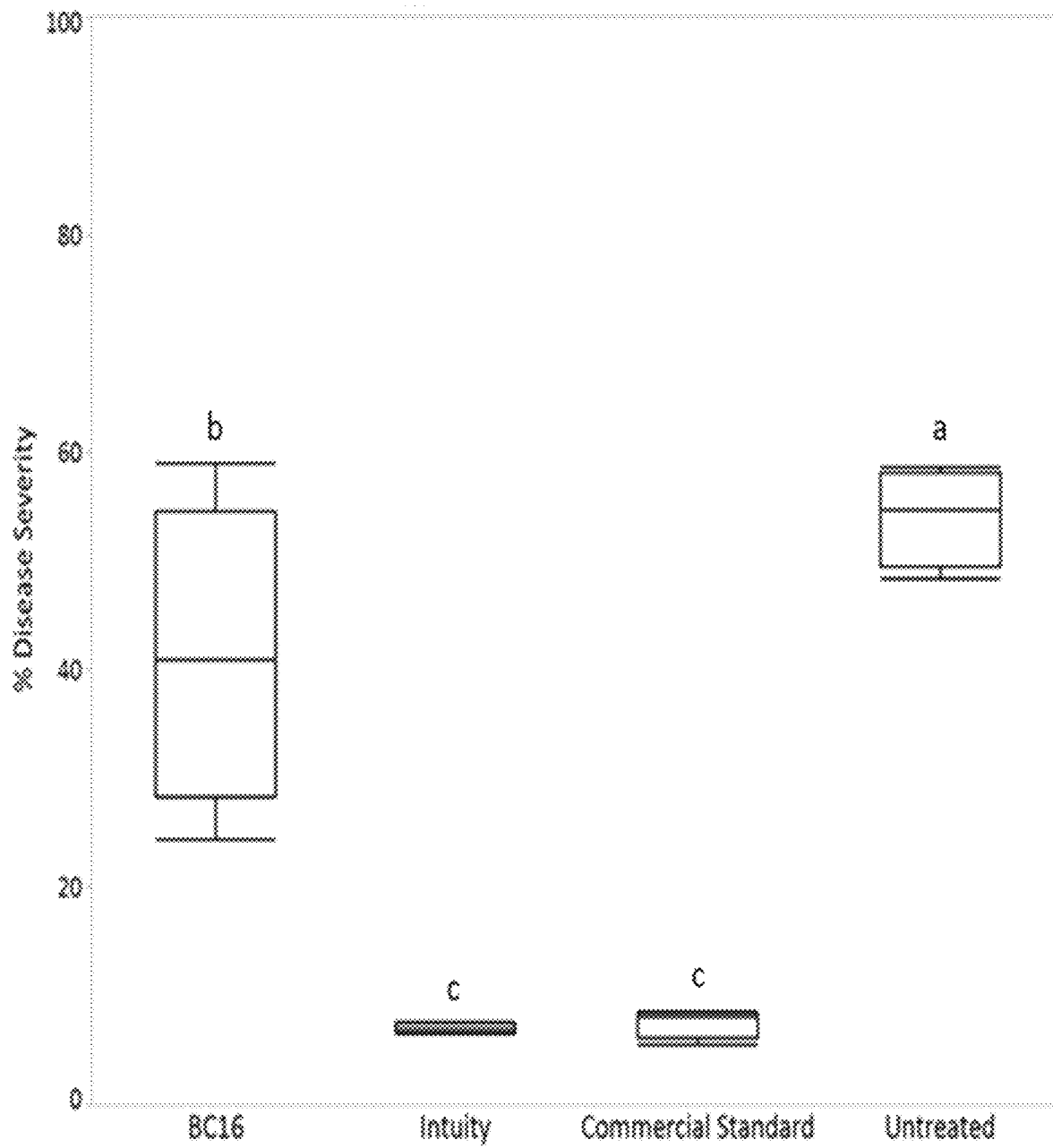
FIG. 22 illustrates the percent disease severity of *Botrytis* in treated and untreated grape bunches.

Evaluation of Efficacy of BC16 Against Rot Caused by *Botrytis cinerea* in Vignoles Grapes BC16 was assessed for its efficacy against rot caused by *Botrytis cinerea* cinerea in Vignoles grapes. Vines were treated with BC16 or a control treatment. BC16 treatment consisted of eight applications applied at 7-14 day intervals depending on growth stages. The first four applications were applied at the rate of 40 gallons/acre and the last four applications were at the rate of 50 gallons/acre. As control treatments, vines were either left untreated or treated with a combination of RevusTop (Syngenta) and Intuity (Valent USA) ("Intuity" in FIG. 22), or a combination of Manzate (Keystone Pest Solutions) and Pristine (Bayer) ("Commercial Standard" in FIG. 22). All treatment segments also received standard commercial fertility and insecticide program. Vines were grown and maintained according to grower standard practice.

The treatment products were mixed in water according to manufacturer's specifications and applied to the vines using a Spray bloom device. Four experimental replicates were conducted for each treatment. A randomized plot design was adopted for the study.

BC16 treatment inhibited rot induced by *Botrytis cinerea* in grape bunches, shown by a reduction in both disease severity by nearly 32% (FIG. 22), compared to untreated grape bunches.

All data were analyzed through a one-way analysis of variance (ANOVA) and means were compared using Fisher's least significant difference (LSD). Box plots labeled with the same letter within each graph are not significantly different (LSD p=0.05).

Example 19

Figure 23A:
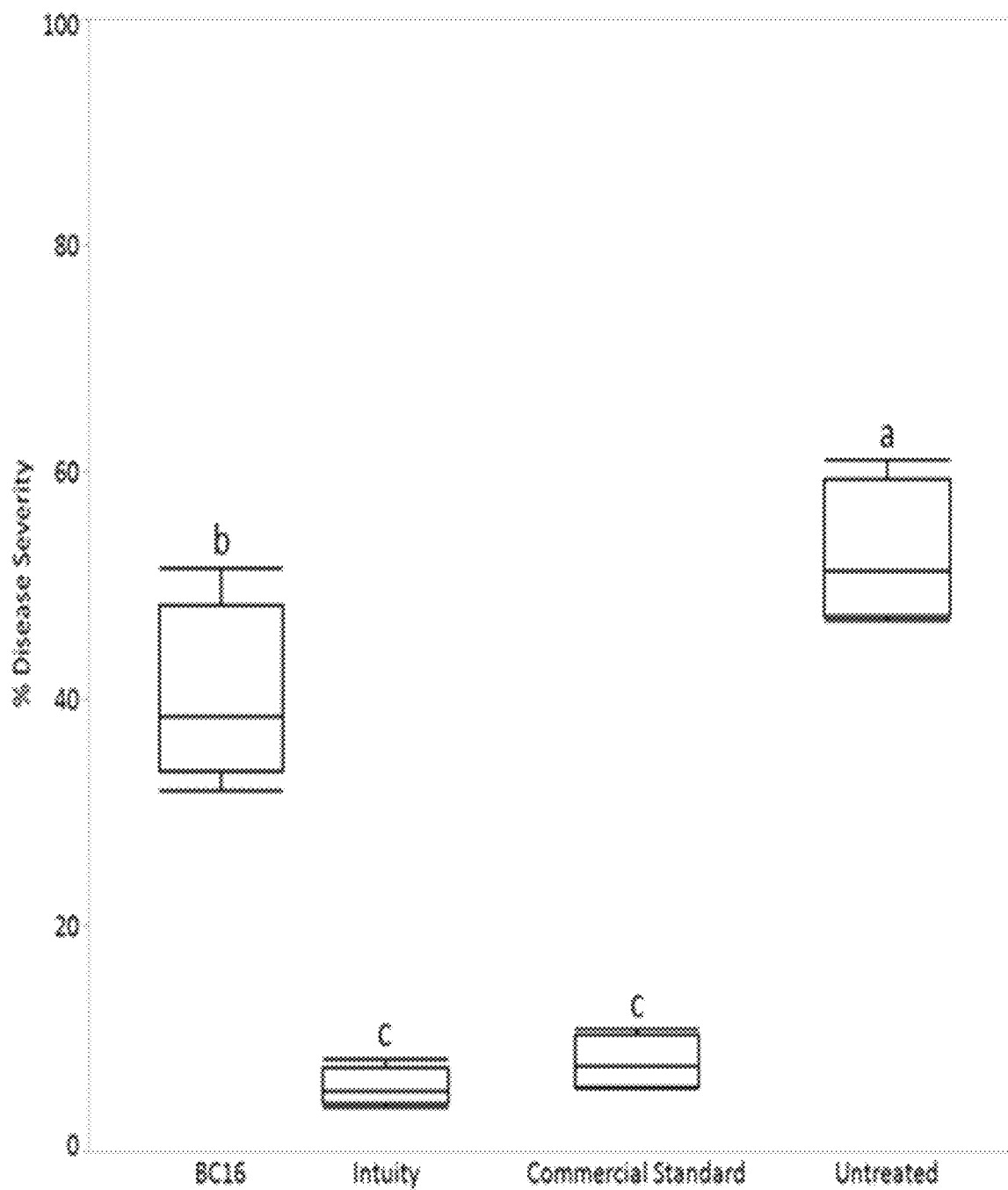
FIG. 23A illustrates the percent disease severity of downy mildew in treated and untreated grape leaves.
Figure 23B:
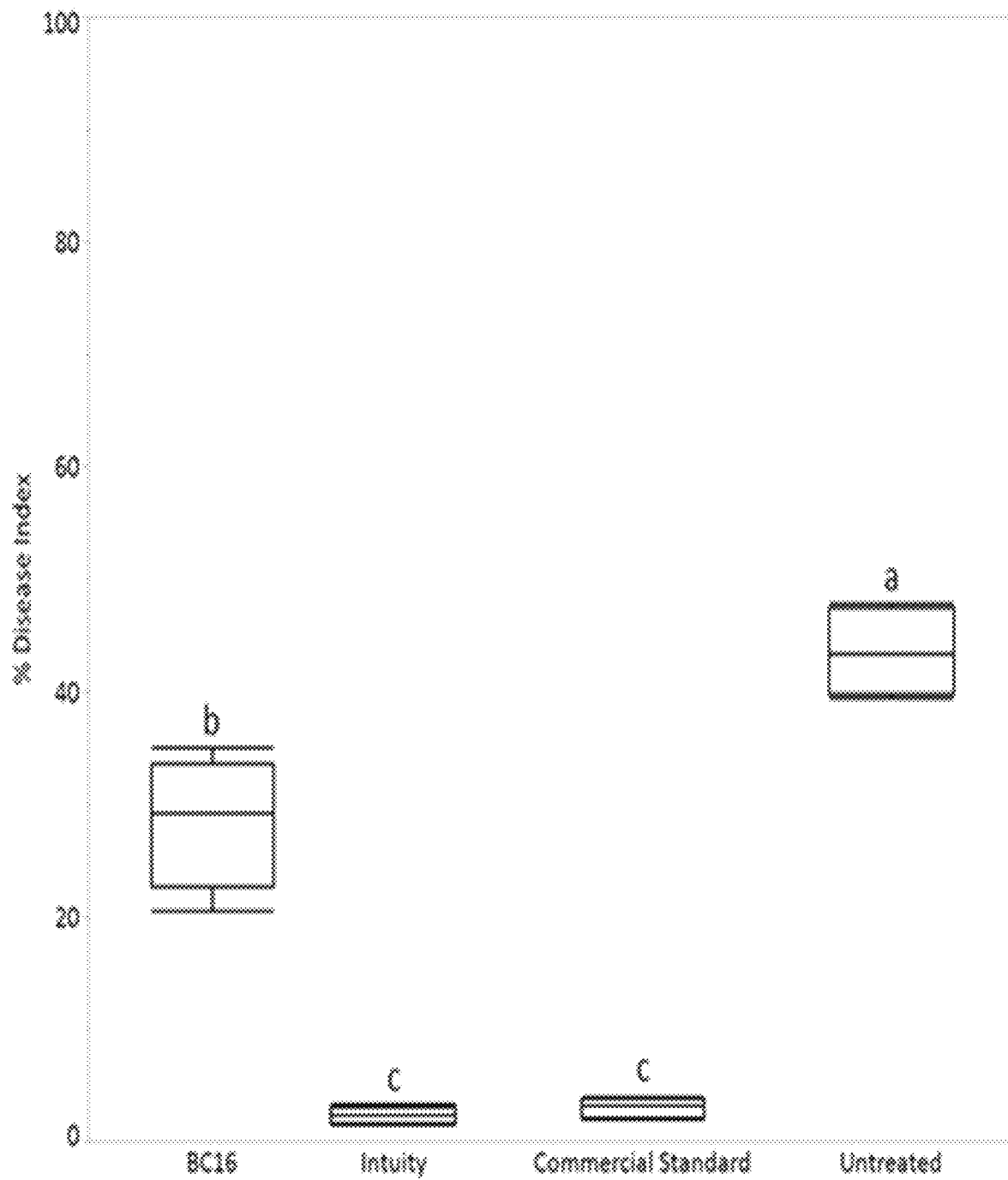
FIG. 23B illustrates the percent disease index of downy mildew in treated and untreated grape leaves.

Evaluation of Efficacy of BC16 Against Powdery Mildew Induced by *Erysiphe necator* in Vignoles Grapes BC16 was assessed for its efficacy against powdery mildew caused by *Erysiphe necator* in Vignoles grapes. Vines were treated with either a BC16 treatment or a control treatment. BC16 treatment consisted of eight applications applied at 7-14 day intervals depending on growth stages. The first four applications were applied at the rate of 40 gallons/acre and the last four applications were applied at the rate of 50 gallons/acre. As control treatments, vines were either left untreated or treated with a combination of Revus-Top (Syngenta) and Intuity (Valent USA) (referred to as "Intuity" in FIG. 23A and FIG. 23B), or a combination of Manzate (Keystone Pest Solutions) and Pristine (Bayer) ("Commercial Standard" in FIG. 23A and FIG. 23B). All treatment segments also received standard commercial fertility and insecticide program. Vines were grown and maintained according to grower standard practice.

The treatment products were mixed in water according to manufacturer's specification and applied to the vines using a Spray bloom device. Four experimental replicates were conducted for each treatment. A randomized plot design was adopted for the study.

BC16 treatment reduced the severity of powdery mildew induced by *Erysiphe necator* in grape leaves (FIG. 23A) leading to a reduction in disease index by about 30% (FIG. 23B), compared to leaves in untreated grape bunches.

All data were analyzed through a one-way analysis of variance (ANOVA) and means were compared using Fisher's least significant difference (LSD). Box plots labeled with the same letter within each graph are not significantly different (LSD p=0.05).

Example 20

Evaluation of Efficacy of BC18 Against *Plasmopara viticola* in Vignoles Grapes

BC18 was assessed for its efficacy against the progression of downy mildew caused by *Plasmopara viticola* in Vignoles grapes. Vines were treated with either BC18 or a control treatment. BC18 treatment consisted of eight applications applied at 7-14 day intervals depending on growth stages. The first four applications were applied at the rate of 40 gallons/acre and the last four applications at the rate of 50 gallons/acre. As control treatments, vines were either left untreated or treated with a combination of RevusTop (Syngenta) and Intuity (Valent USA) ("Intuity" in FIG. 24A and FIG. 24B), or a combination of Manzate (Keystone Pest Solutions) and Pristine (Bayer) ("Commercial Standard" in FIG. 24A and FIG. 24B). All treatment segments also received standard commercial fertility and insecticide program. The vines were grown and maintained according to grower standard practice.

The treatment products were mixed in water according to manufacturer's specification and applied to the vines using a Spray bloom device. Four experimental replicates were conducted for each treatment. A randomized plot design was adopted for the study.

Figure 24A:
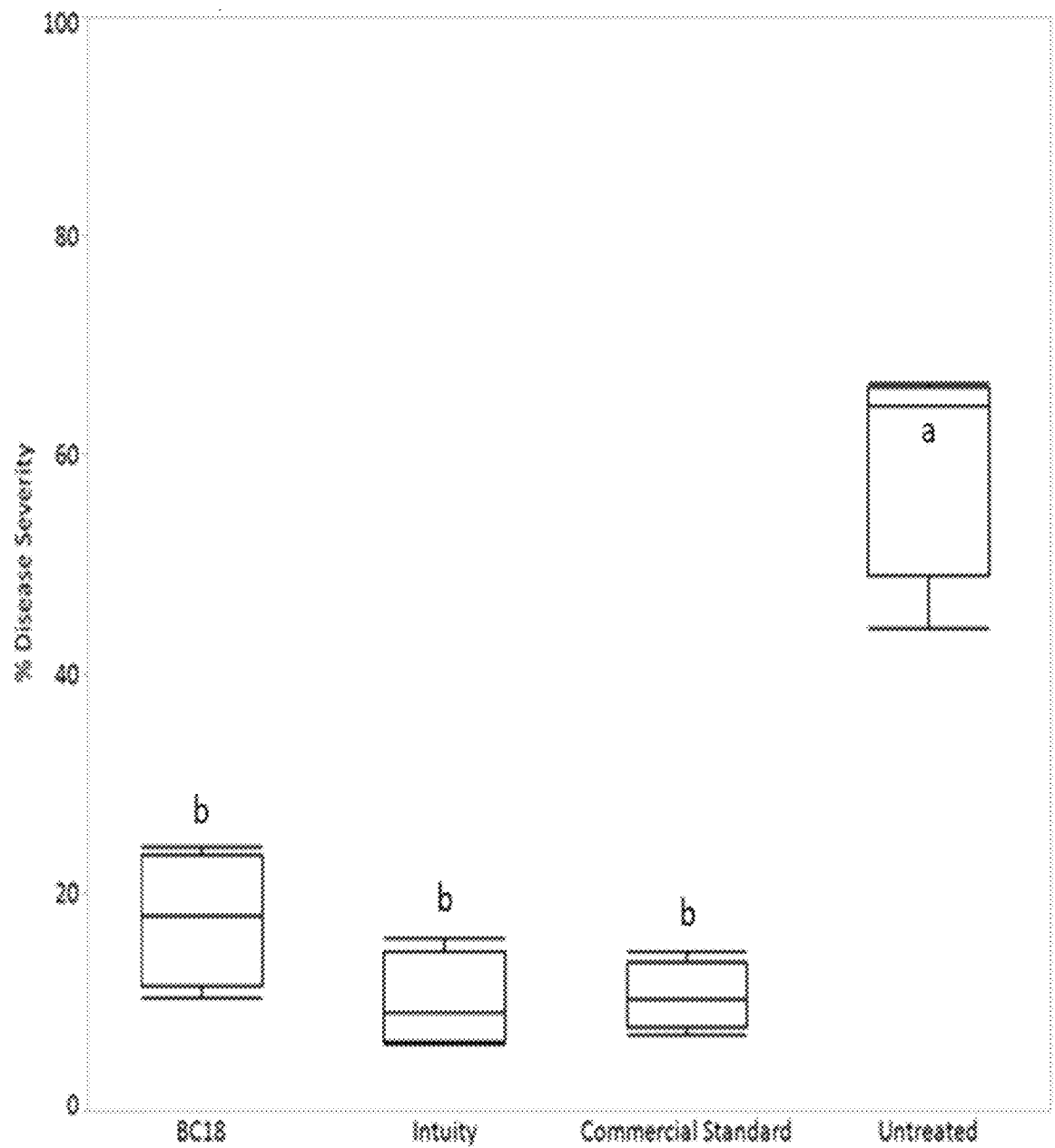
FIG. 24A illustrates the percent disease severity of downy mildew in treated and untreated grape leaves.
Figure 24B:
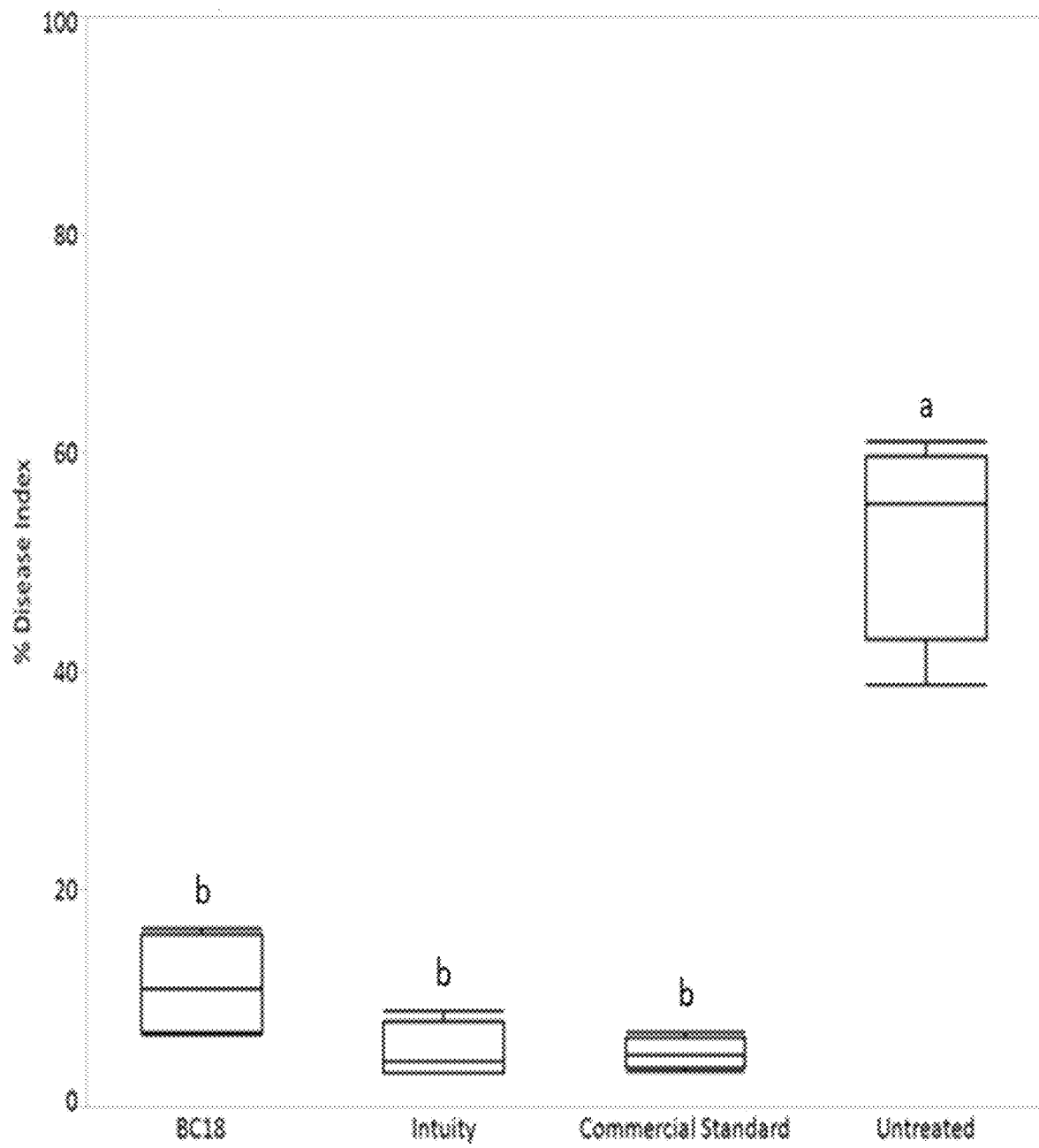
FIG. 24B illustrates the percent disease index of downy mildew in treated and untreated grape leaves.

BC18 was as effective as the commercial standard treatment in controlling Downy mildew in grape leaves (FIG. 24A and FIG. 24B respectively). BC18 treatment reduced Downy mildew in leaves induced by *Plasmopara viticola*, shown by a reduction in disease severity by about 71% (FIG. 24A) and disease index by about 80% (FIG. 24B), compared to leaves in untreated grape plants.

All data were analyzed through a one-way analysis of variance (ANOVA) and means were compared using Fisher's least significant difference (LSD). Box plots labeled with the same letter within each graph are not significantly different (LSD p=0.05).

Example 21

Evaluation of Efficacy of BC18 Against Rot Caused by *Botrytis cinerea* in Vignoles Grapes BC18 was assessed for its efficacy against rot caused by *Botrytis cinerea* in Vignoles grapes. Vines were treated with either BC18 or a control treatment. BC18 treatment consisted of eight application applied at 7-14 day intervals depending on growth stages. The first four applications were applied at the rate of 40 gallons/acre and the last four applications were at the rate of 50 gallons/acre. As control treatments, vines were either left untreated or treated with a combination of RevusTop (Syngenta) and Intuity (Valent USA) ("Intuity" in FIG. 25A and FIG. 25B), or a combination of Manzate (Keystone Pest Solutions) and Pristine (Bayer) ("Commercial Standard" in FIG. 25A and FIG. 25B). All treatment segments also received standard commercial fertility and insecticide. Vines were grown and maintained according to grower standard practice.

The treatment products were mixed in water according to manufactures' specifications and applied to the vines using a Spray bloom device. Four experimental replicates were conducted for each treatment. A randomized plot design was adopted for the study.

Figure 25A:
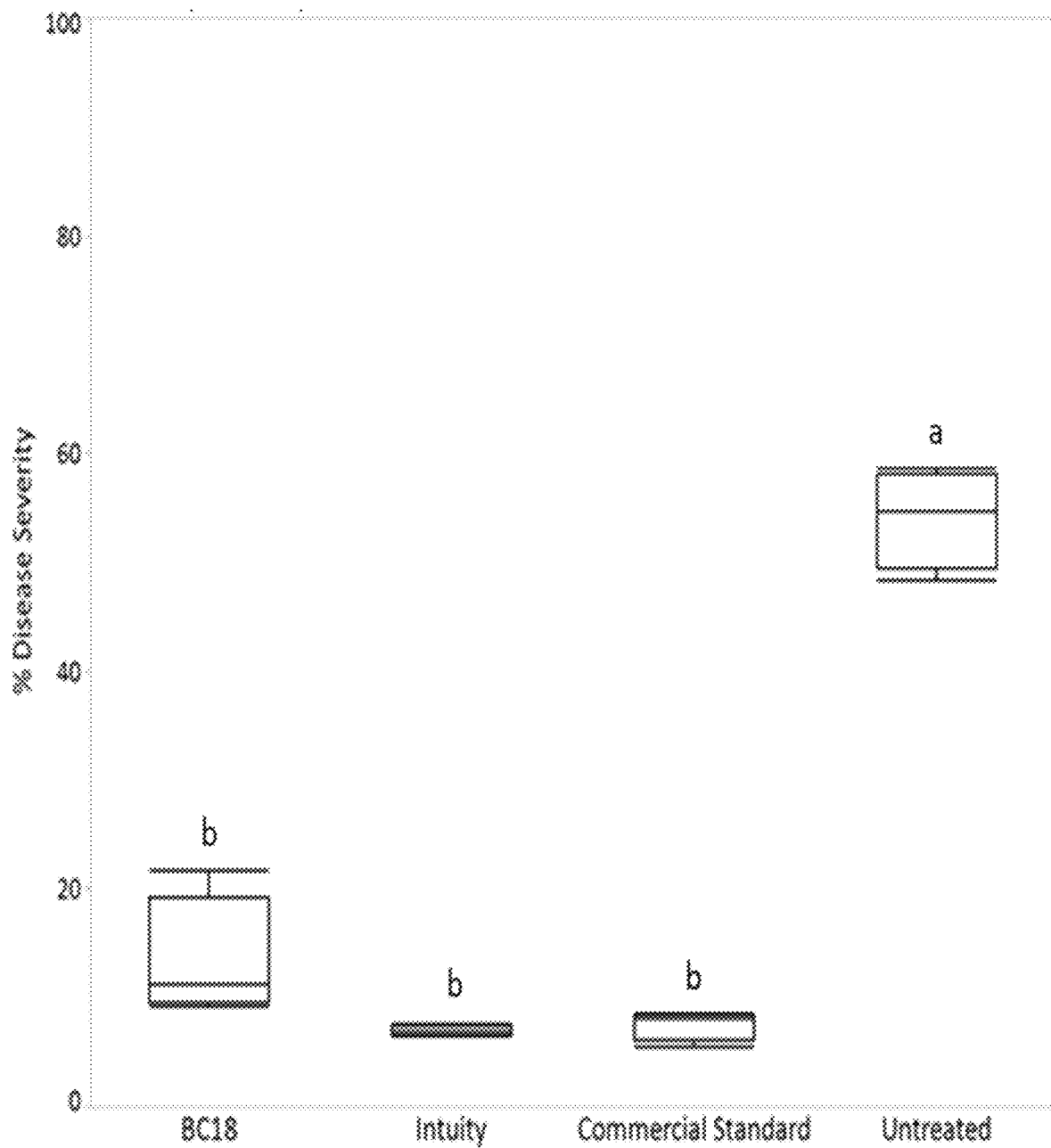
FIG. 25A illustrates the percent disease severity of *Botrytis* in treated and untreated grape bunches.
Figure 25B:
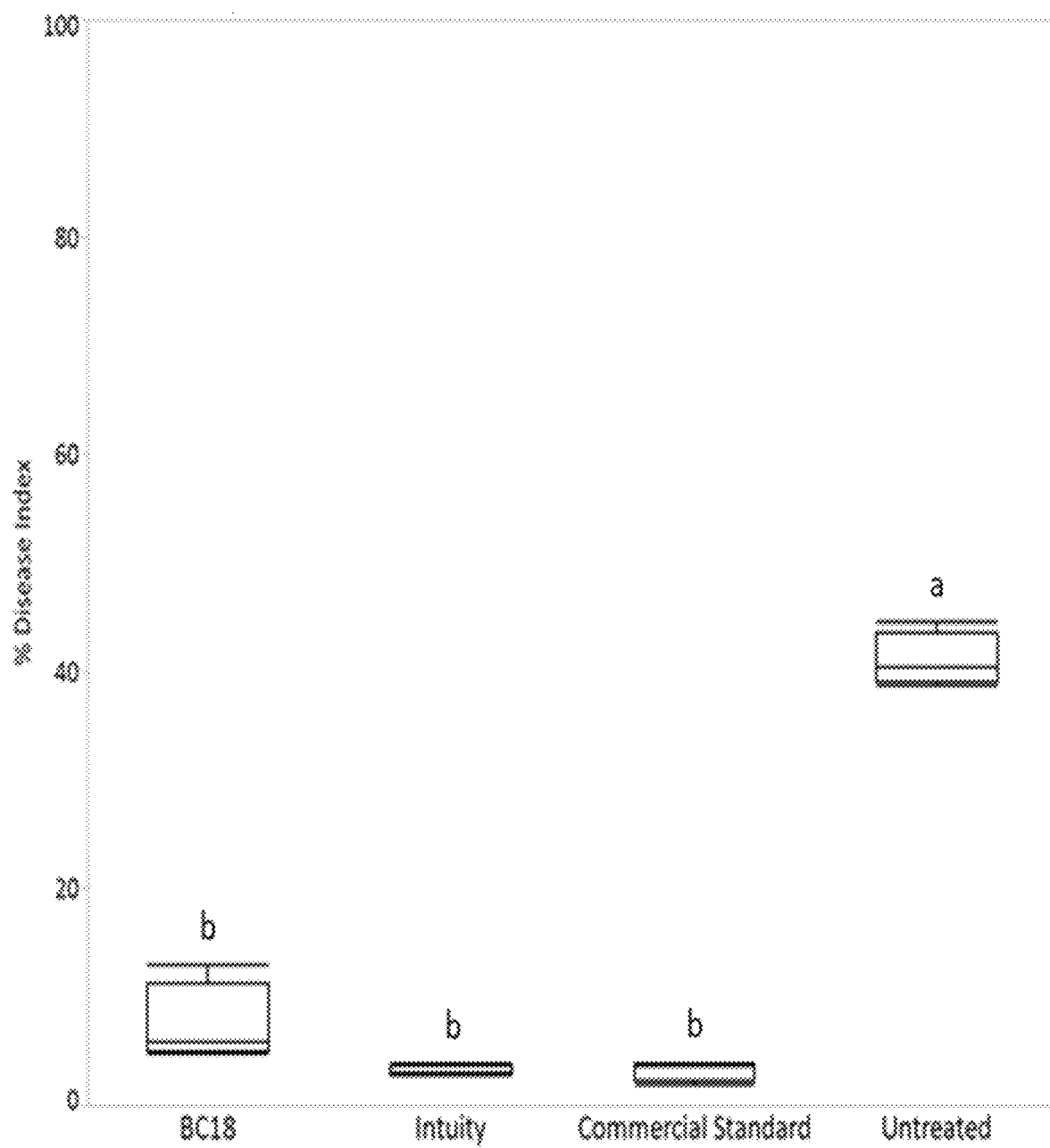
FIG. 25B illustrates the percent disease index of *Botrytis* in treated and untreated grape bunches.

BC18 was as effective as the commercial standard treatment in controlling *Botrytis cinerea* infection in grape bunches (FIG. 25A and FIG. 25B respectively). BC18 treatment inhibited rot induced by *Botrytis cinerea* in grape bunches, shown by a reduction in disease severity by nearly 80% (FIG. 25A) and a reduction in disease index by about 87% (FIG. 25B), compared to untreated grape bunches.

All data were analyzed through a one-way analysis of variance (ANOVA) and means were compared using Fisher's least significant difference (LSD). Box plots labeled with the same letter within each graph are not significantly different (LSD p=0.05).

Example 22

Evaluation of Efficacy of BC18 Against Powdery Mildew Induced by *Erysiphe necator* in Vignoles Grapes BC18 was assessed for its efficacy against powdery mildew caused by *Erysiphe necator* in Vignoles grapes. Vines were treated with either BC18 or a control treatment. BC18 treatment consisted of eight applications applied at 7-14 day intervals depending on growth stages. The first four applications were applied at the rate of 40 gallons/acre and the last four applications were applied at the rate of 50 gallons/acre. As control treatments, vines were either left untreated or treated with a combination of RevusTop (Syngenta) and Intuity (Valent USA) ("Intuity" in FIG. 26A and FIG. 26B), or a combination of Manzate (Keystone Pest Solutions) and Pristine (Bayer) ("Commercial Standard" in FIG. 26A and FIG. 26B). All treatment segments also received standard commercial fertility and insecticide program. Vines were grown and maintained according to grower standard practice.

The treatment products were mixed in water according to manufacturers' specification and applied to the vines using a Spray bloom device. Four experimental replicates were conducted for each treatment. A randomized plot design was adopted for the study.

Figure 26A:
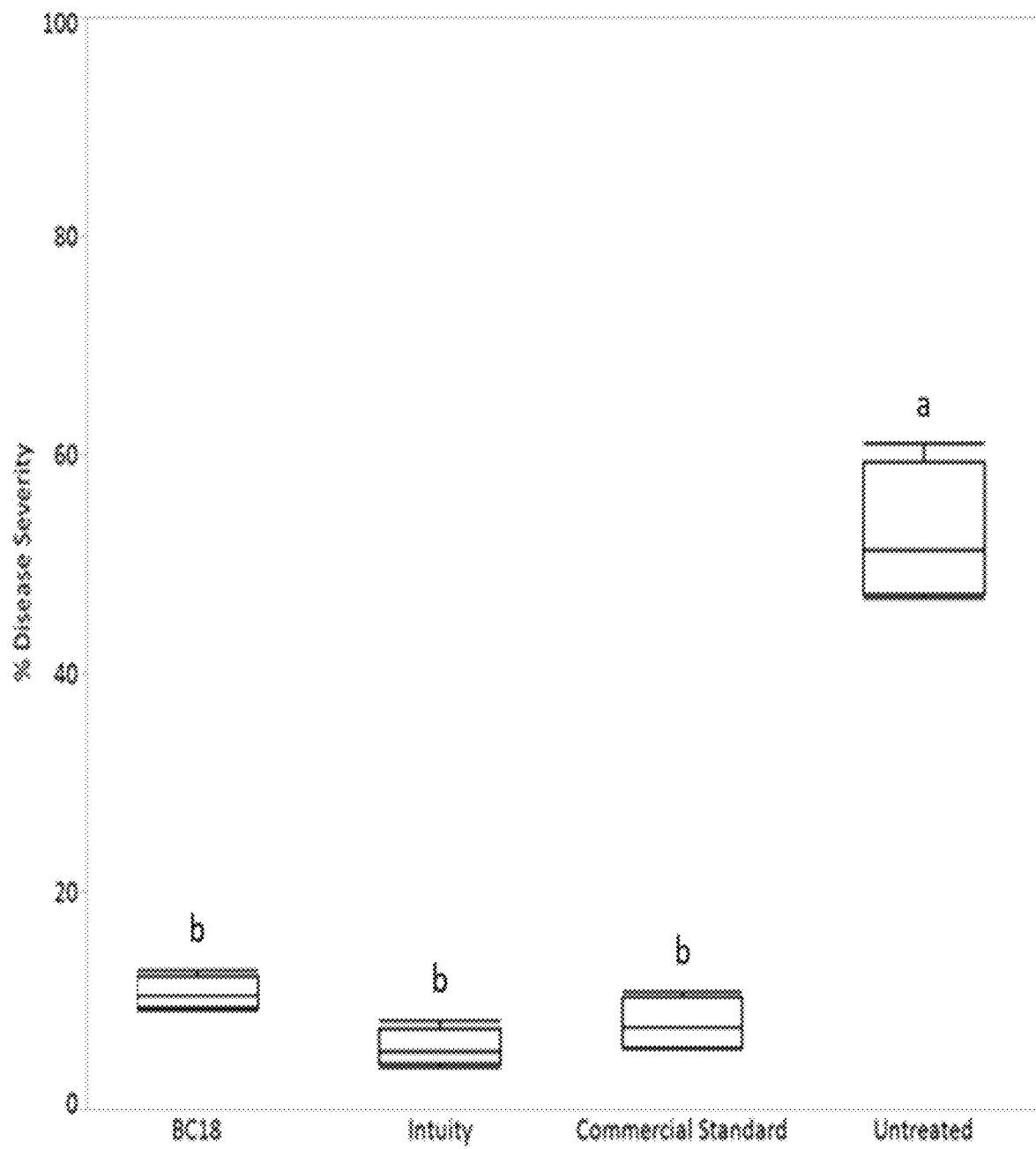
FIG. 26A illustrates the percent disease severity of powdery mildew in treated and untreated grape leaves.
Figure 26B:
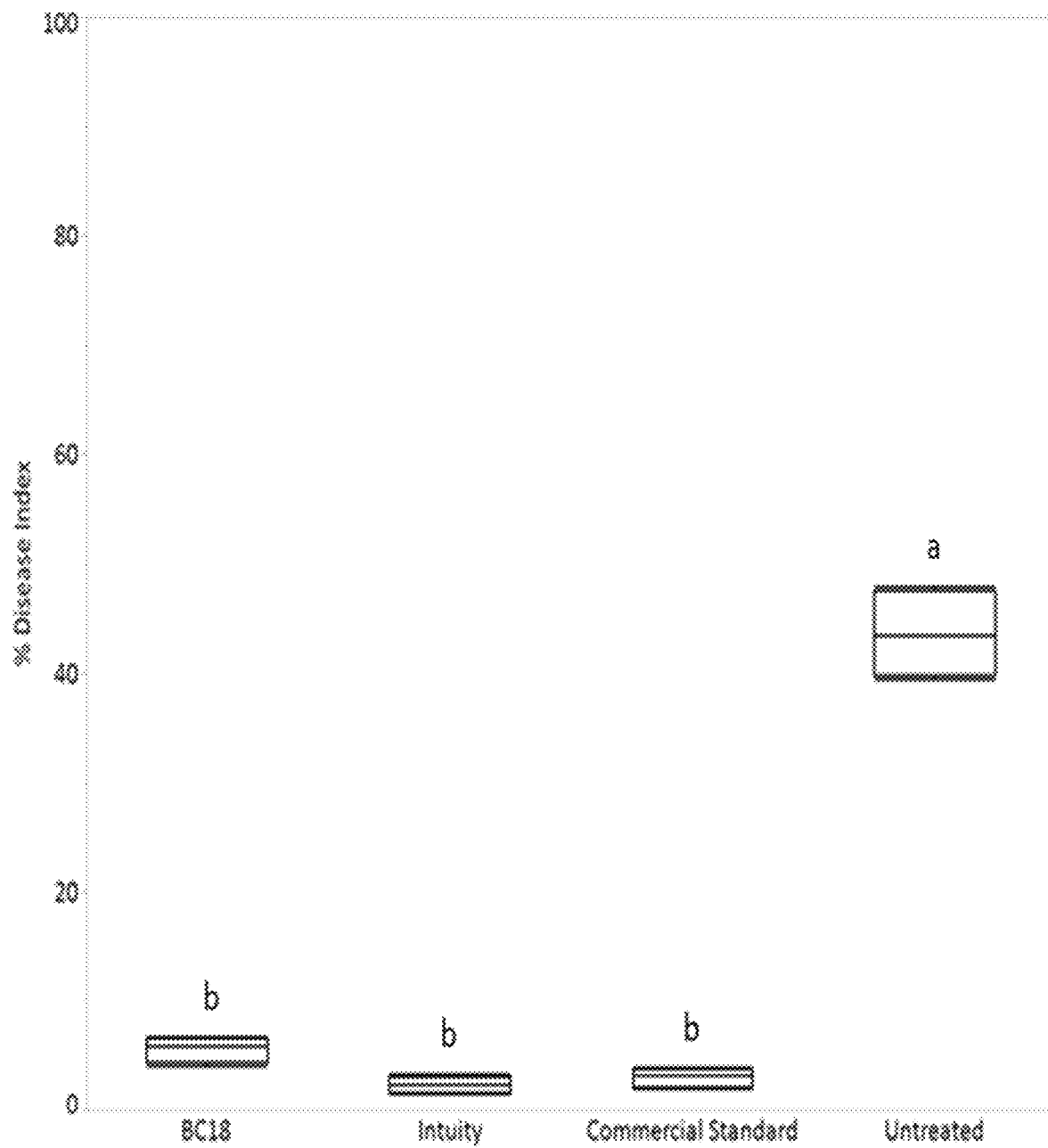
FIG. 26B illustrates the percent disease index of powdery mildew in treated and untreated grape leaves.

BC18 was as effective as Commercial Standard and Intuity treatment in controlling powdery mildew in grape leaves (FIG. 26A and FIG. 26B respectively). BC18 treatment reduced the severity of powdery mildew induced by *Erysiphe necator* in grape leaves by about 80% (FIG. 26A) and leading to a reduction in disease index by about 87% (FIG. 26B), compared to leaves in untreated grape bunches.

All data were analyzed through a one-way analysis of variance (ANOVA) and means were compared using Fisher's least significant difference (LSD). Box plots labeled with the same letter within each graph are not significantly different (LSD p=0.05).

Example 23

Evaluation of Efficacy of BC8 Against *Botrytis cinerea* Infection in Raspberry

BC8 was assessed for its efficacy against powdery mildew caused by *Botrytis cinerea* and *Podosphaera macularis* on Raspberry. The bushes were treated with either BC8 or a control treatment. BC8 treatments were applied at 14 day intervals or 7 day intervals depending upon growth stages. Treatment consisted of a total of 5-6 applications at a rate of 39 gallons/acre. As control treatments, bushes were either left untreated or treated with Industry Standard (a combination of Rally (Corteva Agriscience; active ingredient: mycobutanil), Pristine (BASF), Elevate (Arysta LifeScience; active ingredient: fenhexamid) and Switch (Syngenta)), or biological controls including Botector (Nufarm; active ingredient: *Aureobasidium pullalans*), Double Nickel (Certis; active ingredient: *Bacillus amyloliquefaciens* strain D747) or Stargus/NuFilm P. All treatment segments also received standard commercial fertility and insecticide program. The bushes were grown and maintained according to grower standard practice.

The treatment products were mixed in water according to manufacturer's specification and applied to plants at regular intervals. Four experimental replicates were conducted for each treatment. A randomized plot protocol was adopted for the study using 10' plots per treatment.

Figure 27A:
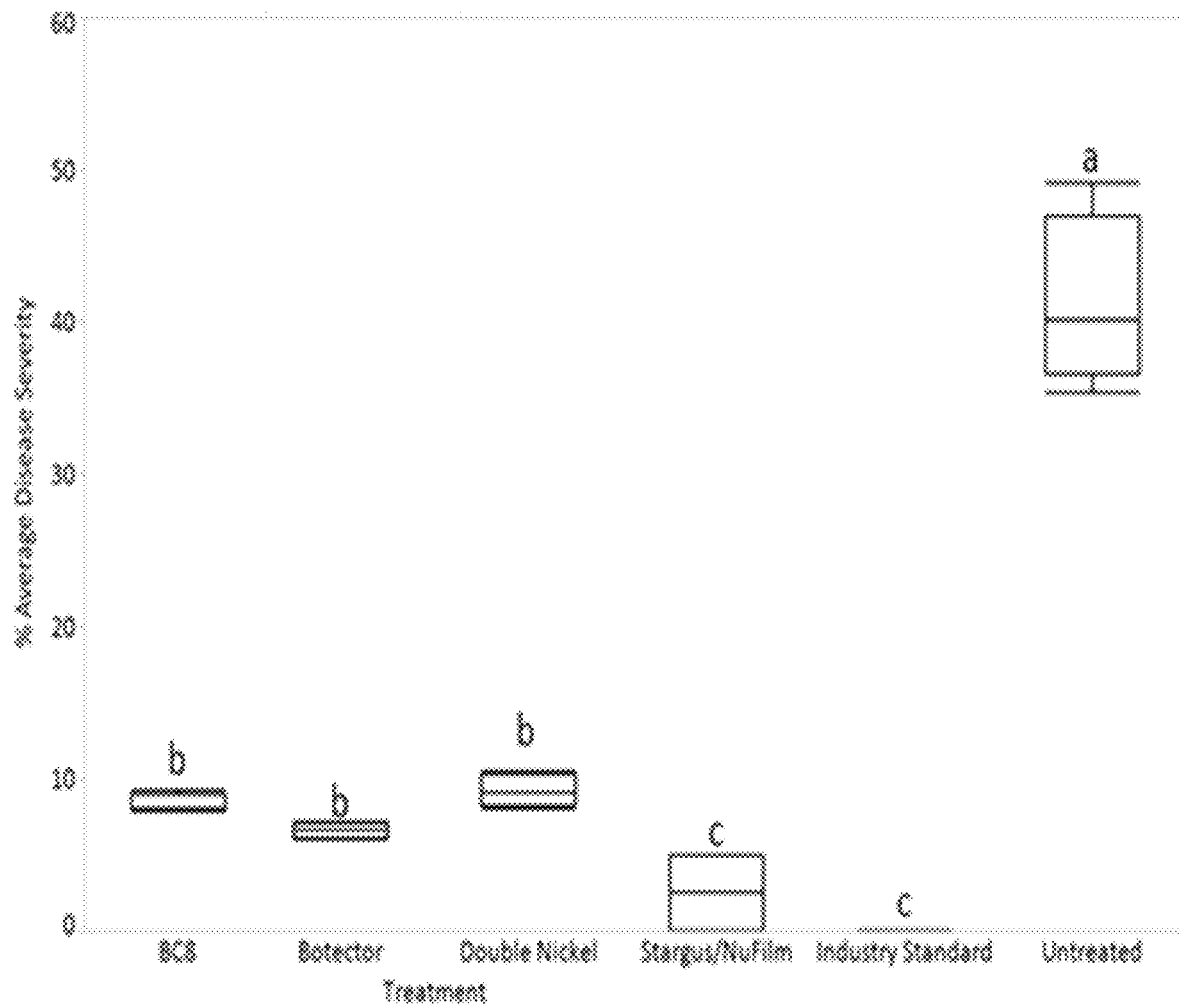
FIG. 27A illustrates the percent average disease severity of *Botrytis* in treated and untreated raspberry bushes.
Figure 27B:
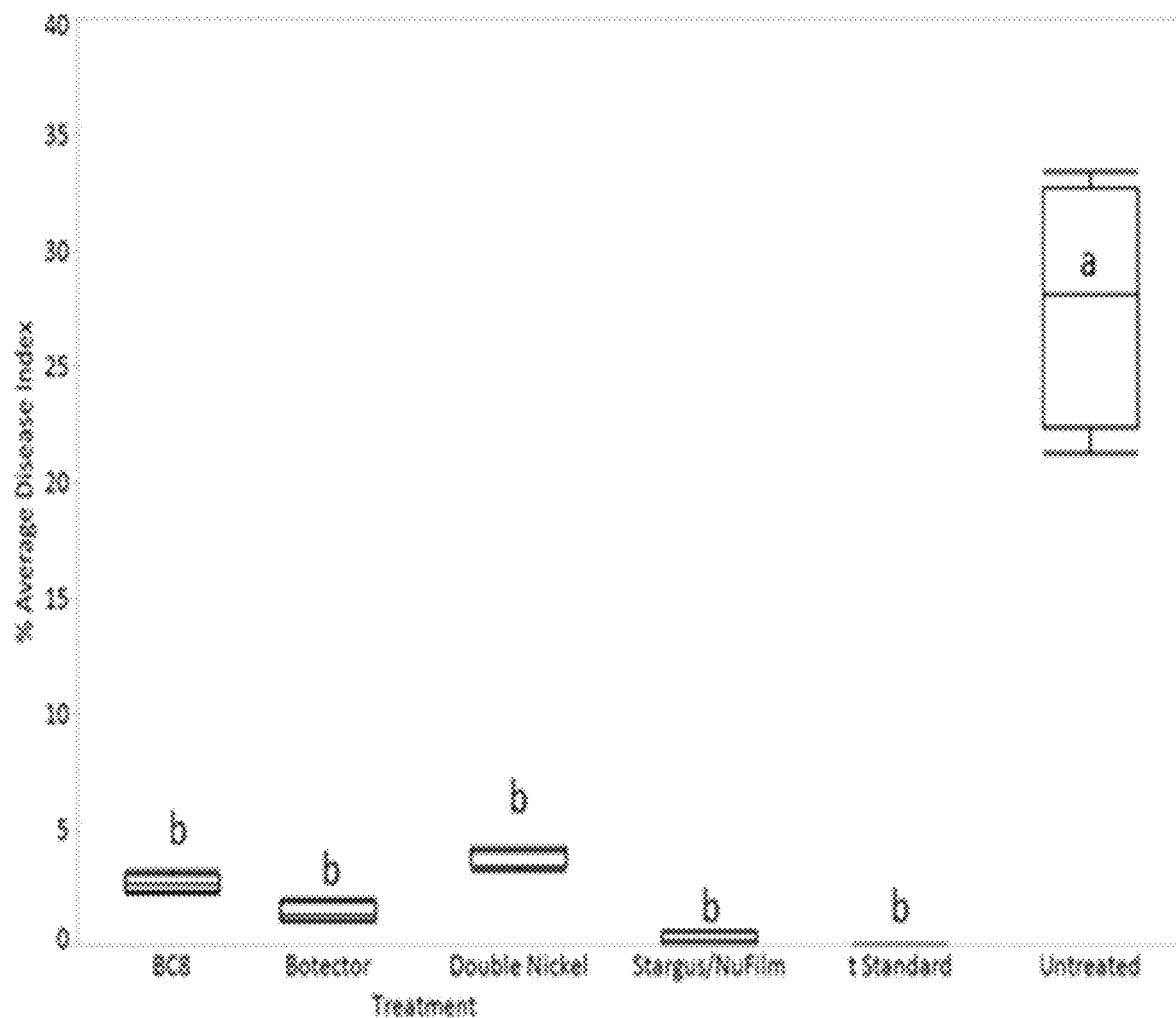
FIG. 27B illustrates the percent average disease index of *Botrytis* in treated and untreated raspberry bushes.

BC8 was as effective as the commercial treatments in controlling *Botrytis cinerea* infection in raspberry bushes. BC8 treatment reduced severity of *Botrytis cinerea* infection on raspberry plants by about 75% (FIG. 27A) and average disease index by more than 90% (FIG. 27B) compared to untreated controls.

All data were analyzed through a one-way analysis of variance (ANOVA) and means were compared using Fisher's least significant difference (LSD). Box plots labeled with the same letter within each graph are not significantly different (LSD p=0.05).

Example 24

Evaluation of Efficacy of BC8 Against Powdery Mildew Caused by *Podosphaera macularis* on Raspberry Bushes BC8 was assessed for its efficacy against powdery mildew caused by *Podosphaera macularis* on Raspberry bushes. The bushes were either treated with BC8 or a control treatment. BC8 treatments were applied at 14 day intervals or 7 day intervals depending upon growth stages. Treatment consisted of a total of 5-6 applications at a rate of 39 gallons/acre. As control treatments, bushes were either left untreated or treated with Industry Standard (a combination of Rally (Corteva Agriscience), Pristine (Bayer), Elevate (Arysta LifeScience) and Switch (Syngenta)), or biological controls including Botector, Double Nickel or Stargus/NuFilm P. All treatment segments also received standard commercial fertility and insecticide program. Bushes were grown and maintained according to grower standard practice.

The treatment products were mixed in water according to manufacturer's specification and applied to plants at regular intervals. Four experimental replicates were conducted for each treatment. A randomized plot protocol was adopted for the study using 10' plots per treatment.

Figure 28A:
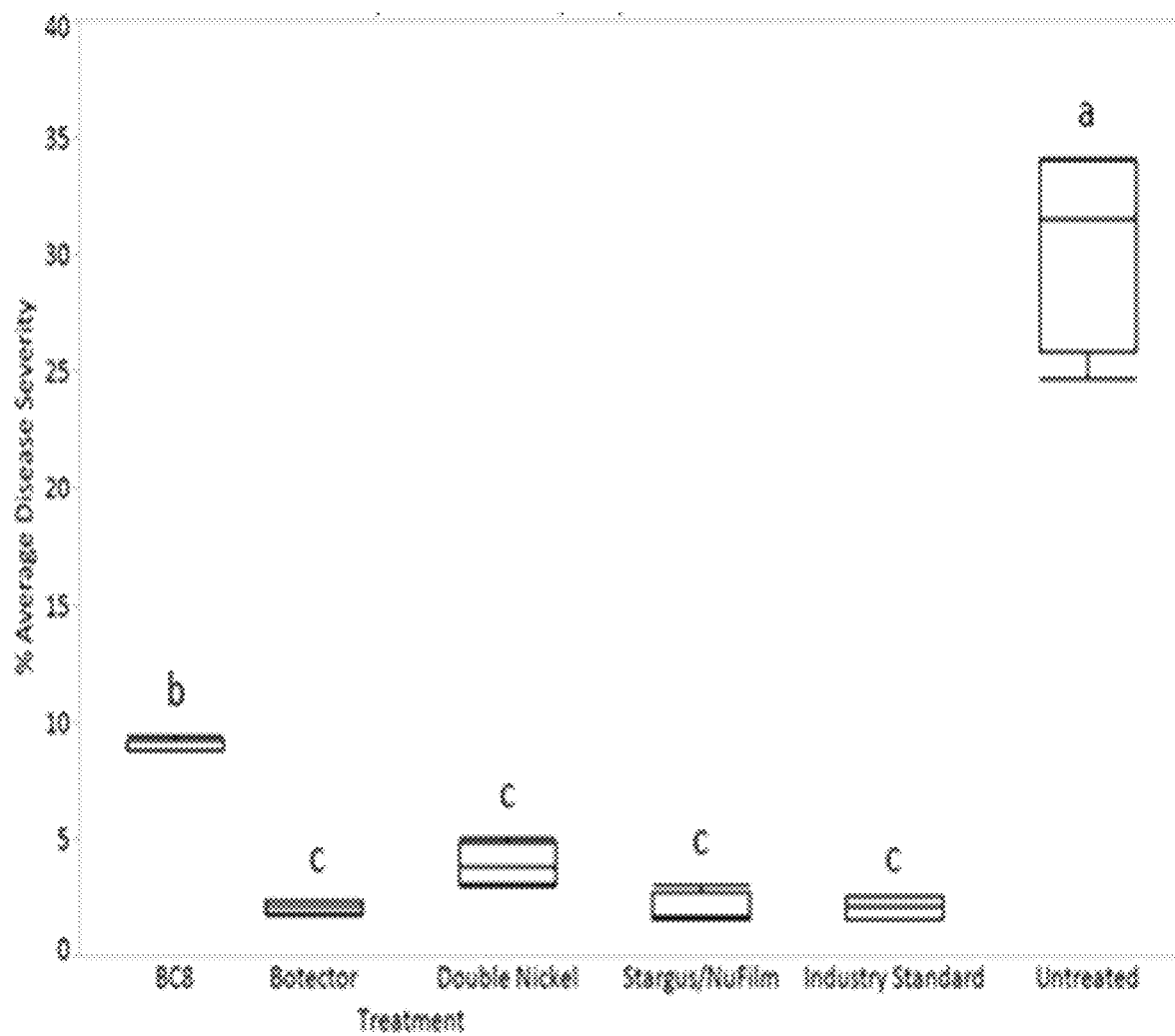
FIG. 28A illustrates the percent average disease severity of powdery mildew in treated and untreated raspberry leaves.
Figure 28B:
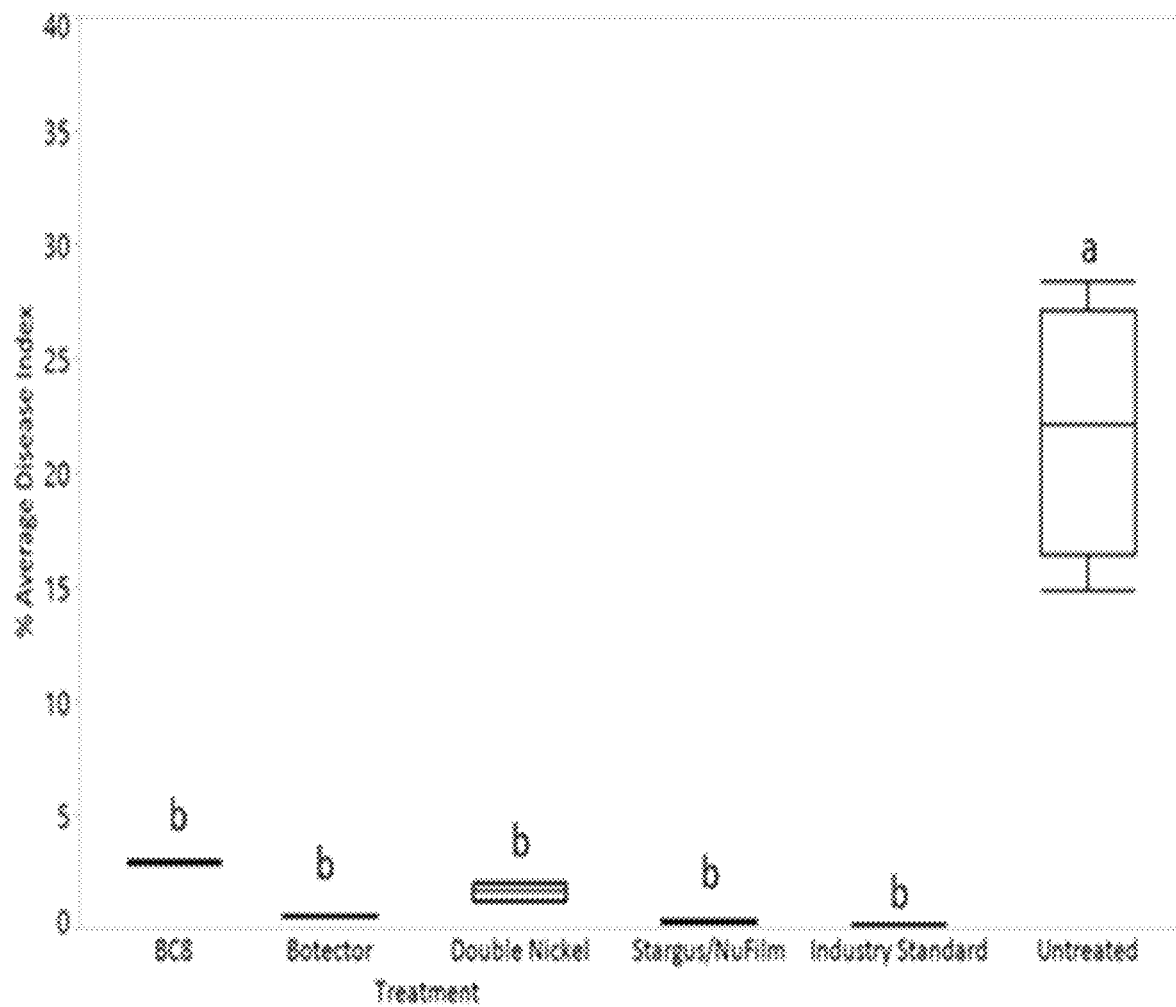
FIG. 28B illustrates the percent average disease index of powdery mildew in treated and untreated raspberry leaves.

Efficacy of BC8 against powdery mildew as measured by reduction in average disease severity and average disease index in raspberry leaves is shown in FIG. 28A and FIG. 28B, respectively. BC8 treatment reduced severity of *Podosphaera macularis* infection on raspberry leaves by about 75% (FIG. 28A). BC8 treatment was as effective as the commercial treatment and reduced average disease index by about 70% (FIG. 28B) compared to untreated controls.

Figure 29A:
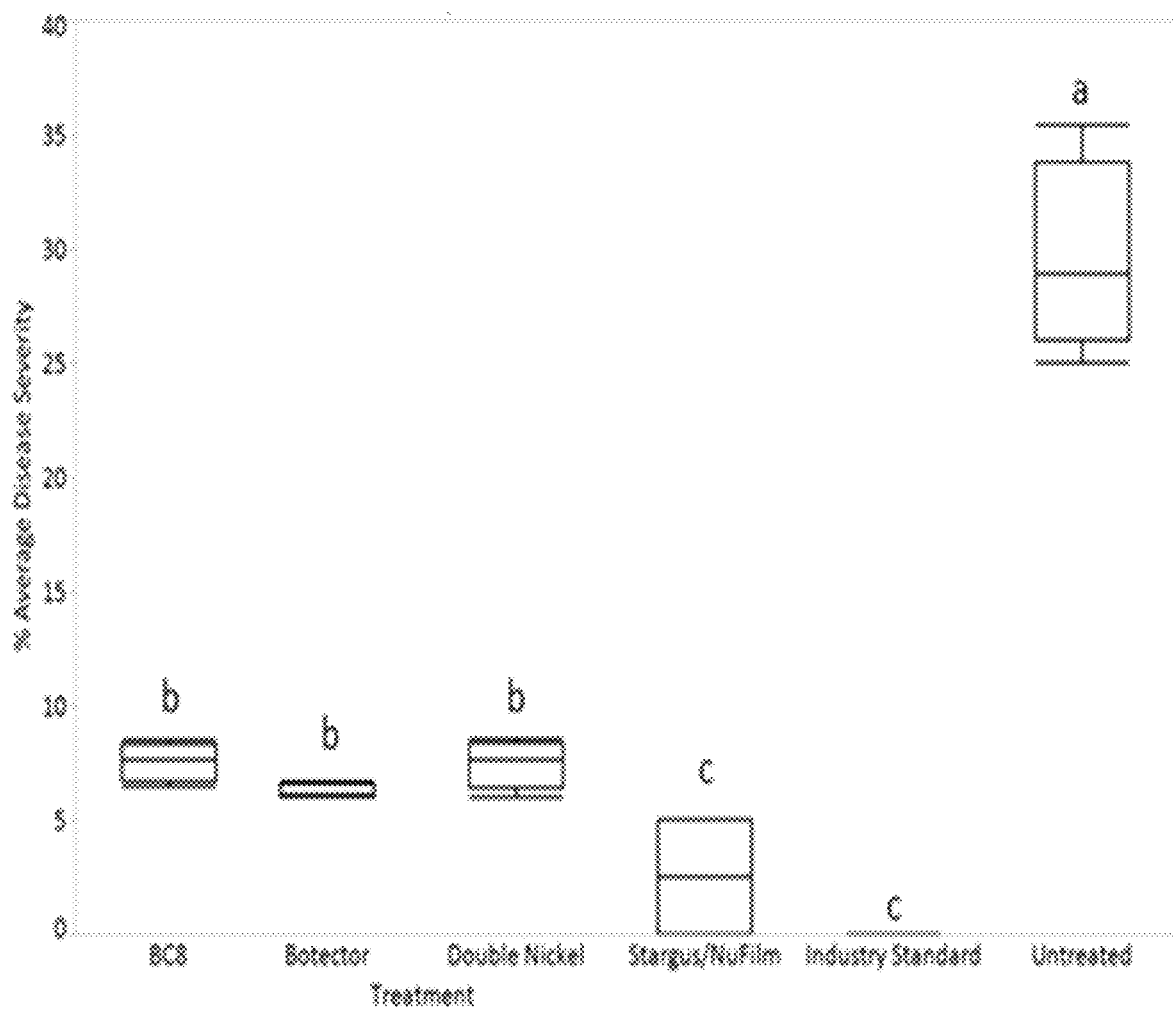
FIG. 29A illustrates the percent average disease severity of powdery mildew in treated and untreated raspberries.
Figure 29B:
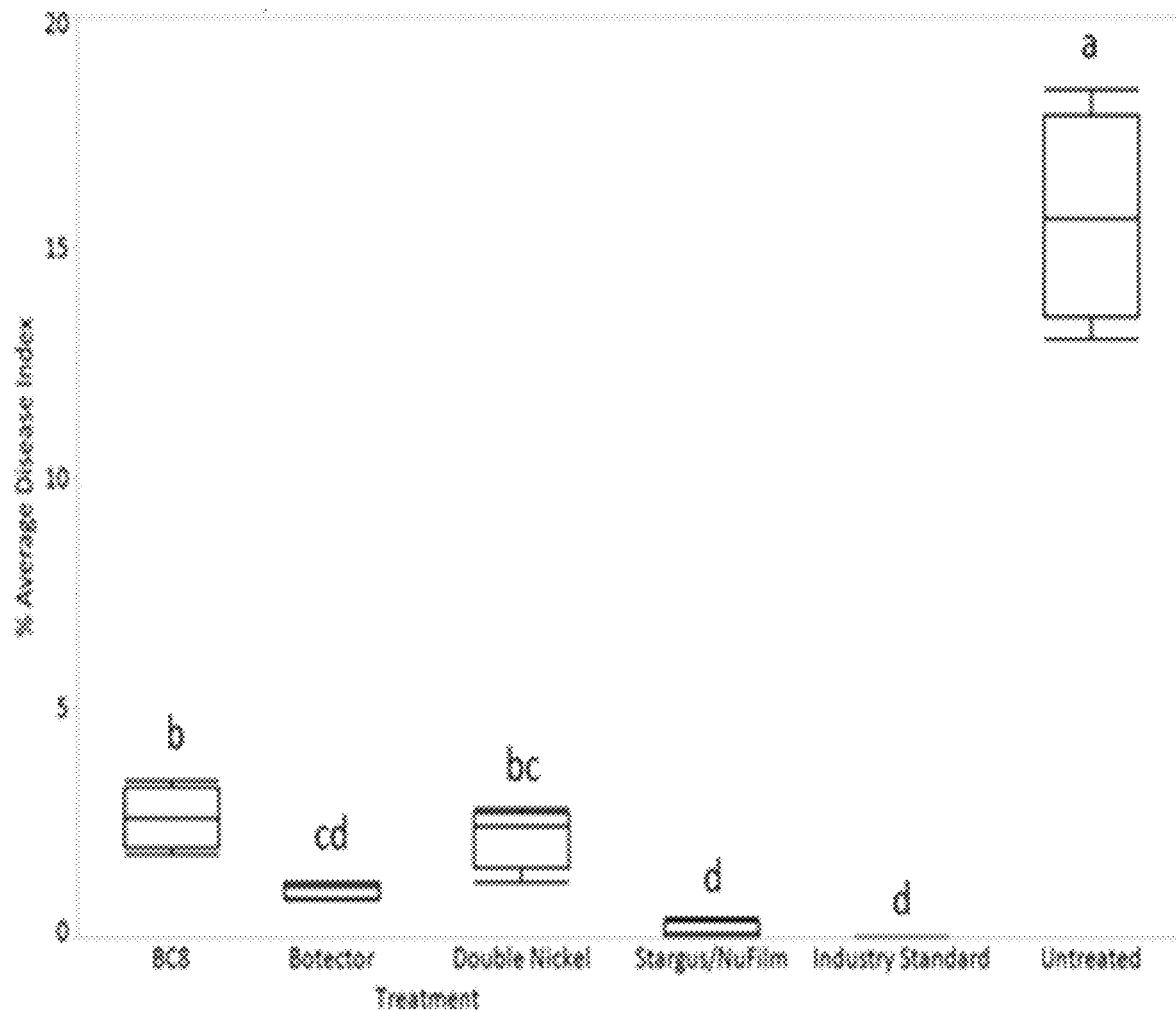
FIG. 29B illustrates the percent average disease index of powdery mildew in treated and untreated raspberries.

Efficacy of BC8 against powdery mildew as measured by reduction in average disease severity and disease index in raspberry berries is shown in FIG. 29A and FIG. 29B respectively. BC8 treatment reduced severity of *Podosphaera macularis* infection on raspberry berries by about 70% (FIG. 29A). BC8 treatment reduced average disease index in raspberry berries by about 90% (FIG. 29B) compared to untreated controls.

All data were analyzed through a one-way analysis of variance (ANOVA) and means were compared using Fisher's least significant difference (LSD). Box plots labeled with the same letter within each graph are not significantly different (LSD p=0.05).

Example 25

Evaluation of Efficacy of BC16 Against *Botrytis cinerea* Infection in Raspberry BC16 was assessed for its efficacy against powdery mildew caused by *Botrytis cinerea* and *Podosphaera macularis* on Raspberry. The bushes were treated with either BC16 or a control treatment. BC16 treatments were applied at 14 day intervals or 7 day intervals depending upon growth stages. Treatment consisted of a total of 5-6 applications at a rate of 39 gallons/acre. As control treatments, bushes were either left untreated or treated with Industry Standard (a combination of Rally (Corteva Agriscience), Pristine (Bayer), Elevate (Arysta LifeScience) and Switch (Syngenta)), or biological controls including Botector, Double Nickel or Stargus/NuFilm P. All treatment segments also received standard commercial fertility and insecticide program. The bushes were grown and maintained according to grower standard practice.

The treatment products were mixed in water according to manufacturer's specification and applied to plants at regular intervals. Four experimental replicates were conducted for each treatment. A randomized plot protocol was adopted for the study using 10' plots for treatment.

Figure 30A:
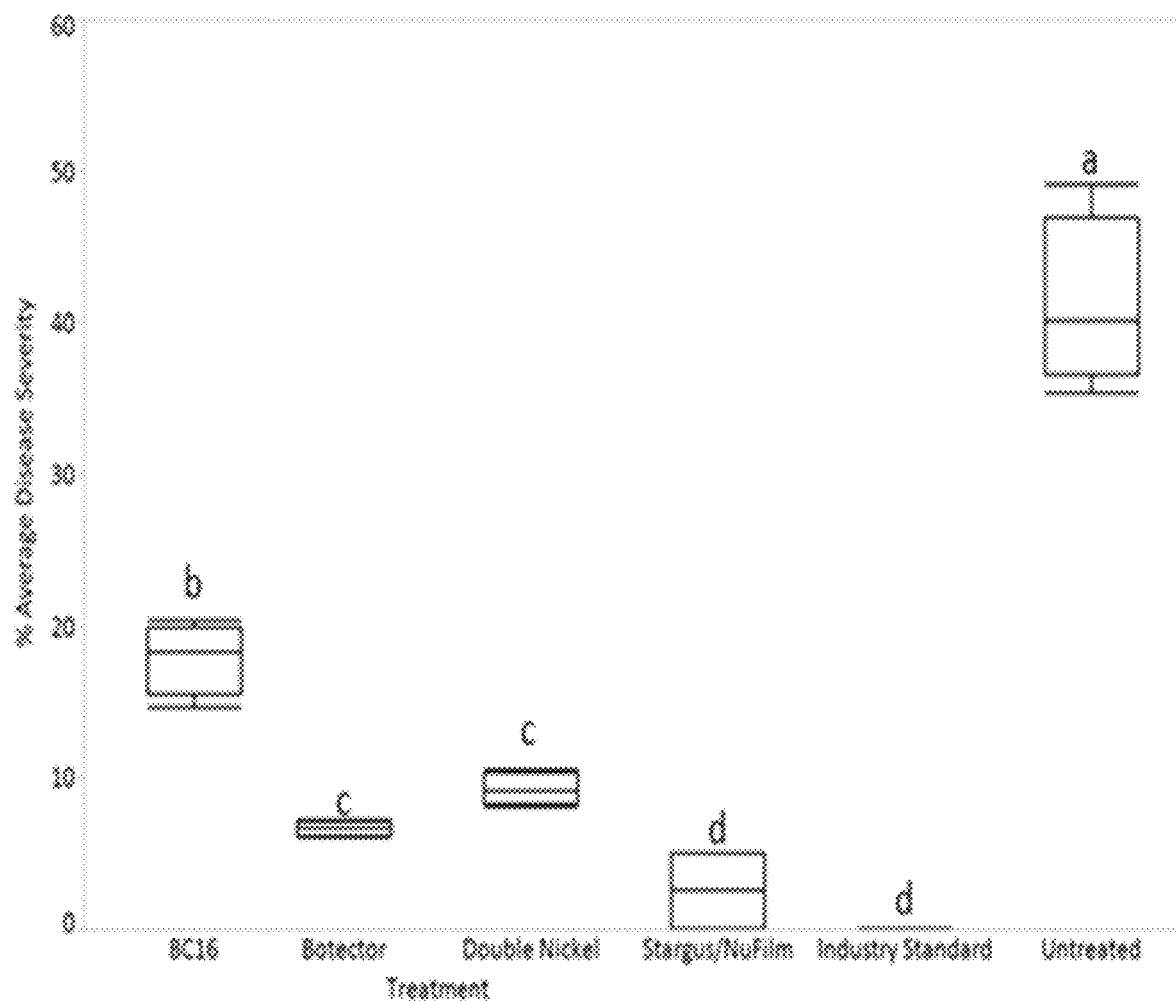
FIG. 30A illustrates the percent average disease severity of *Botrytis* in treated and untreated raspberry bushes.
Figure 30B:
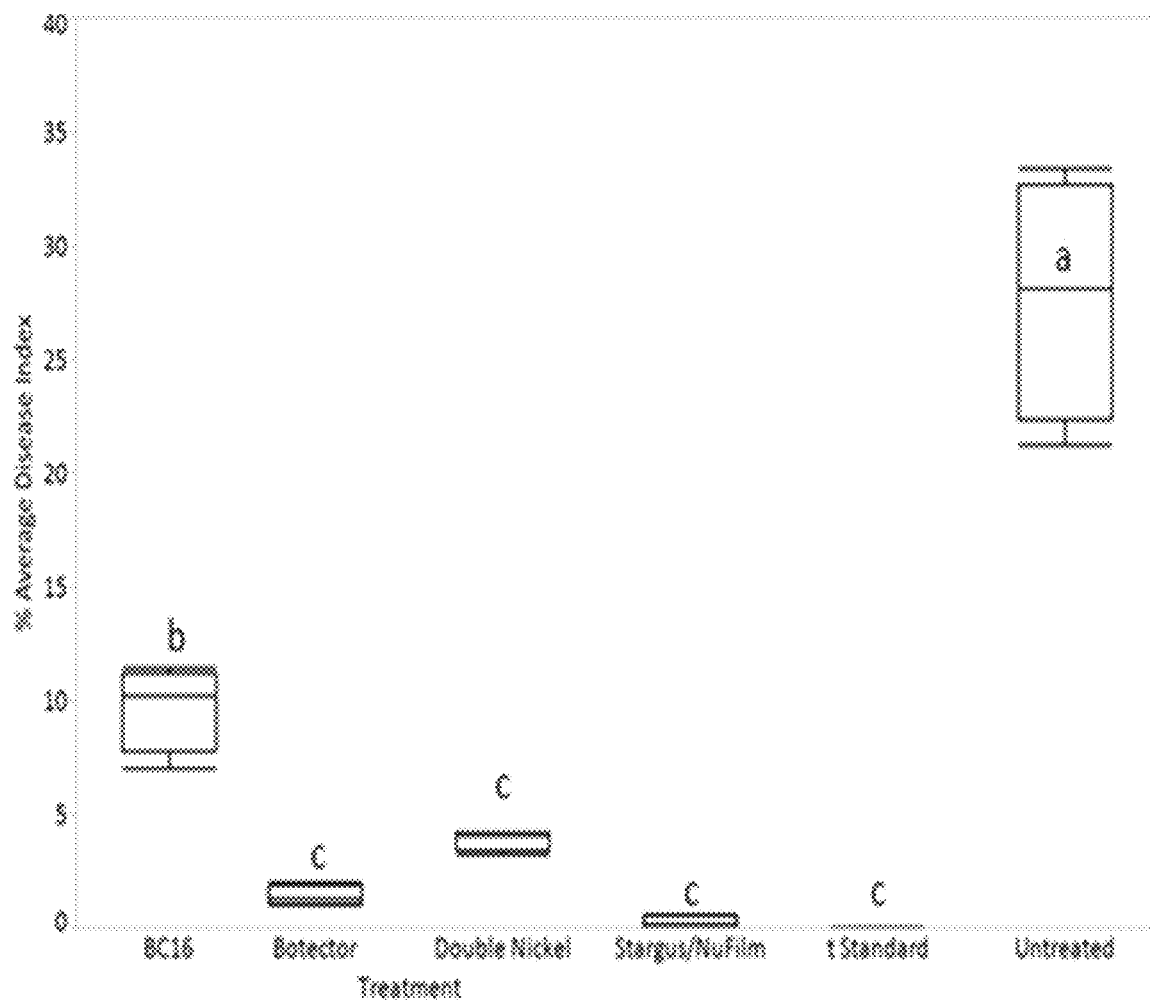
FIG. 30B illustrates the percent average disease index of *Botrytis* in treated and untreated raspberry bushes.

BC16 was as effective in controlling *Botrytis cinerea* infection in raspberry bushes. BC16 treatment reduced severity of *Botrytis cinerea* infection on raspberry plants by about 50% (FIG. 30A) and average disease index by more than 63% (FIG. 30B) compared to untreated controls.

All data were analyzed through a one-way analysis of variance (ANOVA) and means were compared using Fisher's least significant difference (LSD). Box plots labeled with the same letter within each graph are not significantly different (LSD p=0.05).

Example 26

Evaluation of Efficacy of BC16 Against Powdery Mildew Caused by *Podosphaera macularis* on Raspberry Bushes BC16 was assessed for its efficacy against powdery mildew caused by *Podosphaera macularis* on Raspberry bushes. The bushes were treated with either BC16 or a control treatment. BC16 treatments were applied at 14 day intervals or 7 day intervals depending upon growth stages. Treatment consisted of a total of 5-6 applications at a rate of 39 gallons/acre. As control treatments, bushes were either left untreated or treated with Industry Standard (a combination of Rally (Corteva Agriscience), Pristine (Bayer), Elevate (Arysta LifeScience) and Switch (Syngenta)), or biological controls including Botector, Double Nickel or Stargus/NuFilm P. All treatment segments also received standard commercial fertility and insecticide program consisting. Bushes were grown and maintained according to grower standard practice.

The treatment products were mixed in water according to manufacturer's specification and applied to plants at regular intervals. Four experimental replicates were conducted for each treatment. A randomized plot protocol was adopted for the study using 10' plots per treatment.

Figure 31A:
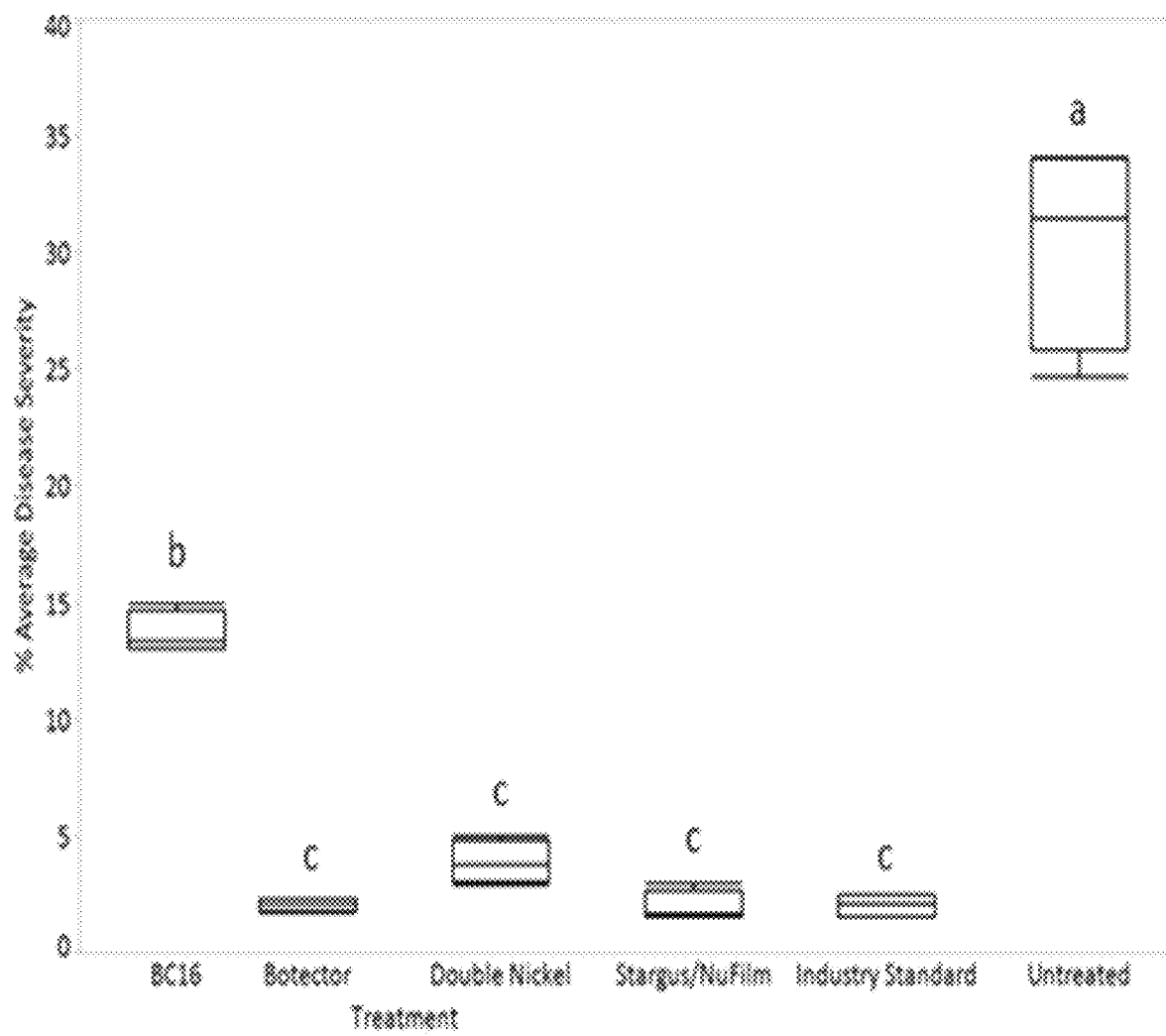
FIG. 31A illustrates the percent disease severity of powdery mildew in treated and untreated raspberry leaves. FIG.
Figure 31B:
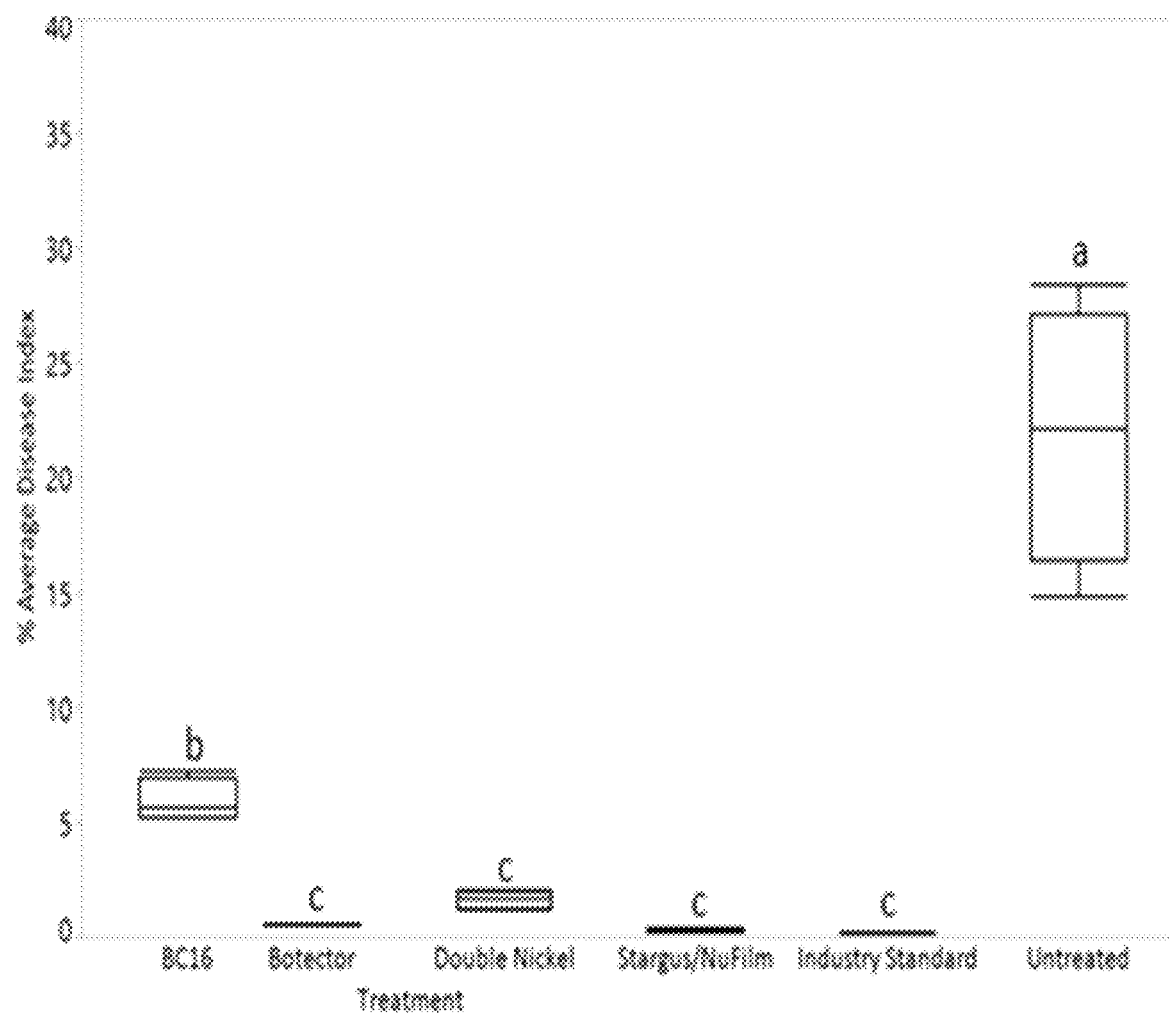

Efficacy of BC16 against powdery mildew as measured by reduction in disease severity and disease index in raspberry leaves is shown in FIG. 31A and FIG. 31B respectively. BC16 treatment reduced severity of *Podosphaera macularis* infection on raspberry leaves by about 56% (FIG. 31A). BC16 treatment reduced average disease index by about 70% (FIG. 31B) compared to untreated controls.

Efficacy of BC16 against powdery mildew as measured by reduction in disease severity and disease index in raspberry berries is shown in FIG. 32A and FIG. 32B respectively. BC16 treatment reduced severity of *Podosphaera macularis* infection on raspberry berries by about 50% (FIG. 32A). BC16 treatment reduced average disease index in raspberry berries by about 55% (FIG. 32B) compared to untreated controls.

All data were analyzed through a one-way analysis of variance (ANOVA) and means were compared using Fisher's least significant difference (LSD). Box plots labeled with the same letter within each graph are not significantly different (LSD p=0.05).

Example 27

Evaluation of Efficacy of BC17 Against *Botrytis cinerea* Infection in Raspberry BC17 was assessed for its efficacy against powdery mildew caused by *Botrytis cinerea* and *Podosphaera macularis* on Raspberry. The bushes were treated with either BC17 or a control treatment. BC17 treatments were applied at 14 day intervals or 7 day intervals depending upon growth stages. Treatment consisted of a total of 5-6 applications at a rate of 39 gallons/acre. As control treatments, bushes were either left untreated or treated with Industry Standard (a combination of Rally (Corteva Agriscience), Pristine (Bayer), Elevate (Arysta LifeScience) and Switch (Syngenta)), or biological controls including Botector, Double Nickel or Stargus/NuFilm P. All treatment segments also received standard commercial fertility and insecticide program. The bushes were grown and maintained according to grower standard practice.

The treatment products were mixed in water according to manufacturer's specifications and applied to plants at regular intervals. Four experimental replicates were conducted for each treatment. A randomized plot protocol was adopted for the study.

BC17 was effective in controlling *Botrytis cinerea* infection in raspberry bushes. BC17 treatment reduced severity of *Botrytis cinerea* infection on raspberry plants by about 50% (FIG. 33A) and average disease index by more than 55% (FIG. 33B) compared to untreated controls.

All data were analyzed through a one-way analysis of variance (ANOVA) and means were compared using Fisher's least significant difference (LSD). Box plots labeled with the same letter within each graph are not significantly different (LSD p=0.05).

Example 28

Evaluation of Efficacy of BC17 Against Powdery Mildew Caused by *Podosphaera macularis* on Raspberry Bushes BC17 was assessed for its efficacy against powdery mildew caused by *Podosphaera macularis* on Raspberry bushes. Bushes were treated with either BC17 or a control treatment. BC17 treatments were applied at 14 day intervals or 7 day intervals depending upon growth stages. Treatment consisted of a total of 5-6 applications at a rate of 39 gallons/acre. As control treatments, bushes were either left untreated or treated with Industry Standard (a combination of Rally (Corteva Agriscience), Pristine (Bayer), Elevate (Arysta LifeScience) and Switch (Syngenta)), or biological controls including Botector, Double Nickel or Stargus/NuFilm P. All treatment segments also received standard commercial fertility and insecticide program. Bushes were grown and maintained according to grower standard practice.

The treatment products were mixed in water according to manufacturer's specification and applied to plants at regular intervals. Four experimental replicates were conducted for each treatment. A randomized plot protocol was adopted for the study.

Efficacy of BC17 against powdery mildew as measured by reduction in disease severity and disease index in raspberry leaves is shown in FIG. 34A and FIG. 34B respectively. BC17 treatment reduced severity of *Podosphaera macularis* infection on raspberry leaves by about 45% (FIG. 34A). BC17 treatment reduced average disease index by about 70% (FIG. 34B) compared to untreated controls.

Efficacy of BC17 against powdery mildew as measured by reduction in disease severity and disease index in raspberry berries is shown in FIG. 35A and FIG. 35B respectively. BC17 treatment reduced severity of *Podosphaera macularis* infection on raspberry berries by about 50% (FIG. 35A). BC17 treatment reduced average disease index in raspberry berries by about 50% (FIG. 35B) compared to untreated controls.

All data were analyzed through a one-way analysis of variance (ANOVA) and means were compared using Fisher's least significant difference (LSD). Box plots labeled with the same letter within each graph are not significantly different (LSD p=0.05).

Example 29

Evaluation of Efficacy of BC16 Against Rot Caused by *Botrytis cinerea* and *Rhizopus* Spp. Infection on Strawberry Fruit BC16 was assessed for its efficacy against rot caused by *Botrytis cinerea* and *Rhizopus* spp. on strawberry fruit Plots of strawberry forbs were treated with either BC16 or a control treatment. BC16 treatment consisted of five foliar applications applied weekly at the rate of 40 quarts/acre. As control treatments, plots were either left untreated or treated with the commercial standard including CAPTAN (Keystone Pest solutions) and Procidic (Greenspire Global Inc.; active ingredient: citric acid), Aviv (Sym Agro; active ingredient: *Bacillus subtilis* strain IAB/BS03), Stk 73 (STK), Procidic (Greenspire Global Inc.). All treatment segments also received standard commercial fertility and insecticide program. The forbs were grown and maintained according to grower standard practice.

The treatment products were mixed in a water volume of 150 gallons per acre and applied to the forbs using a handheld $CO_2$ backpack spray with 8 nozzles. Four experimental replicates were conducted for each treatment. A randomized plot design was adopted for the study. The first harvest was taken the day after last application and the second harvest taken 7 days after the last application. Data was collected from 32 ripe berries collected from each plot and observed for 12-14 days to assess berry decay due to the presence of *Botrytis cinerea* or *Rhizopus* spp.

The results expressed as number of decayed fruit are shown in FIG. 36. BC16 treated berries had significantly less decay compared to the untreated berries, and performed comparably to the commercially available fungicides that were used in this trial.

All data were analyzed through a one-way analysis of variance (ANOVA) and means were compared using Fisher's least significant difference (LSD). Box plots labeled with the same letter within each graph are not significantly different (LSD p=0.05).

Example 30

Evaluation of Efficacy of BC17 Against Rot Caused by *Botrytis cinerea* and *Rhizopus* Spp. Infection on Strawberry Fruit BC17 was assessed for its efficacy against rot caused by *Botrytis cinerea* and *Rhizopus* spp. on strawberry fruit Plots of strawberry forbs were treated with either BC17 or a control treatment. BC17 treatment consisted of five foliar applications applied weekly at the rate of 40 quarts/acre. As control treatments, bushes were either left untreated or treated with the commercial standards including CAPTAN (Keystone Pest solutions) and Procidic (Greenspire Global Inc.), Aviv (Sym Agro), Stk 73 (STK), Procidic (Greenspire Global Inc.). All treatment segments also received standard commercial fertility and insecticide program. The bushes were grown and maintained according to grower standard practice. The treatment products were mixed in a water volume of 150 gallons per acre and applied to the bushes using a handheld $CO_2$ backpack spray with 8 nozzles. Four experimental replicates were conducted for each treatment. A randomized plot design was adopted for the study. The first harvest was taken the day after last application and the second harvest taken 7 days after the last application. Data was collected from 32 ripe berries collected from each plot and observed for 12-14 days to assess berry decay due to the presence of *Botrytis cinerea* or *Rhizopus* spp.

The results expressed as number of decayed fruit are shown in FIG. 37. BC17 treated berries had significantly less decay compared to the untreated berries, and performed comparably to the commercially available fungicides that were used in this trial.

All data were analyzed through a one-way analysis of variance (ANOVA) and means were compared using Fisher's least significant difference (LSD). Box plots labeled with the same letter within each graph are not significantly different (LSD p=0.05).

Example 31

Evaluation of Efficacy of BC17 Against Root Rot Caused by *Pythium* sp. on Soybean BC17 was assessed for its efficacy against root rot caused by *Pythium* sp. on soybean. Plots were treated with either BC17 or a control treatment. BC17 treatments consisted of three applications on Credenz variety of soybean. The first application was at planting either in furrow or drench on top of seed line after planting. The second application drench was at 100% emergence and the third application was conducted 7-10 days after the second application. Treatment consisted of two different application rates of 20 quarts/acre or 40 quarts/acre. As control treatments, plots were either left untreated or treated with the commercial standard, Daconil SDG (Syngenta) ("Commercial Standard" in FIG. 38. All treatment segments also received standard commercial fertility and insecticide program consisting. The plots were grown and maintained according to grower standard practice.

The treatment products were mixed in a water volume of 20 gallons per acre and applied using a knapsack sprayer (0.5 foot boom with flood nozzles at 28 psi) to plants at the conventional seasonal times (late June) or first sign of disease (whichever comes earlier). Four experimental replicates were conducted for each treatment. Two rows each of 20 feet length were treated with BC17 with 1 row preserved as buffer between treatment plots. Four replicates were conducted in each treatment protocol. A randomized complete block design was adopted for this study.

Crop stand evaluation was performed as a measure of plant health and the emergence rate. The results expressed as Crop stand (per meter) are shown in FIG. 38. Crop stand count was assessed at second application, prior to third application and 14 days after third application. BC17 treatment at 40 qts/acre significantly increase soybean crop stand when compared to the untreated soybean. BC17 performed better than the commercial standard in increasing crop stand.

All data were analyzed through a one-way analysis of variance (ANOVA) and means were compared using Fisher's least significant difference (LSD). Box plots labeled with the same letter within each graph are not significantly different (LSD p=0.05).

Example 32

Efficacy of Biocontrol Composition Against Infection by *Botrytis cinerea* on Raspberry Shelf Life Raspberries were harvested from a plant and placed in a sterile container. The raspberries did not have any noticeable fungal infection. The raspberries were deliberately infected with *Botrytis cinerea*. Two groups of raspberries were evaluated; one which has been treated with a supernatant of a BC8 culture, and the other was left untreated. The treatment was applied by dipping the fruit treatment formulation and may also be integrated into the packaging which holds the raspberries, or applied as a spray or using other suitable methods as described elsewhere herein. After 3 days, a visible fungal infection was observed in the untreated raspberries. The BC8 treated raspberries, on the other hand, did not show an infection even after 5 days. Treated and untreated raspberries are shown in FIG. 39.

Example 33

Efficacy of Biocontrol Composition Against Infection by *Botrytis cinerea* on Grape Shelf Life Grapes were harvested from a plant and placed in a sterile container. The grapes did not have any noticeable fungal infection. Two groups of grapes were deliberately infected with *Botrytis* cinerea. FIG. 40 shows three groups of grapes which were evaluated. One was deliberately not infected labeled (−) ctrl, one was deliberately infected and was treated with a biocontrol composition BC16 labeled BC16 Product, and one was deliberately infected and was left untreated labeled (+) ctrl. The treatment was applied by dipping the fruit in the treatment formulation and may also be integrated into the packaging which holds the grapes, or applied as a spray or using other suitable methods as described elsewhere herein. The BC16 treated grapes showed no noticeable fungal infection.

Example 34

Efficacy of Biocontrol Composition Against Infection by *Botrytis cinerea* on Apple Shelf Life Apples were harvested from a plant and placed in a sterile container. The apples did not have any noticeable fungal infection. Two apples were deliberately infected with *Botrytis cinerea*. FIG. 42 shows three apples which were evaluated. One apple was deliberately not infected labeled (−) ctrl, one apple was deliberately infected and was treated with a biocontrol composition BC16 labeled BC16 Product, and one apple was deliberately infected and was left untreated labeled (+) ctrl. The treatment was applied by dipping the fruit in the treatment formulation and may also be integrated into the packaging which holds the apple or applied as a spray or using other suitable methods as described elsewhere herein. The BC16 treated apples showed a smaller area of fungal infection compared to the untreated apples. Apples were also deliberately infected and treated with BC17 labeled as BC17 Product. The apples treated by BC17 (FIG. 42) showed a smaller area of fungal infection compared to the untreated apples. FIG. 43 shows a percentage of the fruit that necrotized of the various apples.

Example 35

Efficacy of Biocontrol Composition Against Infection by *Botrytis cinerea* on Peach Shelf Life Peaches were harvested from a plant and placed in a sterile container. The peaches did not have any noticeable fungal infection. Peaches were deliberately infected with *Botrytis cinerea*. FIG. 44 shows three peaches which were evaluated. One peach was not deliberately infected labeled (−) control, one peach was deliberately infected and was treated with a biocontrol composition BC17 labeled BC17, and one peach was deliberately infected and was left untreated labeled (+) control. The treatment was applied by dipping the fruit in the treatment formulation and may also be integrated into the packaging which holds the peach or applied as a spray or using other suitable methods as described elsewhere herein. The BC17 treated peaches showed no noticeable fungal infection.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A method of preventing or reducing the growth of a pathogen on a plant, or on a seed, flower, or produce thereof, comprising:
   contacting the plant, or the seed, flower, or produce thereof, with a biocontrol composition comprising:
   (i) a first microbe or a first microbe spore, and
   (ii) a carrier,
   and wherein (a) or (b):
   (a) wherein the first microbe comprises a nucleic acid comprising a sequence at least 99% identical to any of SEQ ID NOs: 1, 2, 4, 5, 11-14, 16-18, 20, 24 or 25; or
   (b) wherein the first microbe comprises a *Gluconobacter cerinus*, and wherein the biocontrol composition further comprises a second microbe or a second microbe spore, the second microbe comprising a *Hanseniaspora uvarum*, and wherein (i) the first microbe comprises a nucleic acid comprising the 16S sequence having at least 95% identity to SEQ ID NO: 24 or (ii) the second microbe comprises a nucleic acid comprising the ITS sequence having at least 95% identity to SEQ ID NO: 25.

2. The method of claim 1, wherein the contacting comprises any of:
   (i) applying the composition to the plant, or the seed, flower, or produce thereof,
   (ii) applying the composition to soil around the plant,
   (iii) applying the composition to a packaging material used to transport or store the plant, or the seed, flower, or produce thereof, or
   (iv) integrating the composition into a process comprising washing or coating the plant, or the seed, flower, or produce thereof.

3. The method of claim 2, wherein applying the composition comprises dusting, dipping, rolling, injecting, rubbing, spraying, or brushing the composition; or wherein applying or integrating the composition comprises adding the composition to a drip line, irrigation system, chemigation system, spray, or dip.

4. The method of claim 2, wherein the composition is applied to the plant or produce thereof before the produce has been removed from the plant.

5. The method of claim 2, wherein the composition is applied to the produce after the produce has been removed from the plant.

6. The method of claim 1, further comprising applying to the plant a fertilizer, herbicide, pesticide, or another composition.

7. The method of claim 1, wherein the contacting prevents or reduces growth of the pathogen on the plant, or the seed, flower, or produce thereof.

8. The method of claim 7, wherein the contacting prevents or reduces the growth of the pathogen for at least 1 day.

9. The method of claim 7, wherein the contacting reduces the growth of the pathogen by at least 10% in relation to a control.

10. The method of claim 1, wherein the pathogen comprises a fungal pathogen.

11. The method of claim 10, wherein the fungal pathogen comprises a fungal pathogen selected from the group consisting of: *Albugo candida, Albugo occidentalis, Alternaria alternata, Alternaria cucumerina, Alternaria dauci, Alternaria solani Alternaria tenuis, Alternaria tenuissima, Alternaria tomatophila, Aphanomyces euteiches, Aphanomyces raphani, Armillaria mellea, Botrydia theobromae, Botrytis cinerea, Botrytinia fuckeliana, Bremia lactuca, Cercospora beticola, Cercosporella rubi, Cladosporium herbarum, Colletotrichum acutatum, Colletotrichum gloeosporioides, Colletotrichum lindemuthianum, Colletotrichum musae, Colletotrichum spaethanium, Cordana musae, Corynespora cassiicola, Daktulosphaira vitifoiae, Didymella bryoniae, Elsinoe ampelina, Elsinoe mangiferae, Elsinoe veneta, Erysiphe cichoracearum, Erysiphe necator, Eutypa lata, Fusarium germinareum, Fusarium oxysporum, Fusarium solani, Ganoderma boninense, Guignardia bidwellii, Gymnoconia peckiana, Helminthosporium solani, Leptosphaeria coniothyrium, Leptosphaeria maculans, Leveillula taurica, Macrophomina phaseolina, Microsphaera alni, Monilinia fructicola, Monilinia vaccinii-corymbosi, Mycosphaerella angulate, Mycosphaerella brassicicola, Mycosphaerella fragariae, Mycosphaerella fijiensis, Oidopsis taurica, Passalora fulva, Peronospora sparse, Peronospora farinosa, Phoma exigua, Phomopsis obscurans, Phomopsis vaccinia, Phomopsis viticola, Phytophthora capsica, Phytophthora erythroseptica, Phytophthora infestans, Phytophthora parasitica, Plasmopara viticola, Plasmodiophora brassicae, Podosphaera macularis, Polyscytalum pustulans, Pseudocercospora vitis, Puccinia allii, Puccinia sorghi, Pucciniastrum vaccinia, Pythium debaryanum, Pythium sulcatum, Pythium ultimum, Ralstonia solanacearum, Ramularia tulasneii, Rhizoctonia solani, Rhizopus arrhizus, Rhizopus stoloniferz, Sclerotinia minor, Sclerotinia sclerotiorum, Sclerotium cepivorum, Sclerotium rolfsii, Sclerotinia minor, Sclerotinia sclerotiorum, Septoria apiicola, Septoria lactucae, Septoria lycopersici, Septoria petroelini, Sphaceloma perseae, Sphaerotheca macularis, Spongospora subterranea, Stemphylium vesicarium, Synchytrium endobioticum, Thielaviopsis basicola, Uncinula necator, Uromyces appendiculatus, Uromyces betae, Verticillium albo-atrum, Verticillium dahliae,* and *Verticillium theobromae.*

12. The method of claim 1, wherein the plant, or the seed, flower, or produce thereof, is selected from the group consisting of: an almond, apricot, apple, artichoke, banana, barley, bean, beet, blackberry, blueberry, broccoli, Brussels sprout, cabbage, cannabis, capsicum, carrot, celery, chard, cherry, citrus, corn, cucurbit, date, fig, garlic, grape, herb, spice, kale, lettuce, oil palm, olive, onion, pea, pear, peach, peanut, papaya, parsnip, pecan, persimmon, plum, pomegranate, potato, a *Prunus*, quince, radish, raspberry, rose, rice, sloe, sorghum, soybean, spinach, strawberry, sweet potato, tobacco, tomato, turnip greens, walnut, and wheat.

13. The method of claim 1, wherein the pathogen comprises a fungal pathogen selected from the group consisting of: *Fusarium oxysporum, Mycosphaerella fijiensis, Botrytis cinerea,* a *Monilinia, Monilinia fructicola, Monilinia vaccinii-corymbosi, Phomopsis viticola, Plasmopara viticola,* a *Rhizopus, Rhizopus arrhizus, Rhizopus stoloniferz, Macrophomina phaseolina,* and *Verticillium dahlia;* and wherein the plant, or the seed, flower, or produce thereof, is selected from the group consisting of: banana, bean, peach, plum, citrus, grape, raspberry, blueberry, strawberry, blackberry, spinach, lettuce, and rice.

14. The method of claim 1, wherein: the first microbe comprises a nucleic acid comprising a sequence at least 99% identical to any of SEQ ID NOs: 1, 2, 4, 5, 11-14, 16-18, 20, 24 or 25.

15. The method of claim 1, wherein: the first microbe comprises a nucleic acid comprising the sequence of any of SEQ ID NOs: 1, 2, 4, 5, 11-14, 16-18, 20, 24 or 25.

16. The method of claim 1, wherein:
   the first microbe comprises a *Gluconobacter cerinus*, and wherein the biocontrol composition further comprises a second microbe or a second microbe spore, the second microbe comprising a *Hanseniaspora uvarum;* and the first microbe comprises a nucleic acid comprising the 16S sequence having at least 95% identity to SEQ ID NO: 24, or the second microbe comprises a nucleic acid comprising the ITS sequence having at least 95% identity to SEQ ID NO: 25.

17. The method of claim 16, wherein:

the first microbe comprises a nucleic acid comprising the 16S sequence having at least 95% identity to SEQ ID NO: 24; and the second microbe comprises a nucleic acid comprising the ITS sequence having at least 95% identity to SEQ ID NO: 25.

18. The method of claim 16, wherein:

the first microbe comprises a nucleic acid comprising the 16S sequence of SEQ ID NO: 24; and the second microbe comprises a nucleic acid comprising the ITS sequence of SEQ ID NO: 25.

19. The method of claim 1, wherein the carrier comprises a liquid carrier, a mineral carrier, or an organic carrier.

* * * * *